US012799187B2

(12) United States Patent
Van Broeck et al.

(10) Patent No.: US 12,799,187 B2
(45) **Date of Patent: *Nov. 17, 2026**

(54) ANTIBODIES TO PYROGLUTAMATE AMYLOID-β AND USES THEREOF

(71) Applicant: Janssen Pharmaceutica NV, Beerse (BE)

(72) Inventors: Bianca Van Broeck, Turnhout (BE); Marc Mercken, Turnhout (BE); Wilson Edwards, Cardiff by the Sea, CA (US); Sanjaya Singh, Blue Bell, PA (US); Jinquan Luo, Malvern, PA (US); Sherry La Porte, Horsham, PA (US); Rajkumar Ganesan, Blue Bell, PA (US); Chichi Huang, Malvern, PA (US)

(73) Assignee: Janssen Pharmaceutica NV, Beerse (BE)

( * ) Notice: Subject to any disclaimer, the term of this patent is extended or adjusted under 35 U.S.C. 154(b) by 1370 days.

This patent is subject to a terminal disclaimer.

(21) Appl. No.: 17/554,461

(22) Filed: Dec. 17, 2021

(65) Prior Publication Data

US 2022/0106387 A1 Apr. 7, 2022

Related U.S. Application Data

(63) Continuation of application No. 16/829,029, filed on Mar. 25, 2020, now Pat. No. 11,236,155.

(60) Provisional application No. 62/823,785, filed on Mar. 26, 2019.

(51) Int. Cl.

| | |
|---|---|
| ***C07K 16/18*** | (2006.01) |
| ***A61K 39/395*** | (2006.01) |
| ***A61P 25/28*** | (2006.01) |
| *A61K 39/00* | (2006.01) |

(52) U.S. Cl.

CPC .......... *C07K 16/18* (2013.01); *A61K 39/3955* (2013.01); *A61K 2039/505* (2013.01); *A61P 25/28* (2018.01); *C07K 2317/21* (2013.01); *C07K 2317/24* (2013.01); *C07K 2317/33* (2013.01); *C07K 2317/34* (2013.01); *C07K 2317/524* (2013.01); *C07K 2317/565* (2013.01); *C07K 2317/76* (2013.01); *C07K 2317/92* (2013.01); *C07K 2317/94* (2013.01)

(58) Field of Classification Search

CPC ........................... C07K 16/18; C07K 2317/21; C07K 2317/24; C07K 2317/33; C07K 2317/34; C07K 2317/524; C07K 2317/56; C07K 2317/565; C07K 2317/76; C07K 2317/92–04; A61P 25/28; A61K 39/3955; A61K 2039/505

See application file for complete search history.

(56) References Cited

U.S. PATENT DOCUMENTS

| | | | | |
|---|---|---|---|---|
| 4,166,452 | A | 9/1979 | Generales, Jr. | |
| 5,587,458 | A | 12/1996 | King et al. | |
| 5,642,870 | A | 7/1997 | Sargis | |
| 5,761,894 | A | 6/1998 | Evans | |
| 7,122,374 | B1 * | 10/2006 | Saido | C07K 16/18 424/139.1 |
| 8,058,405 | B2 | 11/2011 | Demuth et al. | |
| 8,679,498 | B2 | 3/2014 | Lu et al. | |
| 8,858,949 | B2 | 10/2014 | Yokoseki et al. | |
| 8,961,972 | B2 | 2/2015 | Lu et al. | |
| 9,585,956 | B2 | 3/2017 | Pfeifer et al. | |
| 9,828,420 | B2 | 11/2017 | Nitsch et al. | |
| 9,863,961 | B2 | 1/2018 | Sarasa Barrio | |
| 9,907,485 | B2 | 3/2018 | Hartlep et al. | |
| 9,944,696 | B2 | 4/2018 | Demattos et al. | |
| 10,519,223 | B2 | 12/2019 | Mercken et al. | |
| 10,851,156 | B2 | 12/2020 | Mercken et al. | |
| 2015/0094218 | A1 | 4/2015 | Piazza et al. | |
| 2017/0204171 | A1 | 7/2017 | Demattos et al. | |
| 2017/0363645 | A1 | 12/2017 | Kleinschmidt et al. | |
| 2018/0140689 | A1 | 5/2018 | Kleinschmidt et al. | |
| 2018/0142011 | A1 | 5/2018 | Mercken et al. | |
| 2018/0305444 | A1 | 10/2018 | Demattos et al. | |
| 2019/0046536 | A1 | 2/2019 | Demattos et al. | |
| 2021/0147528 | A1 | 5/2021 | Mercken et al. | |

FOREIGN PATENT DOCUMENTS

| | | | |
|---|---|---|---|
| WO | 2006066049 | A2 | 6/2006 |
| WO | 2007062852 | A2 | 6/2007 |
| WO | 2010004434 | A2 | 1/2010 |
| WO | 2010009987 | A2 | 1/2010 |

(Continued)

OTHER PUBLICATIONS

Mathieu Dondelinger, et al: "Understanding the Significance and Implications of Antibody Numbering and Antigen-Binding Surface/Residue Definition". Front Immunol. Oct. 16, 2018;9:2278. doi: 10.3389/fimmu.2018.02278. eCollection 2018.

(Continued)

*Primary Examiner* — Kimberly Ballard

(74) *Attorney, Agent, or Firm* — Grimes & Yvon LLP

(57) ABSTRACT

The invention provides antibodies or antigen binding fragments thereof that bind to 3pE Aβ and methods of making and using the antibodies or antigen binding fragments thereof, including use for formulations, administration and kits. The antibody and antigen binding fragments thereof and methods disclosed are useful for diagnosis, prognosis and treatment of Alzheimer's disease or other β-amyloid-related diseases.

10 Claims, 9 Drawing Sheets

Specification includes a Sequence Listing.

(56) References Cited

FOREIGN PATENT DOCUMENTS

| | | | |
|---|---|---|---|
| WO | 2011106297 | A2 | 9/2011 |
| WO | 2011151076 | A2 | 12/2011 |
| WO | 2012021469 | A1 | 2/2012 |
| WO | 2012021475 | A2 | 2/2012 |
| WO | 2015175769 | A1 | 11/2015 |
| WO | 2015191825 | A1 | 12/2015 |
| WO | 2016020880 | A2 | 2/2016 |
| WO | 2016043997 | A1 | 3/2016 |
| WO | 2016097305 | A1 | 6/2016 |
| WO | 2017009459 | A2 | 1/2017 |
| WO | 2017123517 | A1 | 7/2017 |
| WO | 2017202779 | A1 | 11/2017 |
| WO | 2017211827 | A1 | 12/2017 |
| WO | 2018031361 | A2 | 2/2018 |
| WO | 2018075339 | A1 | 4/2018 |
| WO | 2018083626 | A1 | 5/2018 |
| WO | 2018083628 | A1 | 5/2018 |
| WO | 2018194951 | A1 | 10/2018 |
| WO | 2018204546 | A2 | 11/2018 |
| WO | 2019040612 | A1 | 2/2019 |
| WO | 2020069372 | A1 | 4/2020 |

OTHER PUBLICATIONS

Vered Kunik, et al: “Structural consensus among antibodies defines the antigen binding site.” PLoS Comput Biol. 2012;8(2):e1002388. doi: 10.1371/journal.pcbi.1002388. Epub Feb. 23, 2012.

Wark K L et al, “Latest technologies for the enhancement of antibody affinity”, Advanced Drug Delivery Reviews, Elsevier, vol. 58, No. 5-6, doi:10.1016/J.ADDR.2006.01.025, ISSN 0169-409X, (Aug. 7, 2006), pp. 657-670.

Noreen R. Gonzales, et al: “Minimizing the Immunogenicity of Antibodies for Clinical Application”. Tumour Biol. Jan.-Feb. 2005;26(1):31-43. doi: 10.1159/000084184. Ninguna.

Jenny Bostrom, et al: “Improving antibody binding affinity and specificity for therapeutic development”. Methods Mol Biol. 2009;525:353-76, xiii. Doi: 10.1007/978-1-59745.

Chilean patent application No. 202102473, Dated May 25, 2025 PCT / 2021-002473.

Alaoui-Ismaili, et al., “Design of second generation therapeutic recombinant bone morphogenetic Proteins”, Cytokine & Growth Factor Reviews, vol. 20, pp. 501-507, 2009.

Altschul et al., “Basic Local Alignment Search Tool”, J. Mol. Biol., vol. 215, pp. 403-410, 1990.

Altschul, et al., “Gapped BLAST and PSI-BLAST: a new generation of protein database search programs”, Nucleic Acids Research, vol. 25 Issue 17, pp. 3389-3402, 1997.

Atwood et al., “A Unified Hypothesis of Early-and Late-Onset Alzheimer’s Disease Pathogenesis”, Journal of Alzheimer’s Disease, vol. 47, pp. 33-47, 2015.

Ausubel et al., “Current Protocols In Molecular Biology”, a joint venture between Greene Publishing Associates, Inc. and John Wiley & Sons Inc., 4955 pages, 2003.

Burgess et al., “Possible Dissociation of the Heparin-binding and Mitogenic Activities of Heparin-binding (Acidic Fibroblast) Growth Factor-1 from Its Receptor binding Activities by Site-directed Mutagenesis of a Single Lysine Residue”, The Journal of Cell Biology, vol. 111, pp. 2129-2138, 1990.

Carter et al., “High Level *Escherichia coli* Expression and Production of a Bivalent Humanized Antibody Fragment”, Bio/technology, vol. 10, pp. 163-167,1992.

Chothia et al., “Conformations of immunoglobulin hypervariable regions”, Nature, vol. 342, pp. 877-883, 1989.

Cynis et al., “Immunotherapy targeting pyroglutamate-3 Aβ: prospects and challenges”, Molecular Neurodegeneration, vol. 11 Issue 48, pp. 1-11, 2016.

Dall’Acqua et al., “Properties of Human IgG1s Engineered for Enhanced Binding to the Neonatal Fc Receptor (FcRn)”, The Journal of Biological Chemistry, vol. 281 No. 33, pp. 23514-23524, Aug. 18, 2006.

De Kimpe et al., “Intracellular accumulation of aggregated pyroglutamate amyloid beta: convergence of aging and Aβ pathology at the lysosome”, AGE, vol. 35, pp. 673-687, 2013.

Demattos et al., “A Plaque-Specific Antibody Clears Existing β-amyloid Plaques in Alzheimer’s Disease Mice”, Neuron, vol. 76, pp. 908-920, Dec. 2012.

Frost et al., “Passive Immunization against Pyroglutamate-3 Amyloid-β Reduces Plaque Burden in Alzheimer-Like Transgenic Mice: A Pilot Study”, Neurodegenerative Diseases, vol. 10, pp. 265-270, 2012.

Frost et al., “Pyroglutamate-3 Amyloid-β Deposition in the Brains of Humans, Non-Human Primates, Canines, and Alzheimer Disease-Like Transgenic Mouse Models”, American Journal of Pathology, vol. 183 Issue 2, pp. 369-381, 2013.

Frost et al., “An anti-pyroglutamate-3 Aβ vaccine reduces plaques and improves cognition in APPswe/PS1ΔE9 mice”, Neurobiol Aging, vol. 36 Issue 12, 30 pAGES, 2015.

Glukhova et al., “Updates on the Production of Therapeutic Antibodies Using Human Hybridoma Technique”, Current Pharamaceutical Design, vol. 22 Issue 7, pp. 870-878, 2016.

Guo et al., “Protein tolerance to random amino acid change”, PNAS., vol. 101 Issue 25, pp. 9205-9210, 2004.

Henikoff S et al., “Amino acid substitution matrices from protein blocks”, Proc. Natl. Acad. Sci. USA, Biochemistry, vol. 89, pp. 10915-10919, Nov. 1992.

Henstridge et al., Beyond the neuron-cellular interactions early in Alzheimer disease pathogenesis, Nature Reviews, vol. 20, pp. 94-108, 2019.

Huse et al., “Generation of a Large Combinatorial Library of the Immunoglobulin Repertoire in Phage Lambda”, Research Article, vol. 246, pp. 1275-1281, 1989.

International Search Report and Written Opinion received for Application No. PCT/EP2020/058395 on Aug. 17, 2020, 22 pages.

International Search Report and Written Opinion received for Application No. PCT/IB2017/056831 on Feb. 2, 2018, 13 pages.

Jagmag et al., “Evaluation of Models of Parkinson’s Disease”, Frontiers in Neuroscience, vol. 9 Article 503, pp. 1-13, 2016.

Janssens et al., “Passive immunotherapy with a novel antibody against 3pE-modified Aβ demonstrates potential for enhanced efficacy and favorable safety in combination with BACE inhibitor treatment in plaque-depositing mice”; Neurobiology of Disease, vol. 154, 105365, 18 pages, 2021.

Jawhar et al., “Pyroglutamate Amyloid-β (Aβ): A Hatchet Man in Alzheimer Disease”; J Biol chem, vol. 286 Issue 45, pp. 38825-38832, Nov. 2011.

Karlin et. al.,“Applications and statistics for multiple high-scoring segments in molecular sequences”, Proc. Natl. Acad. Sci, USA, vol. 90, pp. 5873-5877, Jun. 1993.

Kent, “Animal Test Systems to study Behavioral Dysfunctions of Neurodegenerative Disorders”, Neurotoxicology, vol. 12, pp. 403-413, 1991.

Kohler et al., “Continuous cultures of fused cells secreting antibody of predefined specificity”, Nature, vol. 256, pp. 495-497, Aug. 7, 1975.

Kohler et al., “Fusion between Immunoglobulin-secreting and nonsecreting myeloma Cell lines”, Eur. J. Immunol., vol. 06, pp. 292-295, 1976.

Laffleur et al., “Production of Human or Humanized Antibodies in Mice”, Antibody Methods and Protocols, Methods in Molecular Biology, vol. 901, pp. 149-159, 2012.

Lee et al., “The Application of Transgenic Mice for Therapeutic Antibody Discovery”, Antibody Methods and Protocols, Methods in Molecular Biology, vol. 901, pp. 137-148, 2012.

Lefranc et al., “IMGT, the international ImMunoGene Tics database”, Nucleic Acids Research, vol. 27 Issue 1, pp. 209-212, 1999.

Lefranc et al., “IMGT®, the international ImMunoGene Tics information system® 25 years on”, Nucleic Acids Research, vol. 43, pp. D413-D422, 2015.

Lefranc MP., “The IMGT Unique Numbering for Immunoglobulins, T-Cell Receptors, and Ig-like Domains”, The Immunologist, vol. 7, pp. 132-136, 1999.

Lefranc, “Nomenclature of the Human Immunoglobulin Heavy (IGH) Genes”, Experimental and Clinical Immunogenetics, vol. 18, pp. 100-116, 2001.

(56) References Cited

OTHER PUBLICATIONS

Lefranc, "Nomenclature of the Human Immunoglobulin Kappa (IGK) Genes", Experimental and Clinical Immunogenetics, vol. 18, pp. 161-174, 2001.
Lefranc, "Nomenclature of the Human Immunoglobulin Lambda (IGL) Genes", Experimental and Clinical Immunogenetics, vol. 18, pp. 242-254, 2001.
Lemere., "Immunotherapy for Alzheimer's disease: hoops and hurdles", Molecular Neurodegeneration, vol. 8 Issue 36, pp. 1-6, 2013.
Liu et al., "N-terminal Glutamate to Pyroglutamate Conversion in Vivo for Human IgG2 Antibodies", J Biol Chem, vol. 286 Issue 13, pp. 11211-11217, Apr. 2011.
Martin, A.C., et al., Modeling Antibody Hypervariable Loops: A Combined Alogorith, In Proceeding of PNAS, vol. 86, pp. 9268-9277, Dec. 1989.
Moore et al., "Molecular Pathophysiology of Parkinson's Disease", Annu Rev Neuros, vol. 28, pp. 57-87, 2005.
Morawski et al., "Glutaminyl Cydase in Human Cortex: Correlation with (pGlu)-Amyloid-β Load and Cognitive Dedine in Alzheimer's Disease", J Alzheimer's Disease, vol. 39, pp. 385-400, 2014.
Needleman et al., "A General Method Applicable to the Search for Similarities in the Amino Acid Sequence of Two Proteins", J Mol Biol., vol. 48, pp. 443-453, 1970.
Pandey, "Hybridoma Technology for Production of Monoclonal Antibodies", International Journal of Pharmaceutical Sciences Review and Research, vol. 1 Issue 2, pp. 88-94, Article 017, 2010.
Paul, "FV Structure and Diversity in Three Dimensions", Fundamental Immunology, Third Edition, pp. 292-295, 1993.
Pawson et al., "Assembly of cell Regulatory systems Through Protein Interaction Domains", Science, vol. 300, pp. 445-452, Apr. 2003.
Pearson et al., "Improved Tools For Biological Sequence Comparison", Proc. Natl. Acad. Sci. USA, vol. 85, pp. 2444-2448, Apr. 1988.
Potashkin et al., "Limitations of Animal Models of Parkinson's Disease", Parkinson's Disease, vol. 2011, Article ID 658083, 7 pages.
Roher et al., "APP/Aβ structural diversity and Alzheimer's disease pathogenesis", Neurochemistry International, vol. 110, pp. 1-13, 2017.
Rudikoof et al., "Single amino acid Substitution altering antigen-binding specificity", Proc Nati Acad sci, vol. 79, pp. 1979-1983, 1982.
Sarter, "Animal cognition: defining the issues", Neuroscience and Biobehavioral Reviews, vol. 28, pp. 645-650, 2004.
Scaviner et al., "Protein Displays of the Human Immunoglobulin Heavy, Kappa and Lambda Variable and Joining Regions", Experimental and Clinical Immunogenetics, vol. 16, pp. 234-240, 1999.
Singh S, et al., "Selective Targeting of the IL-23 Pathway: Generation and Characterization of a novel High-affinity humanized anti-IL23A Antibody", mAbs, vol. 07, Issue 04, pp. 778-791, 2015.
Smith TF, et al., "Comparison of Biosequences", Adv. Appl. Math., vol. 2, pp. 482-489, 1981.
Swerdlow, "Pathogenesis of Alzheimer's disease", Clinical Interventions in Aging, vol. 2 Issue 3, pp. 347-359, 2007.
Tayebati, "Animal models of cognitive dysfunction", Mechanisms of Ageing and Development, vol. 127, pp. 100-108, 2006.
Venkataramani et al., "Antibody 9D5 recognizes oligomeric pyroglutamate amyloid-β in a fraction of amyloid-β deposits in Alzheimer's disease without cross-reactivity with other protein aggregates", Journal of Alzheimer's Disease, vol. 29 Issue 2, pp. 361-371, 2012.
Wirths et al., "Identification of low molecular weight pyroglutamate Aβ oligomers in Alzheimer disease, A novel tool for therapy and diagnosis", Journal of Biological Chemistry, vol. 285 Issue 53, pp. 41517-41524, Dec. 2010.
Zhang, "Hybridoma technology for the generation of monoclonal antibodies", Antibody Methods and Protocols, Methods in Molecular Biology, vol. 901, pp. 117-135, 2012.

* cited by examiner

FIG. 6A
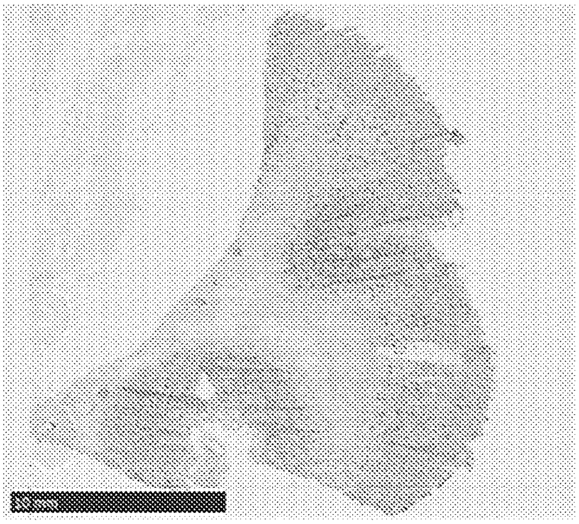
FIG. 6B
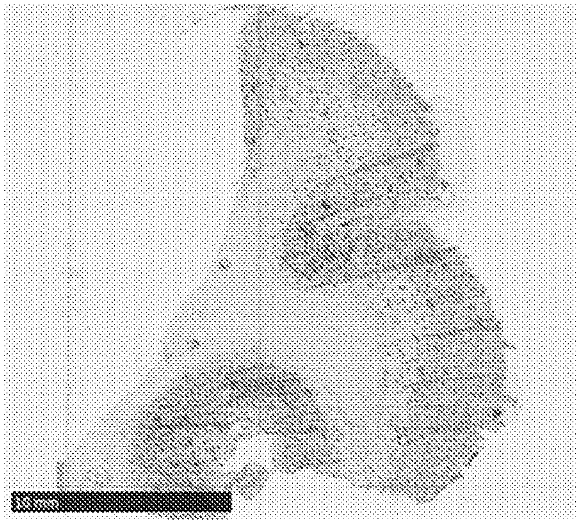
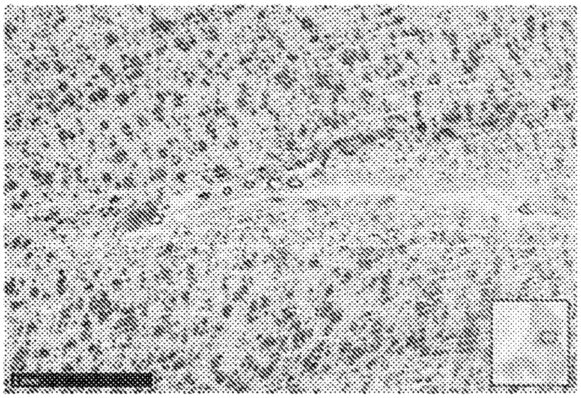
FIG. 6C
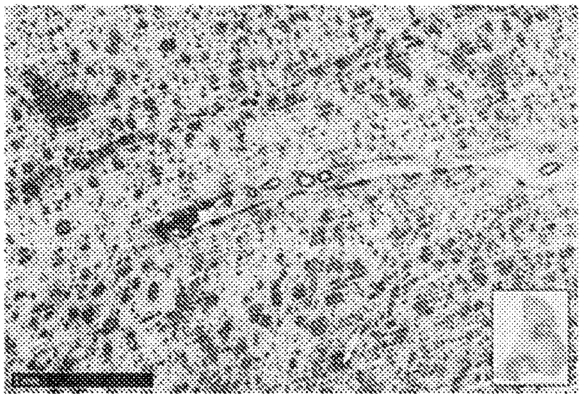
FIG. 6D

ANTIBODIES TO PYROGLUTAMATE AMYLOID-β AND USES THEREOF

CROSS-REFERENCE TO RELATED APPLICATIONS

This application is a continuation of U.S. patent application Ser. No. 16/829,029, filed on Mar. 25, 2020, which claims the benefit of priority to U.S. Provisional Application No. 62/823,785, filed on Mar. 26, 2019, each of which is hereby incorporated by reference in its entirety for all purposes.

FIELD OF THE INVENTION

This invention relates to the field of antibodies directed to amyloid-beta (Aβ) peptides and therapeutic methods using the antibodies. In particular, antibodies can be used for identifying and treating amyloid-related disorders.

REFERENCE TO SEQUENCE LISTING SUBMITTED ELECTRONICALLY

This application contains a sequence listing, which is submitted electronically via EFS-Web as an ASCII formatted sequence listing with a file name "JNJ_007_US1-Sequence Listing" and a creation date of Dec. 17, 2021, and having a size of 82 kb. The sequence listing submitted via EFS-Web is part of the specification and is herein incorporated by reference in its entirety.

BACKGROUND

Alzheimer's disease (AD) is a degenerative brain disorder characterized clinically by progressive loss of memory, cognition, reasoning, judgment and emotional stability that gradually leads to profound mental deterioration and ultimately death. Alzheimer's disease is a common cause of progressive mental failure (dementia) in the elderly. Alzheimer's disease has been observed worldwide and represents a major public health issue. The disease is currently estimated to affect more than five million individuals in the United States alone. At present it is incurable, and no treatment effectively prevents AD or reverses its symptoms or course.

The brains of individuals with AD exhibit characteristic lesions termed amyloid plaques, amyloid angiopathy (amyloid deposits in blood vessels) and neurofibrillary tangles. Large numbers of these lesions, particularly amyloid plaques and neurofibrillary tangles, are generally found in several areas of the brain important for memory and cognitive function. Amyloid plaques and amyloid angiopathy also characterize the brains of individuals with Trisomy 21 (Down's Syndrome), diffuse Lewy body disease and hereditary cerebral hemorrhage with amyloidosis of the Dutch-type (HCHWA-D).

A major constituent of amyloid plaques is a variety of amyloid-beta (Aβ) peptides that are produced by cleavage of the β-amyloid precursor protein (APP). Deposition of Aβ peptides in brain is hypothesized to be an early and necessary step in the disease cascade leading to AD. The identification of mutations in the amyloid precursor protein and presenillin genes resulting in altered Aβ production and causing familial early onset AD provides strong evidence that altered amyloid metabolism is a central event in the pathogenic process underlying the disease.

Amyloid-β peptides having pyroglutamate at the third residue (3pE Aβ) are a major species deposited in the brain of AD patients. 3pE Aβ is present in almost all diffuse and mature plaques in AD, is metabolically stable, and can play a role in both plaque seeding and stabilization (Cynis et al., Molecular Neurodegeneration, 2016; 11:48). Detectable amounts of 3pE Aβ have not been reported in CSF or plasma, thus suggesting that the target peptide is pathology specific (DeMattos et al., Neuron, 2012; 76:1-13). Antibodies that selectively bind to 3pE Aβ can be useful for immunotherapy.

SUMMARY OF THE INVENTION

As embodied and fully described, the invention relates to antibodies and antigen binding fragments thereof that bind to amyloid-β having pyroglutamate at the third residue (3pE Aβ), methods of producing antibodies or antigen binding fragments thereof that bind to 3pE Aβ, assay methods using such antibodies or antigen binding fragments thereof, and use of the antibodies or antigen binding fragments thereof of the invention for the manufacture of a medicament, for treating, delaying the onset of or reversing at least one pathology or symptom of Alzheimer's disease and other β-amyloid-related diseases. Antibodies of the invention preferentially bind Aβ peptide containing 3pE over Aβ peptide that does not contain 3pE.

In particular, described herein is an isolated monoclonal antibody or antigen-binding fragment thereof comprising a heavy complementarity determining region 1 (HCDR1), HCDR2, HCDR3, a light chain complementarity determining region 1 (LCDR1), LCDR2, and LCDR3, having the polypeptide sequences of:

a. SEQ ID NOs: 1, 2, 3, 4, 5, and 6, respectively;
b. SEQ ID NOs: 1, 7, 3, 4, 5, and 6, respectively;
c. SEQ ID NOs: 1, 7, 3, 8, 5, and 6, respectively;
d. SEQ ID NOs: 1, 2, 3, 8, 5, and 6, respectively;
e. SEQ ID NOs: 56, 57, 3, 8, 5, and 6, respectively;
f. SEQ ID NOs: 56, 57, 3, 4, 5, and 6, respectively;
g. SEQ ID NOs: 56, 58, 3, 4, 5, and 6, respectively;
h. SEQ ID NOs: 56, 7, 3, 8, 5, and 6, respectively;
i. SEQ ID NOs: 1, 57, 3, 8, 5, and 6, respectively;
j. SEQ ID NOs: 56, 7, 3, 4, 5, and 6, respectively;
k. SEQ ID NOs: 1, 57, 3, 4, 5, and 6, respectively;
l. SEQ ID NOs: 1, 58, 3, 4, 5, and 6, respectively; or
m. SEQ ID NOs: 56, 2, 3, 4, 5, and 6, respectively;

wherein the antibody or antigen-binding fragment thereof specifically binds 3pE Aβ, preferably human 3pE Aβ.

In certain embodiments, the isolated monoclonal antibody or antigen-binding fragment comprises a heavy chain variable region having a polypeptide sequence at least 95% identical to SEQ ID NO:9, 11, 13, 15, 16, 17, 19, 20, or 21, or a light chain variable region having a polypeptide sequence at least 95% identical to SEQ ID NO:10, 12, 14, 18, 22, 53, or 55.

In certain embodiments, the isolated monoclonal antibody or antigen-binding fragment thereof comprises:

a. a heavy chain variable region having the polypeptide sequence of SEQ ID NO:21, and a light chain variable region having the polypeptide sequence of SEQ ID NO:22;
b. a heavy chain variable region having the polypeptide sequence of SEQ ID NO:9, and a light chain variable region having the polypeptide sequence of SEQ ID NO:10;

c. a heavy chain variable region having the polypeptide sequence of SEQ ID NO:11, and a light chain variable region having the polypeptide sequence of SEQ ID NO:12;

d. a heavy chain variable region having the polypeptide sequence of SEQ ID NO:13, and a light chain variable region having the polypeptide sequence of SEQ ID NO:14;

e. a heavy chain variable region having the polypeptide sequence of SEQ ID NO:15, and a light chain variable region having the polypeptide sequence of SEQ ID NO:14;

f. a heavy chain variable region having the polypeptide sequence of SEQ ID NO:16, and a light chain variable region having the polypeptide sequence of SEQ ID NO:14;

g. a heavy chain variable region having the polypeptide sequence of SEQ ID NO:20, and a light chain variable region having the polypeptide sequence of SEQ ID NO:14;

h. a heavy chain variable region having the polypeptide sequence of SEQ ID NO:17, and a light chain variable region having the polypeptide sequence of SEQ ID NO:18;

i. a heavy chain variable region having the polypeptide sequence of SEQ ID NO:19, and a light chain variable region having the polypeptide sequence of SEQ ID NO:18;

j. a heavy chain variable region having the polypeptide sequence of SEQ ID NO:21, and a light chain variable region having the polypeptide sequence of SEQ ID NO:53; or k. a heavy chain variable region having the polypeptide sequence of SEQ ID NO:21, and a light chain variable region having the polypeptide sequence of SEQ ID NO:55.

In certain embodiments, the monoclonal antibody or antigen-binding fragment thereof is chimeric. In certain embodiments, the isolated monoclonal antibody or antigen-binding fragment thereof is human or humanized.

In certain embodiments, the isolated monoclonal antibody comprises:

a. a heavy chain amino acid sequence comprising SEQ ID NO:37 and a light chain amino acid sequence comprising SEQ ID NO:38;

b. a heavy chain amino acid sequence comprising SEQ ID NO:39 and a light chain amino acid sequence comprising SEQ ID NO:38 c. a heavy chain amino acid sequence comprising SEQ ID NO:37 and a light chain amino acid sequence comprising SEQ ID NO:52; or d. a heavy chain amino acid sequence comprising SEQ ID NO:39 and a light chain amino acid sequence comprising SEQ ID NO:54.

In certain embodiments, the antigen binding fragment is selected from the group of fragments consisting of Fv, F(ab'), F(ab')2 and scFv. The antibody or antigen binding fragment thereof selectively binds to 3pE Aβ peptide (e.g., Aβ3pE-40 and Aβ3pE-42), with little or no cross-reactivity to other Aβ peptides or 3-amyloid precursor protein (APP).

Also provided are isolated nucleic acids encoding the monoclonal antibodies or antigen-binding fragments thereof of the invention disclosed herein.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention. Also provided are hybridomas that produce the isolated monoclonal antibody or antigen-binding fragment thereof of the invention.

In certain embodiments, provided is a pharmaceutical composition comprising an isolated monoclonal antibody or antigen-binding fragment thereof of the invention and a pharmaceutically acceptable carrier.

Also provided are methods of treating a condition associated the formation of plaques containing beta-amyloid protein in a subject in need thereof. The methods comprise administering a monoclonal antibody or antigen binding fragment thereof of the invention or the pharmaceutical composition of the invention to the subject in need thereof. In certain embodiments, the condition is Alzheimer's disease. In certain embodiments, the condition is selected form the group consisting of dementia associated with Trisomy 21 (Down's Syndrome), diffuse Lewy body disease, inclusion body myositis, cerebral amyloid angiopathy and hereditary cerebral hemorrhage with amyloidosis of the Dutch-type (HCHWA-D).

Also provided are methods of reducing plaques associated with Alzheimer's disease in a subject in need thereof. The methods comprise administering a monoclonal antibody or antigen-binding fragment thereof of the invention or the pharmaceutical composition of the invention to the subject in need thereof.

Also provided are methods of preventing seeding activity of 3pE Aβ in a subject in need thereof. The methods comprise administering a monoclonal antibody or antigen-binding fragment thereof of the invention or the pharmaceutical composition of the invention to the subject in need thereof.

Also provided are methods of producing the monoclonal antibody or antigen-binding fragment thereof of the invention, the methods comprise culturing a cell comprising a nucleic acid encoding the monoclonal antibody or antigen-binding fragment thereof under conditions to produce the monoclonal antibody or antigen-binding fragment thereof and recovering the antibody or antigen-binding fragment thereof.

Also provided are methods of producing a pharmaceutical composition of the invention. The methods comprise combining the monoclonal antibody or antigen-binding fragment thereof of the invention with a pharmaceutically acceptable carrier to obtain the pharmaceutical composition.

An embodiment includes kits and devices comprising the antibody or antigen binding fragment thereof described above.

Further objects, features, and advantages of the present invention will be apparent to those skilled in the art from detailed consideration of the preferred embodiments that follow.

peptide. Grey traces represent the double-reference subtracted data, while the black traces represent the fitted values.

FIGS. 3A-3I show reactivity to plaques as analyzed by immunohistochemistry in formalin-fixed, paraffin-embedded (FFPE) transgenic mouse brain tissue for BAMB674 and BAMB675 versus comparator HFA molecules. Results for primary antibody concentration 0.05 μg/mL are shown. Arrows indicate regions of plaque labelling for BAMB674 and BAMB675. (A) BAMB674; (B) BAM675; (C) Antibody I; (D) Antibody II; (E) B12L; (F) CI-C7; (G) hE8L; (H) R17L; (I) R17.

Figure 4A:
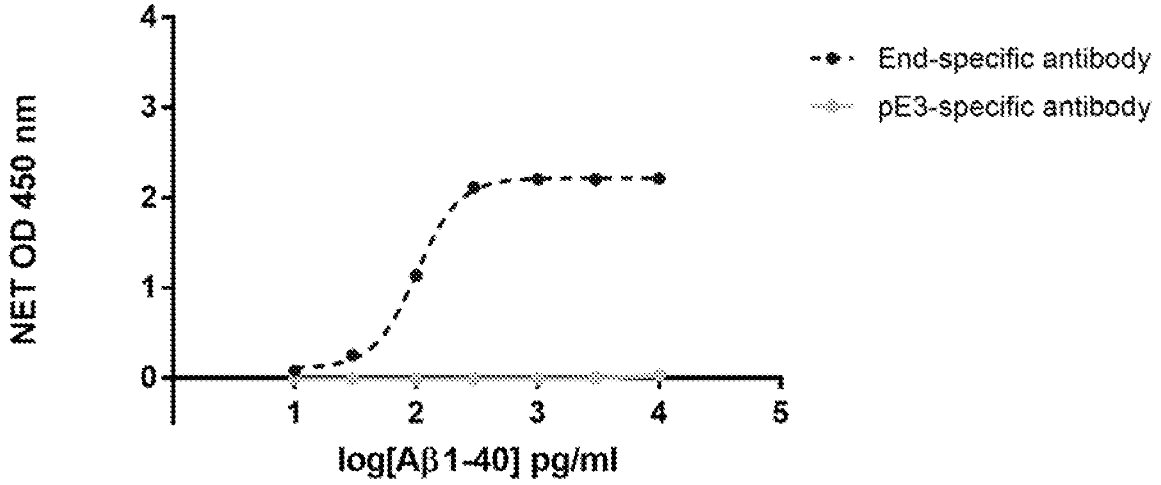
Figure 4B:
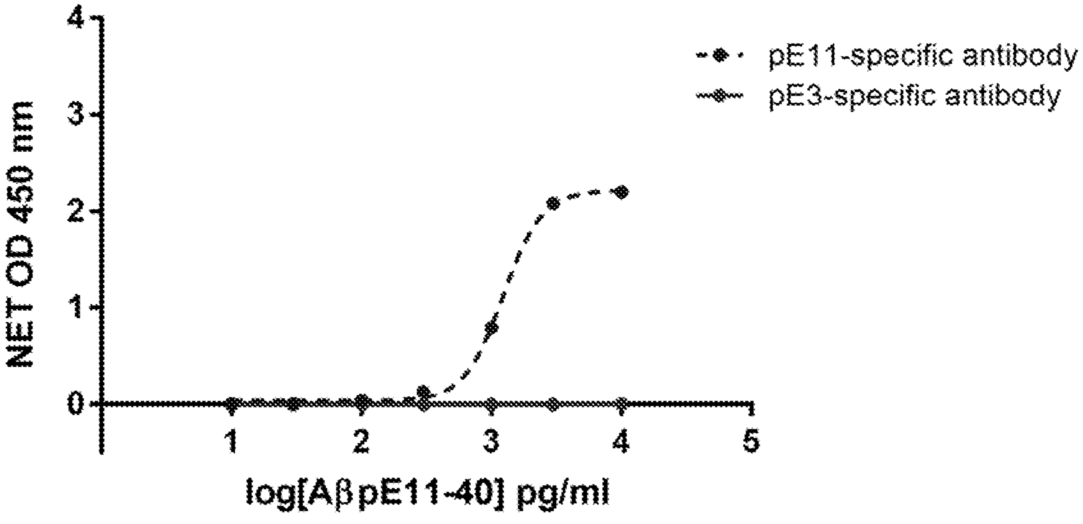
Figure 5A:
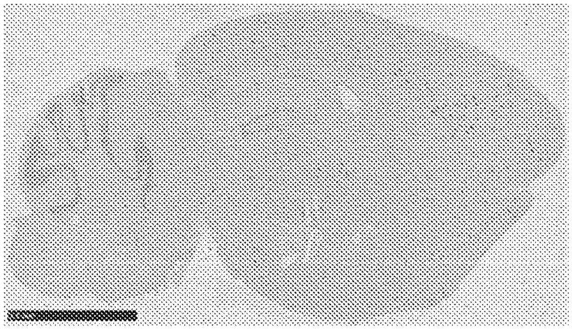
Figure 5B:
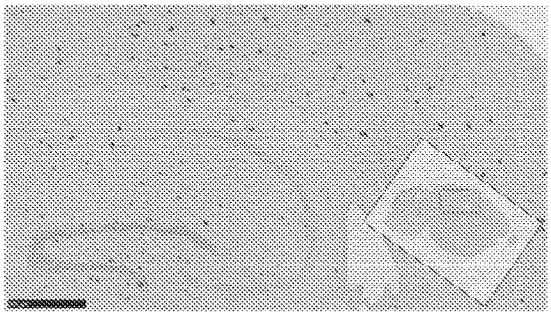
Figure 5C:
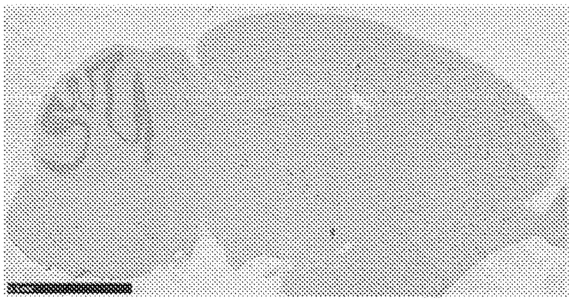
Figure 5D:
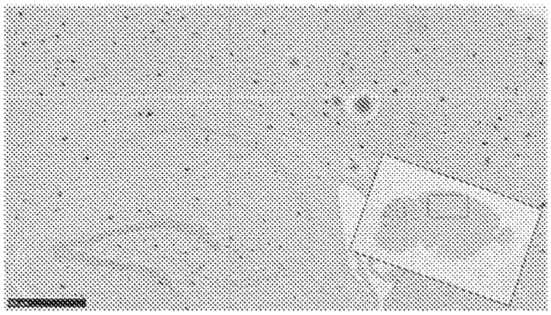
Figure 5E:
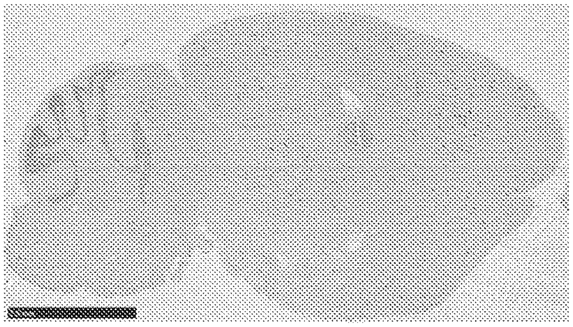
Figure 5F:
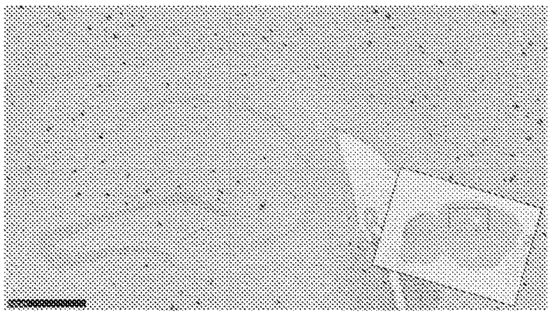

FIGS. 4A-4B show graphs demonstrating BAMB31_1 selectivity as shown by detection of synthetic human Aβ peptides in sandwich ELISA. (A) Aβ1-40 (B) AβpE11-40.

FIGS. 5A-5F show reactivity to plaques by immunohistochemistry in formalin-fixed, paraffin-embedded (FFPE) transgenic mouse brain tissue for (A-B) BAMB246 (huIgG1 chimera) (C-D) BAMB674 and (E-F) BAMB675. Small insert panel shows entire brain section stained and region of zoom-in.

FIGS. 6A-6D show reactivity to plaques by immunohistochemistry in cryopreserved AD brain tissue with (A, C) 4G8 and (B, D) BAMB31_2a (mIgG2a) at two different magnifications.

Figure 7:
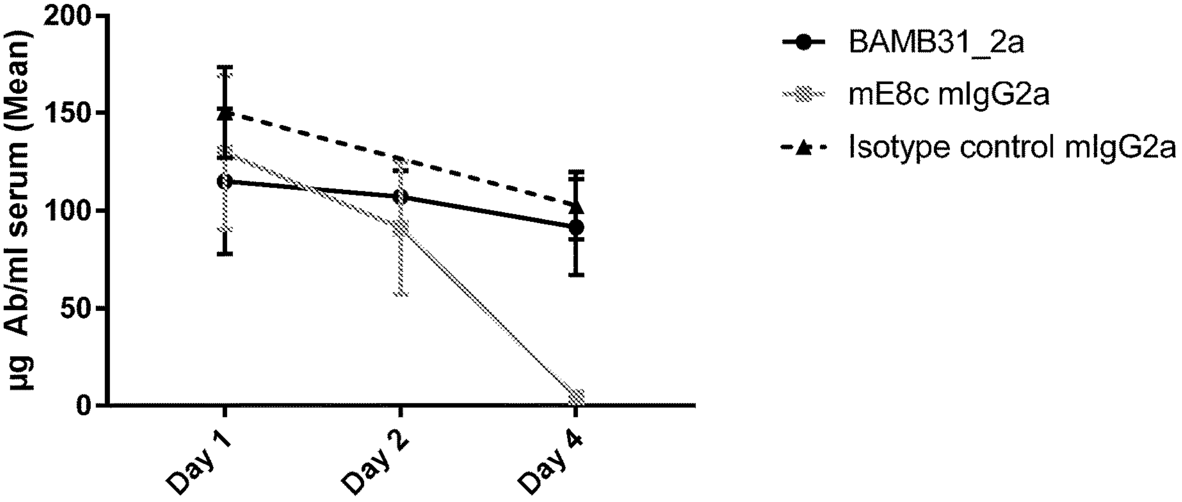

FIG. 7 shows a graph demonstrating serum antibody concentrations at different time points after a single 20 mg/kg intraperitoneal (i.p.) dose in transgenic mice.

Figure 8:
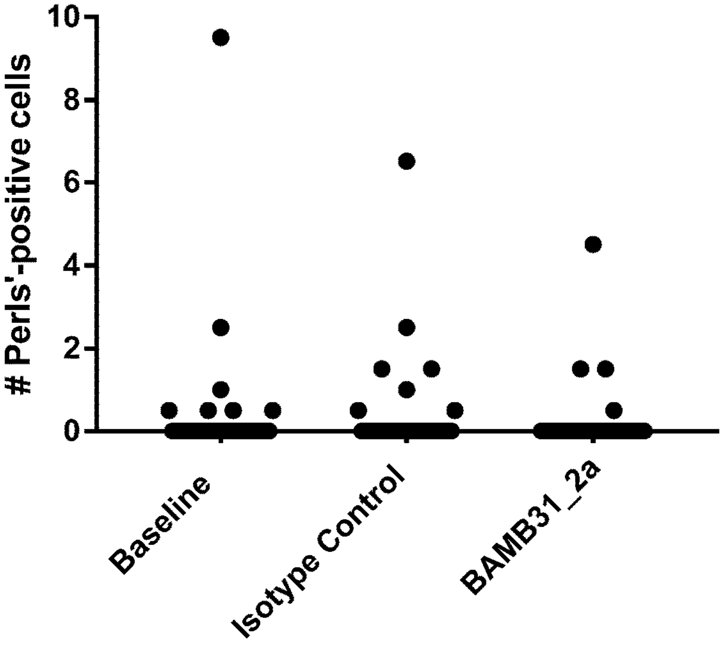

FIG. 8 shows a graph demonstrating microhemorrhages after chronic treatment with isotype control and BAMB31_2a (mIgG2a) antibodies in PDAPP mice, by evaluation of the number of Perls' positive cells.

Figure 9:
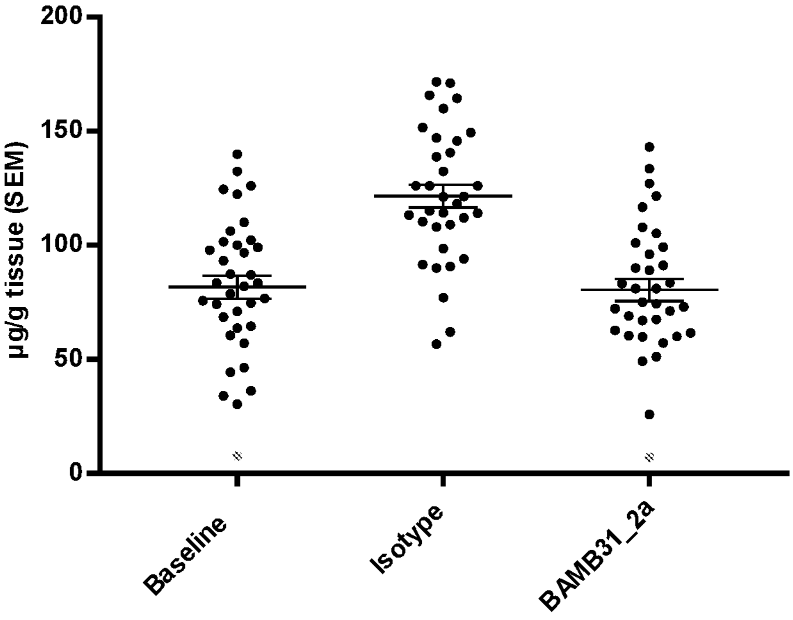

FIG. 9 shows a graph demonstrating the amyloid burden after chronic treatment with isotype control and BAMB31_2a (mIgG2a) antibodies in hippocampus of PDAPP mice, measured by immunoassay detecting Aβ1-x. Values in grey represent data points below detection limit of the assay.

Figure 10:
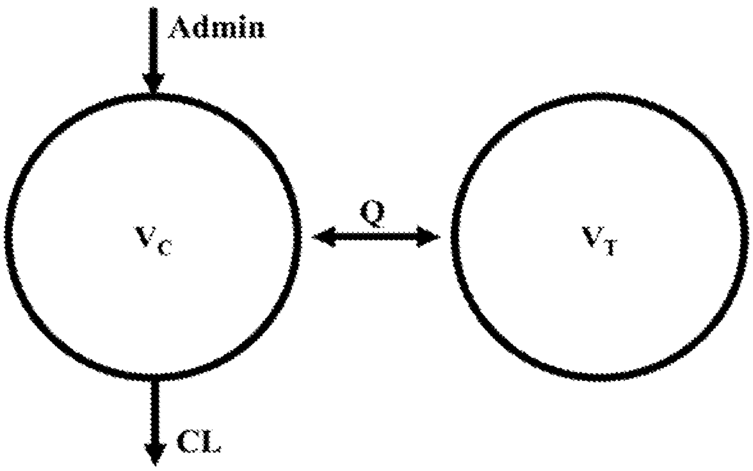

FIG. 10 shows a schematic of the two-compartment model for BAMB674 and BAMB675 monkey PK characterization.

Figure 11:
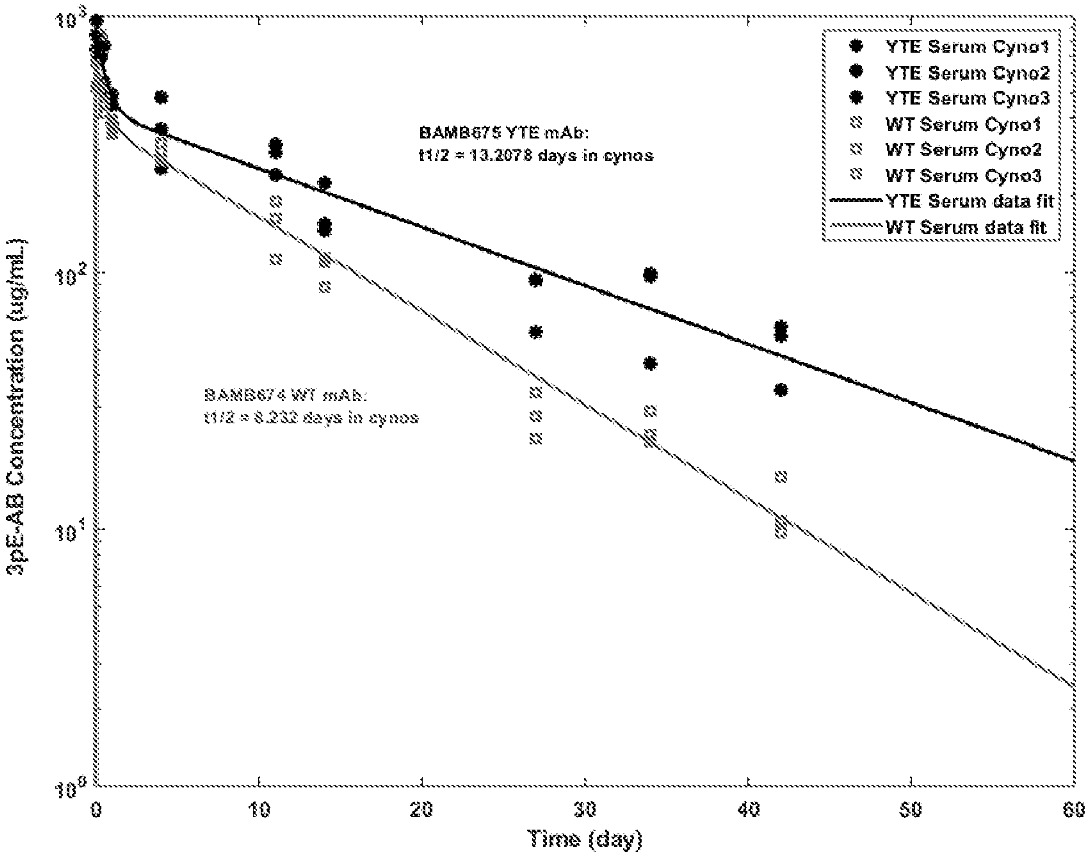

FIG. 11 shows a graph demonstrating PK vs observed data for BAMB674 and BAMB675. Serum levels of a BAM31 HFA mAb as a wild type IgG1 (WT Serum) and +YTE IgG1 (YTE Serum) isotype following intravenous (i.v.) bolus administration of 25 mg/kg in cynomolgus monkeys. Anti-Aβ 3pE antibody (3pE-AB) μg/ml concentrations are shown on a log scale on the Y-axis over time in days on the X-axis. The calculated half-life (t½) for each mAb is shown on the inset text.

Figure 12:
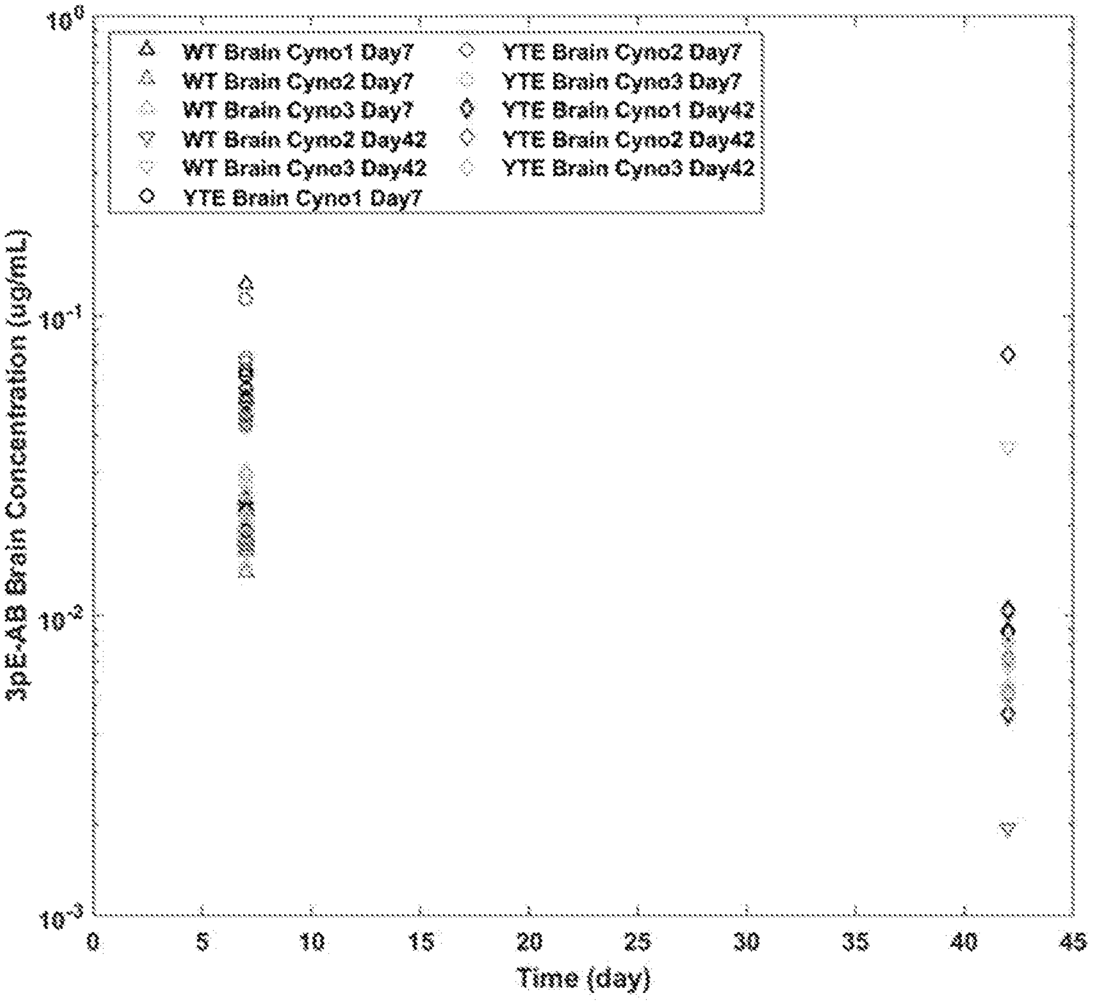

FIG. 12 shows a graph demonstrating brain concentrations observed for BAMB674 and BAMB675. Day 7 and day 42 brain lysate levels of a BAMB31 HFA mAb as a wild type IgG1 (WT brain) and a +YTE IgG1 (YTE brain) isotype following i.v. bolus administration of 25 mg/kg in cynomolgus monkeys. Anti-Aβ 3pE antibody (3pE-AB) μg/ml concentrations are shown on a log scale on the Y-axis over time in days on the X-axis.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

It is to be understood that this invention is not limited to particular methods, reagents, compounds, compositions or biological systems, which can vary. It is also to be understood that the terminology used herein is for the purpose of describing particular embodiments only and is not intended to be limiting.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

Antibodies

The invention provides an antibody or antigen binding fragment thereof that binds to 3pE Aβ peptide, especially preferentially over Aβ peptide that does not contain 3pE. Further provided are methods of producing antibodies or antigen binding fragments thereof that bind to 3pE Aβ peptide, and methods of producing hybridomas which generate antibodies or antigen binding fragments thereof that bind to 3pE Aβ peptide. The invention also includes a method of treating Alzheimer's disease and other β-amyloid-related diseases in an individual, a method of clearing plaques associated with Alzheimer's disease or other β-amyloid-related diseases, and a method of preventing plaque seeding activity of 3pE Aβ. The invention also provides kits and devices comprising the antibody or antigen binding fragment thereof for use in the methods described.

According to a particular aspect, the invention relates to an isolated monoclonal antibody or antigen-binding fragment thereof comprising a heavy complementarity determining region 1 (HCDR1), HCDR2, HCDR3, a light chain complementarity determining region 1 (LCDR1), LCDR2, and LCDR3, having the polypeptide sequences of:

a. SEQ ID NOs: 1, 2, 3, 4, 5, and 6, respectively;
b. SEQ ID NOs: 1, 7, 3, 4, 5, and 6, respectively;
c. SEQ ID NOs: 1, 7, 3, 8, 5, and 6, respectively;
d. SEQ ID NOs: 1, 2, 3, 8, 5, and 6, respectively;
e. SEQ ID NOs: 56, 57, 3, 8, 5, and 6, respectively;
f. SEQ ID NOs: 56, 57, 3, 4, 5, and 6, respectively;
g. SEQ ID NOs: 56, 58, 3, 4, 5, and 6, respectively;
h. SEQ ID NOs: 56, 7, 3, 8, 5, and 6, respectively;
i. SEQ ID NOs: 1, 57, 3, 8, 5, and 6, respectively;
j. SEQ ID NOs: 56, 7, 3, 4, 5, and 6, respectively;
k. SEQ ID NOs: 1, 57, 3, 4, 5, and 6, respectively;
l. SEQ ID NOs: 1, 58, 3, 4, 5, and 6, respectively; or
m. SEQ ID NOs: 56, 2, 3, 4, 5, and 6, respectively;

wherein the antibody or antigen-binding fragment thereof specifically binds 3pE Aβ, preferably human 3pE Aβ.

According to another particular aspect, the invention relates to an isolated monoclonal antibody or antigen-binding fragment comprising a heavy chain variable region having a polypeptide sequence at least 95% identical to SEQ ID NO:9, 11, 13, 15, 16, 17, 19, 20, or 21, or a light chain variable region having a polypeptide sequence at least 95% identical to SEQ ID NO:10, 12, 14, 18, 22, 53, or 55.

According to another particular aspect, the invention relates to an isolated monoclonal antibody or antigen-binding fragment thereof of the invention comprising:

l. a heavy chain variable region having the polypeptide sequence of SEQ ID NO:21, and a light chain variable region having the polypeptide sequence of SEQ ID NO:22;
m. a heavy chain variable region having the polypeptide sequence of SEQ ID NO:9, and a light chain variable region having the polypeptide sequence of SEQ ID NO:10;
n. a heavy chain variable region having the polypeptide sequence of SEQ ID NO:11, and a light chain variable region having the polypeptide sequence of SEQ ID NO:12;
o. a heavy chain variable region having the polypeptide sequence of SEQ ID NO:13, and a light chain variable region having the polypeptide sequence of SEQ ID NO:14;
p. a heavy chain variable region having the polypeptide sequence of SEQ ID NO:15, and a light chain variable region having the polypeptide sequence of SEQ ID NO:14;
q. a heavy chain variable region having the polypeptide sequence of SEQ ID NO:16, and a light chain variable region having the polypeptide sequence of SEQ ID NO:14;
r. a heavy chain variable region having the polypeptide sequence of SEQ ID NO:20, and a light chain variable region having the polypeptide sequence of SEQ ID NO:14;
s. a heavy chain variable region having the polypeptide sequence of SEQ ID NO:17, and a light chain variable region having the polypeptide sequence of SEQ ID NO:18;
t. a heavy chain variable region having the polypeptide sequence of SEQ ID NO:19, and a light chain variable region having the polypeptide sequence of SEQ ID NO:18
u. a heavy chain variable region having the polypeptide sequence of SEQ ID NO:21, and a light chain variable region having the polypeptide sequence of SEQ ID NO:53; or
v. a heavy chain variable region having the polypeptide sequence of SEQ ID NO:21, and a light chain variable region having the polypeptide sequence of SEQ ID NO:55.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:1, 2, 3, 4, 5 and 6, respectively or SEQ ID NOs:56, 58, 3, 4, 5, and 6, respectively or SEQ ID NOs:56, 2, 3, 4, 5, and 6, respectively or SEQ ID NOs:1, 58, 3, 4, 5 and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:21, and a light chain variable region having a polypeptide sequence at least 85%, preferably 90%, more preferably 95% or more, such as 95%, 96%, 97%, 98%, or 99% identical to SEQ ID NO:22 or 53 or 55. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22 or 53 or 55.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:1, 2, 3, 4, 5 and 6, respectively or SEQ ID NOs:56, 58, 3, 4, 5, and 6, respectively or SEQ ID NOs:56, 2, 3, 4, 5, and 6, respectively or SEQ ID NOs:1, 58, 3, 4, 5 and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:20, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:20; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:1, 7, 3, 4, 5 and 6, respectively or SEQ ID NOs:56, 57, 3, 4, 5 and 6, respectively or SEQ ID NOs:56, 7, 3, 4, 5 and 6, respectively or SEQ ID NOs:1, 57, 3, 8, 5, and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:1, 7, 3, 4, 5 and 6, respectively or SEQ ID NOs:56, 57, 3, 4, 5 and 6, respectively or SEQ ID NOs:56, 7, 3, 4, 5 and 6, respectively or SEQ ID NOs:1, 57, 3, 8, 5, and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 1, 7, 3, 4, 5 and 6, respectively or SEQ ID NOs:56, 57, 3, 4, 5 and 6, respectively or SEQ ID NOs:56, 7, 3, 4, 5 and 6, respectively or SEQ ID NOs:1, 57, 3, 8, 5, and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:16, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:16; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 1, 7, 3, 4, 5 and 6, respectively or SEQ ID NOs:56, 57, 3, 4, 5 and 6, respectively or SEQ ID NOs:56, 7, 3, 4, 5 and 6, respectively or SEQ ID NOs:1, 57, 3, 8, 5, and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 1, 7, 3, 4, 5 and 6, respectively or SEQ ID NOs:56, 57, 3, 4, 5 and 6, respectively or SEQ ID NOs:56, 7, 3, 4, 5 and 6, respectively or SEQ ID NOs:1, 57, 3, 8, 5, and 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 1, 7, 3, 8, 5 and 6, respectively or SEQ ID NOs:56, 57, 3, 8, 5, and 6, respectively or SEQ ID NOs:56, 7, 3, 8, 5, and 6, respectively or SEQ ID NOs:1, 57, 3, 8, Sand 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 1, 7, 3, 8, 5 and 6, respectively or SEQ ID NOs:56, 57, 3, 8, 5, and 6, respectively or SEQ ID NOs:56, 7, 3, 8, 5, and 6, respectively or SEQ ID NOs:1, 57, 3, 8, Sand 6, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In another particular aspect, the isolated monoclonal antibody comprises:

a. a heavy chain amino acid sequence comprising SEQ ID NO:37 and a light chain amino acid sequence comprising SEQ ID NO:38;
b. a heavy chain amino acid sequence comprising SEQ ID NO:39 and a light chain amino acid sequence comprising SEQ ID NO:38;
c. a heavy chain amino acid sequence comprising SEQ ID NO:37 and a light chain amino acid sequence comprising SEQ ID NO:52; or
d. a heavy chain amino acid sequence comprising SEQ ID NO:39 and a light chain amino acid sequence comprising SEQ ID NO:55.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to antigen-binding fragments, wherein the antigen-binding fragment is selected from the group of fragments consisting of Fv, F(ab'), F(ab')2 and scFv. The antibody or antigen binding fragment thereof selectively binds to 3pE Aβ peptide (e.g., Aβ3pE-40 and Aβ3pE-42), with little or no cross-reactivity to other Aβ peptides or β-amyloid precursor protein (APP).

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible, or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

The present invention provides an isolated antibody or antigen binding fragment thereof which binds to 3pE Aβ. The term "antibody" refers herein to an immunoglobulin protein capable of binding an antigen or portion thereof, particularly an immunoglobulin protein capable of specifically binding to 3pE Aβ. Antibody binding to an antigen can be measured by methods known to those skilled in the art, an example being the use of a BIAcore™ instrument. An antibody or antigen-binding antibody fragment is said to specifically bind an antigen when the dissociation constant is less than or equal to 1 μM, preferably less than or equal to 100 nM and most preferably less than or equal to 10 nM.

Antigen binding fragments of antibodies refers to a fragment of an antibody that can bind to the antigen that the intact antibody binds to and competes with the intact antibody for antigen binding. Antigen binding fragments comprise a portion of an intact antibody that allows for antigen binding (i.e., the variable region of the intact antibody). Antigen binding fragments can include, but are not limited to, a Fab, a Fab', a F(ab')2, an Fv fragment, a disulfide stabilized Fv fragment (dsFv), a (dsFv)2, a bispecific dsFv (dsFv-dsFv'), a single-chain antibody molecule (e.g., scFV), a diabody, a minibody, a nanobody, a linear antibody, a single domain antibody (sdab), a camelized single domain antibody, a multispecific antibody formed from antibody fragments, and any other antibody fragment that binds to an antigen but does not comprise a complete antibody structure.

Antibodies are made up of two heavy chains and two light chains. Each heavy chain has one variable domain or region ($V_H$) followed by a constant domain or region ($C_H1$), a hinge region, and two more constant domains or regions ($C_H2$ and $C_H3$). Each light chain has one variable domain or region ($V_L$) and one constant domain or region ($C_L$). The variable domains or regions of the heavy and light chains form the paratope of the antibody (a structure analogous to a lock), which is specific for a particular epitope (similarly analogous to a key), allowing the paratope and the epitope to bind together with precision. Within the variable domain, variable loops of β-strands, three each on the light and heavy chains, are responsible for binding to the antigen. These loops are referred to as the complementarity determining regions (CDRs, namely CDR1, CDR2, and CDR3).

CDRs are defined as complementarity determining regions of an antibody. These are the hypervariable regions of antibody heavy and light chains that are primarily responsible for binding to the antigen. There are three CDRs (CDR1, CDR2 and CDR3) in each of the heavy and light chain variable regions. The light chain variable complementarity determining regions are alternatively referred to as LCDR1, LCDR2, and LCDR3, and the heavy chain variable complementarity determining regions are alternatively referred to as HCDR1, HCDR2, and HCDR3. The CDRs of an antibody can be defined in a number of ways. For example, the CDRs within the variable region can be identified in accordance with the definitions of the Kabat, Chothia, IMGT and/or conformational definitions or any method of CDR determination well known in the art. Antibody CDRs can be identified as the hypervariable regions originally defined by Kabat (Kabat et al., 1992, Sequences of Proteins of Immunological Interest, 5th ed., Public Health Service, NIH, Washington D.C.), the structural loop structures originally described by Chothia (Chothia et al., Nature 342:877-883 (1989)) or the unique numbering system of IMGT (Lefranc, The Immunologist 7:132-136 (1999); Lefranc, et al., Nucleic Acids Res. 27:209-212 (1999); Scaviner et al., Exp. Clin. Immunogenet. 16:234-240 (1999); Lefranc, et al., Nucleic Acids Res. 43:D413-422 (2015)).

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated," but the same antibody separated from the coexisting materials of its natural state is "isolated," as the term is employed herein, e.g., an "isolated antibody" can refer to an antibody which is substantially free of other antibodies having different antigenic specificities (i.e., an isolated antibody that specifically binds to 3pE Aβ is substantially free of antibodies that do not bind to 3pE Aβ). Antibodies can occur in a composition, such as an immunoassay reagent, which are not naturally occurring compositions, and therein remain isolated antibodies within the meaning of that term as it is employed herein.

Methods of producing antibodies comprise inoculating a host with a desired immunogen. Suitable hosts include, but are not limited to, mice, rats, hamsters, guinea pigs, rabbits, chickens, donkeys, horses, monkeys, chimpanzees, orangutans, gorillas, humans, and any species capable of mounting a mature immune response. The immunization procedures are well established in the art and are set forth in numerous treatises and publications including "*The Immunoassay Handbook,*" 2nd Edition, edited by David Wild (Nature Publishing Group, 2000).

Preferably, an immunogen embodying features of the present invention is administered to a host subject, e.g., an animal or human, in combination with an adjuvant. Suitable adjuvants include, but are not limited to, Freund's adjuvant, powdered aluminum hydroxide (alum), aluminum hydroxide together with *Bordetella pertussis*, and monophosphoryl lipid A-synthetic trehalose dicorynomycolate (MPL-TDM).

Typically, an immunogen or a combination of an immunogen and an adjuvant is injected into a mammalian host by one or multiple subcutaneous or intraperitoneal injections. Preferably, the immunization program is carried out over at least one week, and more preferably, over two or more weeks. Polyclonal antibodies produced in this manner can be isolated and purified utilizing methods well know in the art.

Monoclonal antibodies can be produced by the well-established hybridoma methods of Kohler and Milstein, e.g., *Nature* 256:495-497 (1975). Hybridoma methods typically involve immunizing a host or lymphocytes from a host, harvesting the monoclonal antibody secreting or having the potential to secrete lymphocytes, fusing the lymphocytes to immortalized cells, and selecting cells that secrete the desired monoclonal antibody.

A host can be immunized to elicit lymphocytes that produce or are capable of producing antibodies specific for an immunogen. Alternatively, the lymphocytes can be immunized in vitro. If human cells are desired, peripheral blood lymphocytes can be used, although spleen cells or lymphocytes from other mammalian sources are preferred.

The lymphocytes can be fused with an immortalized cell line to form hybridoma cells, a process which can be facilitated by the use of a fusing agent, e.g., polyethylene glycol. By way of illustration, mutant rodent, bovine, or human myeloma cells immortalized by transformation can be used. Substantially pure populations of hybridoma cells, as opposed to unfused immortalized cells, are preferred. Thus, following fusion, the cells can be grown in a suitable medium that inhibits the growth or survival of unfused, immortalized cells, for example, by using mutant myeloma cells that lack the enzyme hypoxanthine guanine phosphoribosyl transferase (HGPRT). In such an instance, hypoxanthine, aminopterin, and thymidine can be added to the medium (HAT medium) to prevent the growth of HGPRT-deficient cells while permitting hybridomas to grow.

Preferably, immortalized cells that fuse efficiently, can be isolated from mixed populations by selection in a medium such as HAT, and support stable and high-level expression of antibody following fusion. Preferred immortalized cell lines include myeloma cell lines available from the American Type Culture Collection, Manassas, VA.

One aspect of the invention is a method of producing a hybridoma cell line capable of producing a monoclonal antibody that binds to amyloid beta peptides. Such methods are commonly known to those skilled in the art, and generally comprise: (i) selecting a host for antibody production; (ii) inoculating the host with a desired immunogen; (iii) fusing a cell line from the inoculated host with a continuously dividing cell to create a fused cell capable of producing a monoclonal antibody that binds to the immunogen; and (iv) cloning the fused cell to obtain a hybridoma cell line.

A method of the invention includes producing a hybridoma cell line capable of producing a monoclonal antibody that binds to 3pE Aβ peptide. The hybridoma can be produced by immunizing an animal from which hybridomas can be produced, such as a Balb/c mouse, with initial intraperitoneal injections of the desired immunogens, such as an Aβ peptide having a pyroglutamate, in Freund's adjuvant, followed by booster injections, for example, every one to two weeks. The subsequent fusion of the isolated spleen can be carried out using any techniques commonly known to those of ordinary skill in the art, preferably using SP2/0 cells by a modified procedure of Kohler and Milstein (Eur. J. Immunol., 1976; 6:292-295). Hybridomas can be screened to determine which produce antibodies specific for the 3pE Aβ peptides. The screen can be done in a standard assay, such as an ELISA or RIA assay. One aspect of the invention is a method of producing a hybridoma cell line that generates the monoclonal antibody BAMB31_1 or a humanized version thereof.

Monoclonal antibodies can also be produced by recombinant methods known in the art, e.g., as described in U.S. Pat. No. 4,166,452. DNA encoding monoclonal antibodies can be isolated and sequenced using conventional procedures, e.g., using oligonucleotide probes that specifically bind to murine heavy and light antibody chain genes, preferably to probe DNA isolated from monoclonal antibody hybridoma cells lines secreting antibodies specific for Aβ having a pyroglutamate.

Antibody fragments that contain specific binding sites for amyloid beta peptides can also be generated. Such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 256:1270-1281 (1989)). Fab, Fv and ScFv antibody fragments can all be expressed in and secreted from *Escherichia coli*, allowing for the production of large amounts of these fragments. Alternatively, Fab'-SH fragments can be directly recovered from *E. coli* and chemically coupled to form $F(ab')_2$ fragments (Carter et al., *BioTechnology* 10:163-167 (1992)). Other techniques for the production of antibody fragments are known to those skilled in the art. Single chain Fv fragments (scFv) are also envisioned (see, e.g., U.S. Pat. Nos. 5,761,894 and 5,587,458). Fv and sFv fragments are the only species with intact combining sites that are devoid of constant regions; thus, they are likely to show reduced non-specific binding. The antibody fragment can also be a "linear antibody" e.g., as described in U.S. Pat. No. 5,642,870, for example.

It is thus an object of the invention to provide isolated monoclonal antibodies expressed by the aforementioned hybridoma cells, the antibodies being capable of specifically recognizing 3pE Aβ. The isolated monoclonal antibodies can be expressed by hybridoma cells or recombinantly.

Preferably, the antibody or antigen binding fragment thereof of the invention binds selectively to 3pE Aβ, with little or no cross-reactivity to other Aβ that do not have 3pE or β-amyloid precursor protein (APP). In particular, the antibody or antigen binding fragment thereof of the invention binds selectively to Aβ 3pE-40 (SEQ ID NO:40 or SEQ ID NO:45) and Aβ 3pE-42 (SEQ ID NO:51) peptides with little or no cross-reactivity to other non-3pE containing Aβ peptides or APP.

Table 1 provides the amino acid sequences of the antibody of the invention. The CDRs of the heavy and light chain variable regions as defined by Kabat, Chothia and IMGT are set forth as separate sequences.

TABLE 1

3pE Aβ monoclonal antibody sequences

| mAb | Region | SEQ ID NO: | Sequence |
|---|---|---|---|
| BAMB31_1 | Heavy Chain | | |

TABLE 1-continued

3pE Aβ monoclonal antibody sequences

| mAb | Region | SEQ ID NO: | Sequence |
|---|---|---|---|
| | VH | 9 | EIQLQQSGPELVKPGTSVKV SCKASGHVFTSYDMYWVKQS HGKSLEWIGYIDSDNGDTSY NQKFKGKATLTVDKSSSTAY MHLNSLTSEDSAVYYCAYYR YAMDYWGQGTSVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | DSDNGDTS |
| | HCDR3 | 3 | YRYAMDY |
| | Light Chain | | |
| | VL | 10 | DWMTQTPLTLSVTIGQPASI SCKSSQSLLDSNGKTYLTWL LQRPGQSPKRLIYLVSKLDS GVPDRFTGSGAGTDFTLKII RVEAEDLGVYYCWQGTHFPY TFGGGTKLEIK |
| | LCDR1 | 8 | KSSQSLLDSNGKTYLT |
| | LCDR2 | 5 | LVSKLDS |
| | LCDR3 | 6 | WQGTHFPYT |
| BAMB31_2a | Heavy Chain | 23 | EIQLQQSGPELVKPGTSVKV SCKASGHVFTSYDMYWVKQS HGKSLEWIGYIDSDNGDTSY NQKFKGKATLTVDKSSSTAY MHLNSLTSEDSAVYYCAYYR YAMDYWGQGTSVTVSSAKTT APSVYPLAPVCGDTTGSSVT LGCLVKGYFPEPVTLTWNSG SLSSGVHTFPAVLQSDLYTL SSSVTVTSSTVVPSQSITCN VAHPASSTKVDKKIEPRGPT IKPCPPCKCPAPNLLGGPSV FIFPPKIKDVLMISLSPIVT CVVVDVSEDDPDVQISVVFV NNVEVHTAQTQTHREDYNST LRVVSALPIQHQDWMSGKEF KCKVNNKDLPAPIERTISKP KGSVRAPQVYVLPPPEEEMT KKQVTLTCMVTDFMPEDIYV EWTNNGKTELNYKNTEPVLD SDGSYFMYSKLRVEKKNWVE RNSYSCSVVHEGLHNHHTTK SFSRTPGK |
| | VH | 9 | EIQLQQSGPELVKPGTSVKV SCKASGHVFTSYDMYWVKQS HGKSLEWIGYIDSDNGDTSY NQKFKGKATLTVDKSSSTAY MHLNSLTSEDSAVYYCAYYR YAMDYWGQGTSVTVSS |
| | HCDR1 Kabat | 1 | SYDMY |
| | HCDR1 AbM | 56 | GHVFTSYDMY |

TABLE 1-continued

3pE Aβ monoclonal antibody sequences

| mAb | Region | SEQ ID NO: | Sequence |
|---|---|---|---|
| | HCDR2 Kabat | 7 | YIDSDNGDTSYNQKFKG |
| | HCDR2 AbM | 57 | DSDNGDTS |
| | HCDR3 | 3 | YRYAMDY |
| | Light Chain | 24 | DVVMTQTPLTLSVTIGQPAS ISCKSSQSLLDSNGKTYLTW LLQRPGQSPKRLIYLVSKLD SGVPDRFTGSGAGTDFTLKI IRVEAEDLGVYYCWQGTHFP YTFGGGTKLEIKRADAAPTV SIFPPSSEQLTSGGASWCFL NNFYPKDINVKWKIDGSERQ NGVLNSWTDQDSKDSTYSMS STLTLTKDEYERHNSYTCEA THKTSTSPIVKSFNRNEC |
| | VL | 10 | DVVMTQTPLTLSVTIGQPAS ISCKSSQSLLDSNGKTYLTW LLQRPGQSPKRLIYLVSKLD SGVPDRFTGSGAGTDFTLKI IRVEAEDLGVYYCWQGTHFP YTFGGGTKLEIK |
| | LCDR1 | 8 | KSSQSLLDSNGKTYLT |
| | LCDR2 | 5 | LVSKLDS |
| | LCDR3 | 6 | WQGTHFPYT |
| BAMB246 | Heavy Chain | 25 | EIQLQQSGPELVKPGTSVKV SCKASGHVFTSYDMYWVKQS HGKSLEWIGYIDSDNGDTSY NQKFKGKATLTVDKSSSTAY MHLNSLTSEDSAVYYCAYYR YAMDYWGQGTSVTVSSASTK GPSVFPLAPSSKSTSGGTAA LGCLVKDYFPEPVTVSWNSG ALTSGVHTFPAVLQSSGLYS LSSVVTVPSSSLGTQTYICN VNHKPSNTKVDKKVEPKSCD KTHTCPPCPAPELLGGPSVF LFPPKPKDTLMISRTPEVTC VVVDVSHEDPEVKFNWYVDG VEVHNAKTKPREEQYNSTYR VVSVLTVLHQDWLNGKEYKC KVSNKALPAPIEKTISKAKG QPREPQVYTLPPSREEMTKN QVSLTCLVKGFYPSDIAVEV VESNGQPENNYKTTPPVLDS DGSFFLYSKLTVDKSRWQQG NVFSCSVMHEALHNHYTQKS LSLSPGK |
| | VH | 9 | EIQLQQSGPELVKPGTSVKV SCKASGHVFTSYDMYWVKQS HGKSLEWIGYIDSDNGDTSY NQKFKGKATLTVDKSSSTAY MHLNSLTSEDSAVYYCAYYR YAMDYWGQGTSVTVSS |
| | HCDR1 Kabat | 1 | SYDMY |
| | HCDR1 AbM | 56 | GHVFTSYDMY |

TABLE 1-continued

3pE Aβ monoclonal antibody sequences

| mAb | Region | SEQ ID NO: | Sequence |
|---|---|---|---|
| | HCDR2 Kabat | 7 | YIDSDNGDTSYNQKFKG |
| | HCDR2 AbM | 57 | YIDSDNGDTS |
| | HCDR3 | 3 | YRYAMDY |
| | Light Chain | 26 | DVVMTQTPLTLSVTIGQPAS ISCKSSQSLLDSNGKTYLTW LLQRPGQSPKRLIYLVSKLD SGVPDRFTGSGAGTDFTLKI IRVEAEDLGVYYCWQGTHFP YTFGGGTKLEIKRTVAAPSV FIFPPSDEQLKSGTASWCLL NNFYPREAKVQWKVDNALQS GNSQESVTEQDSKDSTYSLS STLTLSKADYEKHKVYACEV THQGLSSPVTKSFNRGEC |
| | VL | 10 | DVVMTQTPLTLSVTIGQPAS ISCKSSQSLLDSNGKTYLTW LLQRPGQSPKRLIYLVSKLD SGVPDRFTGSGAGTDFTLKI IRVEAEDLGVYYCWQGTHFP YTFGGGTKLEIK |
| | LCDR1 | 8 | KSSQSLLDSNGKTYLT |
| | LCDR2 | 5 | LVSKLDS |
| | LCDR3 | 6 | WQGTHFPYT |
| BAMB611 | Heavy Chain | 27 | QVQLVQSGAEVKKPGASVKV SCKASGHVFTSYDMYWVRQA PGQGLEWMGYIDSDNGDTSY NQKFKGRVTMTVDTSTSTVY MELSSLRSEDTAVYYCAYYR YAMDYWGQGTLVTVSSASTK GPSVFPLAPSSKSTSGGTAA LGCLVKDYFPEPVTVSWNSG ALTSGVHTFPAVLQSSGLYS LSSVVTVPSSSLGTQTYICN VNHKPSNTKVDKKVEPKSCD KTHTCPPCPAPELLGGPSVF LFPPKPKDTLMISRTPEVTC VVVDVSHEDPEVKFNWYVDG VEVHNAKTKPREEQYNSTYR VVSVLTVLHQDWLNGKEYKC KVSNKALPAPIEKTISKAKG QPREPQVYTLPPSREEMTKN QVSLTCLVKGFYPSDIAVEW ESNGQPENNYKTTPPVLDSD GSFFLYSKLTVDKSRWQQGN VFSCSVMHEALHNHYTQKSL SLSPGK |
| | VH | 11 | QVQLVQSGAEVKKPGASVKV SCKASGHVFTSYDMYWVRQA PGQGLEWMGYIDSDNGDTSY NQKFKGRVTMTVDTSTSTVY MELSSLRSEDTAVYYCAYYR YAMDYWGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |

TABLE 1-continued

3pE Aβ monoclonal antibody sequences

| mAb | Region | SEQ ID NO: | Sequence |
|---|---|---|---|
| | HCDR2 AbM | 57 | YIDSDNGDTS |
| | HCDR3 | 3 | YRYAMDY |
| | Light Chain | 28 | DVVMTQSPLSLPVTLGQPAS<br>ISCKSSQSLLDSNGKTYLTW<br>FQQRPGQSPRRLIYLVSKLD<br>SGVPDRFSGSGSGTDFTLKI<br>SRVEAEDVGVYYCWQGTHFP<br>YTFGGGTKLEIKRTVAAPSV<br>FIFPPSDEQLKSGTASVVCL<br>LNNFYPREAKVQWKVDNALQ<br>SGNSQESVTEQDSKDSTYSL<br>SSTLTLSKADYEKHKVYACE<br>VTHQGLSSPVTKSFNRGEC |
| | VL | 12 | DVVMTQSPLSLPVTLGQPAS<br>ISCKSSQSLLDSNGKTYLTW<br>FQQRPGQSPRRLIYLVSKLD<br>SGVPDRFSGSGSGTDFTLKI<br>SRVEAEDVGVYYCWQGTHFP<br>YTFGGGTKLEIK |
| | LCDR1 | 8 | KSSQSLLDSNGKTYLT |
| | LCDR2 | 5 | LVSKLDS |
| | LCDR3 | 6 | WQGTHFPYT |
| BAMB612 | Heavy Chain | 29 | QVQLVQSGAEVKKPGASVKV<br>SCKASGHVFTSYDMYWVRQS<br>PGQGLEWIGYIDSDNGDTSY<br>NQKFKGRVTLTVDTSTSTVY<br>MELSSLRSEDTAVYYCAYYR<br>YAMDYWGQGTLVTVSSASTK<br>GPSVFPLAPSSKSTSGGTAA<br>LGCLVKDYFPEPVTVSWNSG<br>ALTSGVHTFPAVLQSSGLYS<br>LSSVVTVPSSSLGTQTYICN<br>VNHKPSNTKVDKKVEPKSCD<br>KTHTCPPCPAPELLGGPSVF<br>LFPPKPKDTLMISRTPEVTC<br>VVVDVSHEDPEVKFNWYVDG<br>VEVHNAKTKPREEQYNSTYR<br>VVSVLTVLHQDWLNGKEYKC<br>KVSNKALPAPIEKTISKAKG<br>QPREPQVYTLPPSREEMTKN<br>QVSLTCLVKGFYPSDIAVEW<br>ESNGQPENNYKTTPPVLDSD<br>GSFFLYSKLTVDKSRWQQGN<br>VFSCSVMHEALHNHYTQKSL<br>SLSPGK |
| | VH | 13 | QVQLVQSGAEVKKPGASVKV<br>SCKASGHVFTSYDMYWVRQS<br>PGQGLEWIGYIDSDNGDTSY<br>NQKFKGRVTLTVDTSTSTVY<br>MELSSLRSEDTAVYYCAYYR<br>YAMDYWGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | YIDSDNGDTS |
| | HCDR3 | 3 | YRYAMDY |
| | Light Chain | 30 | DVVMTQSPLSLPVTLGQPAS<br>ISCKSSQSLLDSRAKTYLTW<br>LQQRPGQSPRRLIYLVSKLD<br>SGVPDRFSGSGSGTDFTLKI<br>SRVEAEDVGVYYCWQGTHFP<br>YTFGGGTKLEIKRTVAAPSV<br>FIFPPSDEQLKSGTASVVCL<br>LNNFYPREAKVQWKVDNALQ<br>SGNSQESVTEQDSKDSTYSL<br>SSTLTLSKADYEKHKVYACE<br>VTHQGLSSPVTKSFNRGEC |
| | VL | 14 | DVVMTQSPLSLPVTLGQPAS<br>ISCKSSQSLLDSRAKTYLTW<br>LQQRPGQSPRRLIYLVSKLD<br>SGVPDRFSGSGSGTDFTLKI<br>SRVEAEDVGVYYCWQGTHFP<br>YTFGGGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB613 | Heavy Chain | 31 | QVQLVQSGAEVKKPGASVKV<br>SCKASGHVFTSYDMYWVRQA<br>PGQGLEWIGYIDSDNGDTSY<br>NQKFKGKVTLTVDTSTSTVY<br>MELSSLRSEDTAVYYCAYYR<br>YAMDYWGQGTLVTVSSASTK<br>GPSVFPLAPSSKSTSGGTAA<br>LGCLVKDYFPEPVTVSWNSG<br>ALTSGVHTFPAVLQSSGLY<br>SLSSVVTVPSSSLGTQTYIC<br>NVNHKPSNTKVDKKVEPKSC<br>DKTHTCPPCPAPELLGGPSV<br>FLFPPKPKDTLMISRTPEVT<br>CVVVDVSHEDPEVKFNWYVD<br>GVEVHNAKTKPREEQYNSTY<br>RVVSVLTVLHQDWLNGKEYK<br>CKVSNKALPAPIEKTISKAK<br>GQPREPQVYTLPPSREEMTK<br>NQVSLTCLVKGFYPSDIAVE<br>WESNGQPENNYKTTPPVLDS<br>DGSFFLYSKLTVDKSRWQQG<br>NVFSCSVMHEALHNHYTQKS<br>LSLSPGK |
| | VH | 15 | QVQLVQSGAEVKKPGASVKV<br>SCKASGHVFTSYDMYWVRQA<br>PGQGLEWIGYIDSDNGDTSY<br>NQKFKGKVTLTVDTSTSTVY<br>MELSSLRSEDTAVYYCAYYR<br>YAMDYVVGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | YIDSDNGDTS |
| | HCDR3 | 3 | YRYAMDY |

TABLE 1-continued

3pE Aβ monoclonal antibody sequences

| mAb | Region | SEQ ID NO: | Sequence |
|---|---|---|---|
| | Light Chain | 30 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKLEIKRTVAAPSVFIFPPSDEQLKSGTASWCLLNNFYPREAKVQWKVDNALQSGNSQESVTEQDSKDSTYSLSSTLTLSKADYEKHKVYACEVTHQGLSSPVTKSFNRGEC |
| | VL | 14 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB614 | Heavy Chain | 32 | QVQLVQSGAEVKKPGASVKVSCKASGHVFTSYDMYWVRQAPGQGLEWIGYIDSDNGDTSYNQKFKGRVTLTVDTSTSTVYMELSSLRSEDTAVYYCAYRYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | VH | 16 | QVQLVQSGAEVKKPGASVKVSCKASGHVFTSYDMYWVRQAPGQGLEWIGYIDSDNGDTSYNQKFKGRVTLTVDTSTSTVYMELSSLRSEDTAVYYCAYRYAMDYWGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | YIDSDNGDTS |
| | HCDR3 | 3 | YRYAMDY |
| | Light Chain | 30 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | VL | 14 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB630 | Heavy Chain | 33 | QVQLVQSGAEVKKPGASVKVSCKASGHVFTSYDMYWVKQAPGQSLEWIGYIDSDNGDTSYNQKFKGKVTLTVDTSTSTVYMELSSLRSEDTAVYYCAYRYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | VH | 17 | QVQLVQSGAEVKKPGASVKVSCKASGHVFTSYDMYWVKQAPGQSLEWIGYIDSDNGDTSYNQKFKGKVTLTVDTSTSTVYMELSSLRSEDTAVYYCAYRYAMDYWGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | YIDSDNGDTS |
| | HCDR3 | 3 | YRYAMDY |
| | Light Chain | 34 | DVVMTQSPLSLPVTLGQPASISCKSSQSLLDSRAKTYLTWLLQRPGQSPRRLIYLVSKLDSGVPDRFSGSGSGTDFTLKISRVEAEDVGVYYCWQGTHFPYTFGGGTKLEIKRTVAAPSVFIFPPSDEQLKSGTASVVCLLNNFYPREAKVQWKVDNALQSGNSQESVTEQDSKDSTYSL |

TABLE 1-continued

3pE Aβ monoclonal antibody sequences

| mAb | Region | SEQ ID NO: | Sequence |
|---|---|---|---|
| | | | SSTLTLSKADYEKHKVYACEVTHQGLSSPVTKSFNRGEC |
| | VL | 18 | DVVMTQSPLSLPVTLGQPASISCKSSQSLLDSRAKTYLTWLLQRPGQSPRRLIYLVSKLDSGVPDRFSGSGSGTDFTLKISRVEAEDVGVYYCWQGTHFPYTFGGGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB631 | Heavy Chain | 35 | QVQLVQSGAEVKKPGASVKVSCKASGHVFTSYDMYWVRQAPGQSLEWMGYIDSDNGDTSYNQKFKGRVTLTVDTSTSTVYMELSSLRSEDTAVYYCAYRYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVHWESNGQPENNYKTTPPVLDSDGSFFLYSKLTVDKSRWQQGNVFSCSVMHEALHNHYTQKSLSLSPGK |
| | VH | 19 | QVQLVQSGAEVKKPGASVKVSCKASGHVFTSYDMYWVRQAPGQSLEWMGYIDSDNGDTSYNQKFKGRVTLTVDTSTSTVYMELSSLRSEDTAVYYCAYRYAMDYWGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | YIDSDNGDTS |
| | HCDR3 | 3 | YRYAMDY |
| | Light Chain | 34 | DVVMTQSPLSLPVTLGQPASISCKSSQSLLDSRAKTYLTWLLQRPGQSPRRLIYLVSKLDSGVPDRFSGSGSGTDFTLKISRVEAEDVGVYYCVVQGTHFPYTFGGGTKLEIKRTVAAPSVFIFPPSDEQLKSGTASVVCLLNNFYPREAKVQWKVDNALQSGNSQESVTEQDSKDSTYSLSSTLTTSKADYEKHKVYACEVTHQGLSSPVTKSFNRGEC |

TABLE 1-continued

3pE Aβ monoclonal antibody sequences

| mAb | Region | SEQ ID NO: | Sequence |
|---|---|---|---|
| | VL | 18 | DVVMTQSPLSLPVTLGQPASISCKSSQSLLDSRAKTYLTWLLQRPGQSPRRLIYLVSKLDSGVPDRFSGSGSGTDFTLKISRVEAEDVGVYYCVVQGTHFPYTFGGGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB623 | Heavy Chain | 36 | QVQLVQSGAEVKKPGASVKVSCKASGHVFTSYDMYWVRQAPGQSLEWIGYIDSDNGDTSYNQKFKGKATMTVDTSTSTVYMELSSLRSEDTAVYYCAYRYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | VH | 20 | QVQLVQSGAEVKKPGASVKVSCKASGHVFTSYDMYWVRQAPGQSLEWIGYIDSDNGDTSYNQKFKGKATMTVDTSTSTVYMELSSLRSEDTAVYYCAYRYAMDYWGQGTLVTVSS |
| | HCDR1 Kabat | 1 | SYDMY |
| | HCDR1 AbM | 56 | GHVFTSYDMY |
| | HCDR2 Kabat | 7 | YIDSDNGDTSYNQKFKG |
| | HCDR2 AbM | 57 | YIDSDNGDTS |
| | HCDR3 | 3 | YRYAMDY |
| | Light Chain | 30 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | VL | 14 | DVVMTQSPLSLPVTLGQPASISCKSSQSLLDSRAKTYLTWLQQRPGQSPRRLIYLVSKLD |

TABLE 1-continued

3pE Aβ monoclonal antibody sequences

| mAb | Region | SEQ ID NO: | Sequence |
|---|---|---|---|
| | | | SGVPDRFSGSGSGTDFTLKI<br>SRVEAEDVGVYYCWQGTHFP<br>YTFGGGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB674 | Heavy Chain | 37 | QVQLVQSGAEVKKPGASVKV<br>SCKASGHVFTSYDMYWVRQA<br>PGQGLEWIGYIDSDSGDTSY<br>NQKFKGRVTLTVDTSTSTVY<br>MELSSLRSEDTAVYYCAYYR<br>YAMDYWGQGTLVTVSSASTK<br>GPSVFPLAPSSKSTSGGTAA<br>LGCLVKDYFPEPVTVSWNSG<br>ALTSGVHTFPAVLQSSGLYS<br>LSSVVTVPSSSLGTQTYICN<br>VNHKPSNTKVDKKVEPKSCD<br>KTHTCPPCPAPELLGGPSVF<br>LFPPKPKDTLMISRTPEVTC<br>VVVDVSHEDPEVKFNWYVDG<br>VEVHNAKTKPREEQYNSTYR<br>VVSVLTVLHQDWLNGKEYKC<br>KVSNKALPAPIEKTISKAKG<br>QPREPQVYTLPPSREEMTKN<br>QVSLTCLVKGFYPSDIAVEW<br>ESNGQPENNYKTTPPVLDSD<br>GSFFLYSKLTVDKSRWQQGN<br>VFSCSVMHEALHNHYTQKSL<br>SLSPGK |
| | VH | 21 | QVQLVQSGAEVKKPGASVKV<br>SCKASGHVFTSYDMYWVRQA<br>PGQGLEWIGYIDSDSGDTSY<br>NQKFKGRVTLTVDTSTSTVY<br>MELSSLRSEDTAVYYCAYYR<br>YAMDYWGQGTLVTVSS |
| | HCDR1 Kabat | 1 | SYDMY |
| | HCDR1 AbM | 56 | GHVFTSYDMY |
| | HCDR2 Kabat | 2 | YIDSD**S**GDTSYNQKFKG |
| | HCDR2 AbM | 58 | YIDSD**S**GDTS |
| | HCDR3 | 3 | YRYAMDY |
| | Light Chain | 38 | DVVMTQSPLSLPVTLGQPAS<br>ISCKSSQSLLDSRAKTYLTW<br>LQQRPGQSPRRLIYLVSKLD<br>SGVPDRFSGSGSGTDFTLKI<br>SRVEAEDVGVYYCWQGTHFP<br>YTFGGGTKLEIKRTVAAPSV<br>FIFPPSDEQLKSGTASVVCL<br>LNNFYPREAKVQWKVDNALQ<br>SGNSQESVTEQDSKDSTYSL<br>SSTLTLSKADYEKHKVYACE<br>VTHQGLSSPVTKSFNRGEC |
| | VL | 22 | DVVMTQSPLSLPVTLGQPAS<br>ISCKSSQSLLDSRAKTYLTW<br>LQQRPGQSPRRLIYLVSKLD<br>SGVPDRFSGSGSGTDFTLKI<br>SRVEAEDVGVYYCWQGTHFP<br>YTFGGGTKLEIK |

TABLE 1-continued

3pE Aβ monoclonal antibody sequences

| mAb | Region | SEQ ID NO: | Sequence |
|---|---|---|---|
| | LCDR1 | 4 | KSSQSLLDS**RA**KTYLT |
| | LCDR2 | 5 | LVSKLDS |
| | LCDR3 | 6 | WQGTHFPYT |
| BAMB675 | Heavy Chain | 39 | QVQLVQSGAEVKKPGASVKV<br>SCKASGHVFTSYDMYWVRQA<br>PGQGLEWIGYIDSDSGDTSY<br>NQKFKGRVTLTVDTSTSTVY<br>MELSSLRSEDTAVYYCAYYR<br>YAMDYWGQGTLVTVSSASTK<br>GPSVFPLAPSSKSTSGGTAA<br>LGCLVKDYFPEPVTVSWNSG<br>ALTSGVHTFPAVLQSSGLYS<br>LSSVVTVPSSSLGTQTYICN<br>VNHKPSNTKVDKKVEPKSCD<br>KTHTCPPCPAPELLGGPSVF<br>LFPPKPKDTL**Y**I**T**R**E**PEVTC<br>VVVDVSHEDPEVKFNWYVDG<br>VEVHNAKTKPREEQYNSTYR<br>VVSVLTVLHQDWLNGKEYKC<br>KVSNKALPAPIEKTISKAKG<br>QPREPQVYTLPPSREEMTKN<br>QVSLTCLVKGFYPSDIAVEW<br>ESNGQPENNYKTTPPVLDSD<br>GSFFLYSKLTVDKSRWQQGN<br>VFSCSVMHEALHNHYTQKSL<br>SLSPGK |
| | VH | 21 | QVQLVQSGAEVKKPGASVKV<br>SCKASGHVFTSYDMYWVRQA<br>PGQGLEWIGYIDSDSGDTSY<br>NQKFKGRVTLTVDTSTSTVY<br>MELSSLRSEDTAVYYCAYYR<br>YAMDYWGQGTLVTVSS |
| | HCDR1 Kabat | 1 | SYDMY |
| | HCDR1 AbM | 56 | GHVFTSYDMY |
| | HCDR2 Kabat | 2 | YIDSD**S**GDTSYNQKFKG |
| | HCDR2 AbM | 58 | YIDSD**S**GDTS |
| | HCDR3 | 3 | YRYAMDY |
| | Light Chain | 38 | DVVMTQSPLSLPVTLGQPAS<br>ISCKSSQSLLDSRAKTYLTW<br>LQQRPGQSPRRLIYLVSKLD<br>SGVPDRFSGSGSGTDFTLKI<br>SRVEAEDVGVYYCWQGTHFP<br>YTFGGGTKLEIKRTVAAPSV<br>FIFPPSDEQLKSGTASWCLL<br>NNFYPREAKVQWKVDNALQS<br>GNSQESVTEQDSKDSTYSLS<br>STLTLSKADYEKHKVYACEV<br>THQGLSSPVTKSFNRGEC |
| | VL | 22 | DVVMTQSPLSLPVTLGQPAS<br>ISCKSSQSLLDSRAKTYLTW<br>LQQRPGQSPRRLIYLVSKLD<br>SGVPDRFSGSGSGTDFTLKI<br>SRVEAEDVGVYYCWQGTHFP<br>YTFGGGTKLEIK |
| | LCDR1 | 4 | KSSQSLLDS**RA**KTYLT |
| | LCDR2 | 5 | LVSKLDS |

TABLE 1-continued

3pE Aβ monoclonal antibody sequences

| mAb | Region | SEQ ID NO: | Sequence |
|---|---|---|---|
| | LCDR3 | 6 | WQGTHFPYT |
| BAMB700 | Heavy Chain | 37 | QVQLVQSGAEVKKPGASVKVSCKASGHVFTSYDMYWVRQAPGQGLEWIGYIDSDSGDTSYNQKFKGRVTLTVDTSTSTVYMELSSLRSEDTAVYYCAYYRYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | VH | 21 | QVQLVQSGAEVKKPGASVKVSCKASGHVFTSYDMYWVRQAPGQGLEWTGYIDSDSGDTSYNQKFKGRVTLTVDTSTSTVYMELSSLRSEDTAVYYCAYYRYAMDYWGQGTLVTVSS |
| | HCDR1 Kabat | 1 | SYDMY |
| | HCDR1 AbM | 56 | GHVFTSYDMY |
| | HCDR2 Kabat | 2 | YIDSD**S**GDTSYNQKFKG |
| | HCDR2 AbM | 58 | YIDSD**S**GDTS |
| | HCDR3 | 3 | YRYAMDY |
| | Light Chain | 52 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | VL | 53 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGQGTKLEIK |
| | LCDR1 | 4 | KSSQSLLDS**RA**KTYLT |
| | LCDR2 | 5 | LVSKLDS |
| | LCDR3 | 6 | WQGTHFPYT |
| BAMB701 | Heavy Chain | 39 | QVQLVQSGAEVKKPGASVKVSCKASGHVFTSYDMYWVRQAPGQGLEWIGYIDSDSGDTSYNQKFKGRVTLTVDTSTSTVYMELSSLRSEDTAVYYCAYYRYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTL**Y**I**T**R**E**PEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | VH | 21 | QVQLVQSGAEVKKPGASVKVSCKASGHVFTSYDMYWVRQAPGQGLEWIGYIDSDSGDTSYNQKFKGRVTLTVDTSTSTVYMELSSLRSEDTAVYYCAYYRYAMDYWGQGTLVTVSS |
| | HCDR1 Kabat | 1 | SYDMY |
| | HCDR1 AbM | 56 | GHVFTSYDMY |
| | HCDR2 Kabat | 2 | YIDSD**S**GDTSYNQKFKG |
| | HCDR2 AbM | 58 | YIDSD**S**GDTS |
| | HCDR3 | 3 | YRYAMDY |
| | Light Chain | 54 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | VL | 55 | DVVMTQSPLSLPVTLGQPASISCKSSQSLLDSRAKTYLTWLQQRPGQSPRRLIYLVSKLDSGVPDRFSGSGSGTDFTLKISRVEAEDVGVYYCWQGTHFPYTFGGGTKVEIK |
| | LCDR1 | 4 | KSSQSLLDS**RA**KTYLT |
| | LCDR2 | 5 | LVSKLDS |
| | LCDR3 | 6 | WQGTHFPYT |

The terms "identical" or percent "identity," in the context of two or more nucleic acids or polypeptide sequences (e.g., anti-3pE Aβ antibodies and polynucleotides that encode them, 3pE Aβ polypeptides and 3pE Aβ polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

In Vitro Methods

It is to be understood that all manner of immunoassays employing antibodies or antigen binding fragments thereof are contemplated for use in accordance with the presently preferred embodiments, including assays in which antibodies or antigen binding fragments thereof are bound to solid phases and assays in which antibodies are in liquid media. Methods of immunoassays that can be used to detect analytes using antibodies embodying features of the present invention include, but are not limited to, competitive (reagent limited) assays wherein labeled analyte (analyte analog) and analyte in a sample compete for antibodies and single-site immunometric assays wherein the antibody is labeled; and the like.

The antibodies or antigen binding fragments thereof according to the invention can be used in conventional immunological techniques for the detection of Aβ3pE wherever it can occur, including biological samples for the monitoring of β-amyloid-related diseases and conditioned media from cell culture for monitoring the intracellular processing of APP. Suitable immunological techniques are well known to those skilled in the art and include, for example, ELISA, Western Blot analysis, competitive or sandwich immunoassays and the like, and as is otherwise well known, they all depend on the formation of an antigen-antibody immune complex wherein for the purpose of the assay, the antibody or antigen binding fragment thereof can be detectably labelled with, e.g. radio, enzyme, luminescent or fluorescent labels or it can be immobilized on insoluble carriers. It is thus an object of the invention to provide immunoassays for the determination or detection of Aβ3pE or fragment thereof in a sample, the method comprising contacting the sample with an antibody or antigen binding fragment thereof to Aβ3pE or a fragment thereof according to the invention and determining whether an immune complex is formed between the antibody or antigen binding fragment thereof and the Aβ3pE or fragment thereof. These methods can either be performed on tissue samples or body fluid samples and generally comprise obtaining a sample from the body of a subject; contacting said sample with an imaging effective amount of a detectably labeled antibody or antigen binding fragment thereof according to the invention; and detecting the label to establish the presence of Aβ3pE or fragments thereof in the sample. The measuring methods using the antibodies or antigen binding fragments thereof of the present invention are not particularly limited. Any measuring method can be used as long as the amount of antibodies, antigens, or the antigen-antibody complexes corresponding to the amount of the antigens, in particular the amount of Aβ3pE or fragments thereof in solutions to be measured is detected by chemical or physical means, and calculated from standard curves prepared by the use of standard solutions containing the antigens in known amounts. For example, nephelometry, competitive methods, immunometric methods and sandwich methods are suitably used. With respect to sensitivity and specificity, it is particularly preferred to use sandwich methods.

In the sandwich methods, the test solutions are reacted with an insolubilized antibody, such as insolubilized anti-Aβ3pE antibodies (the first reaction), further, the labeled secondary antibodies are reacted (the second reaction); the activity of the labeling agents on the insolubilized carriers is then assayed, whereby the amount of the Aβ3pE or fragments thereof in the test solutions can be determined. The first reaction and the second reaction can be conducted simultaneously or sequentially.

In measuring methods, labelling substances, radioisotopes, enzymes, fluorescent substances, luminous substances, etc. are used as labelling agents. Examples of the radioisotopes include $^{125}$I, $^{131}$I, $^{3}$H and $^{14}$C. Enzymes are usually made detectable by conjugation of an appropriate substrate that, in turn catalyzes a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Further, the avidin-biotin systems can also be used for labelling the antibodies and immunogens of the present invention. When the immunogens or antibodies are insolubilized, either physical adsorption or chemical binding usually used for insolubilization or fixation of proteins or enzymes can be employed. Examples of the carriers include insoluble polysaccharides such as agarose, dextran, and cellulose, synthetic resins such as polystyrene, polyacrylamide and silicone polymers, and glass.

In a further embodiment for detecting or diagnosing β-amyloid-related diseases, a biological sample including tissue, body fluids, such as cerebrospinal fluid (CSF), blood, plasma, serum, urine, and the like, is contained and contacted with a suitable amount of a first antibody to produce an immune complex. The contact typically involves adding the sample to a solid matrix coated with the first antibody. The complex which results from contacting the sample with the first antibody is separated from the sample by elution. However, other methods of recovery can be employed. The recovered complex is contacted with at least one second antibody directed to an antigenic determinant on the antigen and capable of binding the antigen in the complex. The antigenic determinant to which the second antibody is directed can be the same one as to which the first antibody is directed due to the multiepitopic nature of the antigenic entity. Either the first or the second antibody can be made detectable using any of the labels described above. In a preferred embodiment, the second antibody is made detectable. The presence of the detectable antibody bound to the complex consisting of antigen bound to the first and second antibody can be readily detected using art-known techniques. By comparing the results obtained in the biological sample with those obtained on a control sample, the presence of or levels of altered Aβ3pE or fragments thereof can be determined.

In Vivo Methods

Aspects of the invention relate to a method for preventing, ameliorating, treating and/or decreasing amyloid-beta deposition in amyloid-beta related conditions comprising administration of the antibodies or antigen binding fragments thereof as disclosed herein in a therapeutically effective amount to a subject in need thereof. Additional aspects of the invention include a pharmaceutical composition for preventing, ameliorating, treating and/or decreasing amyloid deposition in amyloid-beta related conditions comprising the antibodies or antigen binding fragments thereof as disclosed herein. Methods of the present invention comprise administering an effective amount of one or more antibodies or antigen binding fragments thereof described herein to a subject in need thereof.

In one aspect, the invention is directed to methods of preventing, ameliorating, treating and/or decreasing amyloid-beta deposition in conditions characterized by the formation of plaques containing beta-amyloid protein in humans, which method comprises administering, preferably peripherally, to a human in need of such treatment a therapeutically or prophylactically effective amount of an antibody according to the invention or an immunologically reactive fragment thereof, which antibody specifically binds to human Aβ3pE. In another aspect, the invention is directed to methods of inhibiting the formation of amyloid plaques and/or methods of clearing amyloid plaques in humans, which method comprises administering to a human subject in need of such inhibition or clearing an effective amount of an antibody according to the invention, wherein the antibody sequesters Aβ3pE peptide in the brain and induces altered Aβ3pE clearance in brain. In additional aspects, the invention is directed to such humanized antibodies, including immunologically effective portions thereof, and to methods for their preparation.

A subject in need thereof is a human suffering or predisposed to suffer from a condition characterized by the formation of plaques containing beta-amyloid protein. In one embodiment, the condition in Alzheimer's disease. In other embodiments, the condition is dementia associated with Trisomy 21 (Down's Syndrome), diffuse Lewy body disease, inclusion body myositis, cerebral amyloid angiopathy or hereditary cerebral hemorrhage with amyloidosis of the Dutch-type (HCHWA-D).

A humanized antibody is an antibody from non-human species whose protein sequences have been modified to increase their similarity to antibody variants produced naturally in humans. Generally, the protein sequence of a humanized antibody is essentially identical to that of a human variant with the exception of the non-human origin of some or all of its complementarity determining regions (CDRs) segments that are responsible for the ability of the antibody to bind to its target antigen. The framework regions of the variable regions are substituted by the corresponding human framework regions leaving the non-human CDR substantially intact. In some cases, humanized antibodies do have a small number of substitutions in one or more of the non-human CDR regions to retain the binding affinity and or dissociation constant of the non-human antibody.

A humanized antibody again refers to an antibody comprising a human framework, at least one CDR from a non-human antibody, and in which any constant region present is substantially identical to a human immunoglobulin constant region, i.e., at least about 85%, 90%, preferably at least 95% identical or 98% identical. Hence, all parts of a humanized antibody, except one or more of the CDRs, are substantially identical to corresponding parts of a human immunoglobulin sequence. For example, a humanized immunoglobulin would typically not encompass a chimeric mouse variable region/human constant region antibody.

Humanized antibodies have at least three potential advantages over non-human and chimeric antibodies for use in human therapy: 1) because the effector portion is human, it can interact better with the other parts of the human immune system (e.g., activate microglia to clear plaques); 2) the human immune system should not recognize the framework or C region of the humanized antibody as foreign, and therefore the antibody response against such an administered antibody should be less than against a totally foreign non-human antibody or a partially foreign chimeric antibody; and 3) administered non-human antibodies have been reported to have a half-life in human circulation that is shorter than the half-life of human antibodies.

In a method to treat and to prevent conditions characterized by the formation of plaques containing beta-amyloid protein, the antibodies or antigen binding fragments thereof (including immunologically reactive fragments) of the invention are administered to a subject at risk for or exhibiting amyloid beta-related symptoms or pathology such as clinical or pre-clinical Alzheimer's disease, dementia associated with Down's syndrome, or clinical or pre-clinical amyloid angiopathy, using standard administration techniques. Preferably, administration is peripherally (i.e. not by administration into the central nervous system) by intravenous, intraperitoneal, subcutaneous, pulmonary, transdermal, intramuscular, intranasal, buccal, sublingual, or suppository administration. Although the antibodies or binding fragments thereof can be administered directly into the ventricular system, spinal fluid, or brain parenchyma, and techniques for addressing these locations are well known in the art, it is not necessary to utilize these more difficult procedures. The antibodies or binding fragments thereof of the invention are effective when administered by the simpler techniques that rely on the peripheral circulation system. The advantages of the present invention include the ability of the antibody or antigen binding fragment thereof to exert its beneficial effects even though not provided directly to the central nervous system itself.

Pharmaceutical compositions for administration are designed to be appropriate for the selected mode of administration, and pharmaceutically acceptable excipients such as dispersing agents, buffers, surfactants, preservatives, solubilizing agents, isotonicity agents, stabilizing agents and the like are used as appropriate. Remington's Pharmaceutical Sciences, Mack Publishing Co., Easton Pa., latest edition, incorporated herein by reference, provides a compendium of formulation techniques as are generally known to practitioners.

It can be particularly useful to alter the solubility characteristics of the antibodies of the invention, making them more lipophilic, for example, by encapsulating them in liposomes or by blocking polar groups.

Peripheral systemic delivery by intravenous, intraperitoneal, or subcutaneous injection is preferred. Suitable vehicles for such injections are straightforward. In addition, however, administration can also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl-N,N,N-trimethylammoniumchloride (DOTMA) or various compounds such as cholesterol hemisuccinate, phosphatidyl glycerols and the like.

The concentration of the humanized antibody in formulations from as low as about 0.1% to as much as about 15 or 20% by weight are selected primarily based on fluid volumes, viscosities, and so forth, in accordance with the particular mode of administration selected. Thus, a typical pharmaceutical composition for injection could be made to contain 1 mL sterile buffered water of phosphate buffered saline and 1-100 mg of the humanized antibody of the present invention. The formulation can be sterile filtered after making the formulation, or otherwise made microbiologically acceptable. A typical composition for intravenous infusion can have a volume as much as 250 mL of fluid, such as sterile Ringer's solution, and 1-100 mg per mL, or more in antibody concentration.

For antibody administration, the dosage ranges from about 0.0001 to 100 mg/kg, and preferably 0.01 to 75 mg/kg, of the host body weight. For example, dosages can be 0.02 mg/kg, 0.25 mg/kg, 0.5 mg/kg, 0.75 mg/kg, 1 mg/kg, 2 mg/kg, 3 mg/kg, 4 mg/kg, 5 mg/kg, 10 mg/kg, 15 mg/kg, 20 mg/kg, 25 mg/kg, 20 mg/kg, 35 mg/kg, 40 mg/kg, 45 mg/kg, 50 mg/kg, 55 mg/kg, 60 mg/kg, 65 mg/kg, 70 mg/kg, or 75 mg/kg of the host body weight. In embodiments, the dosage is within the range of 0.01-10 mg/kg, or within the range of 0.1-15 mg/kg, or within the range of 0.1-20 mg/kg, or within the range of 0.1-30 mg/kg, or within the range of 0.1-40 mg/kg, or within the range of 0.1-50 mg/kg, or within the range of 0.1-60 mg/kg, preferably at least 1 mg/kg, at least 5 mg/kg, at least 10 mg/kg, at least 20 mg/kg, at least 30 mg/kg, at least 40 mg/kg, at least 50 mg/kg or at least 60 mg/kg. In a preferred example, dosages can be about 10 kg/mg, about 20 kg/mg, about 30 kg/mg, about 40 mg/kg, about 50 mg/kg, about 60 mg/kg or about 70 mg/kg. In a particularly preferred example, the antibody is administered intraperitoneally at a dose range from about 0.3 mg/kg to about 60 mg/kg. In an exemplary treatment regime, the antibody is administered intraperitoneally at a dosage about 10 kg/mg, about 20 kg/mg, about 30 kg/mg, about 40 mg/kg, about 50 mg/kg or about 60 mg/kg.

As used herein, the term "about" when referring to a measurable value such as an amount is meant to encompass variations of between ±20% and ±0.1%, preferably ±15% or ±10%, more preferably ±5%, even more preferably ±1%, and still more preferably ±0.5%, ±0.1%. ±0.05% or ±0.01% of the specified value, as such variations are appropriate.

An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to AP in the subject. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals can be required until progression of the disease is reduced or terminated, and preferably until the subject shows partial or complete amelioration of symptoms of disease. Thereafter, a prophylactic regime can be administered.

In some methods, the dosage is administered to achieve a plasma antibody concentration of 1-1000 μg/ml, and in some methods 25-300 μg/ml. Alternatively, antibody can be administered as a sustained release formulation, in which case less frequent administration is required. Dosage and frequency vary depending on the half-life of the antibody in the subject.

Treatment with an antibody of the invention can be a stand-alone treatment. Alternatively, treatment with an antibody of the invention can be one component or phase of a combination therapy regime, in which one or more additional therapeutic agents are also used to treat an individual.

When used for in vivo therapy, the antibodies or antigen binding fragments thereof of the invention are administered to the individual in therapeutically effective amounts, e.g., amounts which reduce, clear or prevent β-amyloid plaques or improve cognitive function in subjects with AD or other β-amyloid-related diseases. The antibodies or antigen binding fragments thereof are administered to an individual, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Agents of the invention can optionally be administered in combination with other agents that are at least partly effective in treatment of amyloidogenic disease. In the case of Alzheimer's and related conditions in which amyloid deposits occur in the brain, antibodies or antigen binding fragments thereof of the invention can be administered in conjunction with other agents that increase passage of the agents of the invention across the blood-brain barrier.

In an embodiment of the invention, antibodies or antigen binding fragments thereof of the invention bind to 3pE Aβ in plaque deposits. By binding to 3pE Aβ in plaque deposits, the antibody or antigen binding fragment thereof can induce plaque removal. Induction of plaque removal can be by activation of microglia around plaques and by destabilizing plaques by removing a stable AP form. Moreover, antibodies or antigen binding fragments thereof of the invention can prevent plaque seeding activity of 3pE Aβ. The possible enrichment of 3pE Aβ in plaque compared to vascular amyloid can increase the therapeutic safety window for immunotherapy.

Kits and Devices

The present invention provides kits and devices that can be used in the above-mentioned methods. Preferably, the kits and devices comprise an antibody or antigen binding fragment thereof that binds to 3pE Aβ. In addition, the kits can comprise reagents and instructional materials. Instructions can be printed, e.g., on paper and/or supplied in an electronically-readable medium. Alternatively, instructions can be provided by directing a user to an internet website, e.g., specified by the manufacturer or distributor of the kit.

Reagents included in kits of the present invention can be supplied in all manner of containers such that the activities of the different components are substantially preserved while the components themselves are not substantially adsorbed or altered by the materials of the container.

In one embodiment, a kit or device comprises an antibody or antigen binding fragment thereof of the invention, preferably a purified antibody, more preferably a monoclonal antibody, even more preferably the isolated monoclonal antibodies that bind to 3pE Aβ peptides. In embodiments, the antibodies are expressed by the hybridoma cells.

Embodiments

Embodiment 1 is an isolated monoclonal antibody or antigen-binding fragment thereof comprising a heavy complementarity determining region 1 (HCDR1), HCDR2, HCDR3, a light chain complementarity determining region 1 (LCDR1), LCDR2, and LCDR3, having the polypeptide sequences of:

a. SEQ ID NOs: 1, 2, 3, 4, 5, and 6, respectively;
b. SEQ ID NOs: 1, 7, 3, 4, 5, and 6, respectively;
c. SEQ ID NOs: 1, 7, 3, 8, 5, and 6, respectively;
d. SEQ ID NOs: 1, 2, 3, 8, 5, and 6, respectively;
e. SEQ ID NOs: 56, 57, 3, 8, 5, and 6, respectively;
f. SEQ ID NOs: 56, 57, 3, 4, 5, and 6, respectively;
g. SEQ ID NOs: 56, 58, 3, 4, 5, and 6, respectively;
h. SEQ ID NOs: 56, 7, 3, 8, 5, and 6, respectively;
i. SEQ ID NOs: 1, 57, 3, 8, 5, and 6, respectively;
j. SEQ ID NOs: 56, 7, 3, 4, 5, and 6, respectively;
k. SEQ ID NOs: 1, 57, 3, 4, 5, and 6, respectively;
l. SEQ ID NOs: 1, 58, 3, 4, 5, and 6, respectively; or
m. SEQ ID NOs: 56, 2, 3, 4, 5, and 6, respectively;

wherein the antibody or antigen-binding fragment thereof specifically binds 3pE Aβ, preferably human 3pE Aβ.

Embodiment 2 is the isolated monoclonal antibody or antigen-binding fragment thereof of embodiment 1, comprising a heavy chain variable region having a polypeptide sequence at least 95% identical to SEQ ID NO:9, 11, 13, 15, 16, 17, 19, 20, or 21, or a light chain variable region having a polypeptide sequence at least 95% identical to SEQ ID NO:10, 12, 14, 18, 22, 53, or 55.

Embodiment 3 is the isolated monoclonal antibody or antigen-binding fragment thereof of embodiment 1, comprising:

a. a heavy chain variable region having the polypeptide sequence of SEQ ID NO:21, and a light chain variable region having the polypeptide sequence of SEQ ID NO:22;
b. a heavy chain variable region having the polypeptide sequence of SEQ ID NO:9, and a light chain variable region having the polypeptide sequence of SEQ ID NO:10;
c. a heavy chain variable region having the polypeptide sequence of SEQ ID NO:11, and a light chain variable region having the polypeptide sequence of SEQ ID NO:12;
d. a heavy chain variable region having the polypeptide sequence of SEQ ID NO:13, and a light chain variable region having the polypeptide sequence of SEQ ID NO:14;
e. a heavy chain variable region having the polypeptide sequence of SEQ ID NO:15, and a light chain variable region having the polypeptide sequence of SEQ ID NO:14;
f. a heavy chain variable region having the polypeptide sequence of SEQ ID NO:16, and a light chain variable region having the polypeptide sequence of SEQ ID NO:14;
g. a heavy chain variable region having the polypeptide sequence of SEQ ID NO:20, and a light chain variable region having the polypeptide sequence of SEQ ID NO:14;
h. a heavy chain variable region having the polypeptide sequence of SEQ ID NO:17, and a light chain variable region having the polypeptide sequence of SEQ ID NO:18;
i. a heavy chain variable region having the polypeptide sequence of SEQ ID NO:19, and a light chain variable region having the polypeptide sequence of SEQ ID NO:18
j. a heavy chain variable region having the polypeptide sequence of SEQ ID NO:21, and a light chain variable region having the polypeptide sequence of SEQ ID NO:53; or
k. a heavy chain variable region having the polypeptide sequence of SEQ ID NO:21, and a light chain variable region having the polypeptide sequence of SEQ ID NO:55.

Embodiment 4 is the isolated monoclonal antibody or antigen-binding fragment thereof of any one of embodiments 1-3, wherein the antibody or antigen-binding fragment thereof is chimeric.

Embodiment 5 is the isolated monoclonal antibody or antigen-binding fragment thereof of any one of embodiments 1-4, wherein the antibody or antigen-binding fragment thereof is human or humanized.

Embodiment 6 is an isolated monoclonal antibody comprising:

a. a heavy chain amino acid sequence comprising SEQ ID NO:37 and a light chain amino acid sequence comprising SEQ ID NO:38;
b. a heavy chain amino acid sequence comprising SEQ ID NO:39 and a light chain amino acid sequence comprising SEQ ID NO:38;
c. a heavy chain amino acid sequence comprising SEQ ID NO:37 and a light chain amino acid sequence comprising SEQ ID NO:52; or
d. a heavy chain amino acid sequence comprising SEQ ID NO:39 and a light chain amino acid sequence comprising SEQ ID NO:54.

Embodiment 7 is an isolated nucleic acid encoding the monoclonal antibody or antigen-binding fragment thereof of any one of embodiments 1-6.

Embodiment 8 is a vector comprising the isolated nucleic acid of embodiment 7.

Embodiment 9 is a host cell comprising the vector of embodiment 8.

Embodiment 10 is a pharmaceutical composition comprising the monoclonal antibody or antigen binding fragment thereof of any one of embodiments 1-6 and a pharmaceutically acceptable carrier.

Embodiment 11 is a method of treating a condition associated the formation of plaques containing beta-amyloid protein in a subject in need thereof, the method comprising administering a monoclonal antibody or antigen binding fragment thereof of any one of embodiments 1-6 or the pharmaceutical composition of embodiment 10 to the subject in need thereof.

Embodiment 12 is the method of embodiment 11 wherein the condition is Alzheimer's disease.

Embodiment 13 is the method of embodiment 11 wherein the condition is selected form the group consisting of dementia associated with Trisomy 21 (Down's Syndrome), diffuse Lewy body disease, inclusion body myositis, cerebral amyloid angiopathy and hereditary cerebral hemorrhage with amyloidosis of the Dutch-type (HCHWA-D).

Embodiment 14 is a method of reducing plaques associated with Alzheimer's disease in a subject in need thereof, the method comprising administering a monoclonal antibody or antigen-binding fragment thereof of any one of embodiments 1-6 or the pharmaceutical composition of embodiment 10 to the subject in need thereof.

Embodiment 15 is a method of preventing seeding activity of 3pE Aβ in a subject in need thereof, the method comprising administering a monoclonal antibody or antigen-binding fragment thereof of any one of embodiments 1-6 or the pharmaceutical composition of embodiment 10 to the subject in need thereof.

Embodiment 16 is a method of producing the monoclonal antibody or antigen-binding fragment thereof of any one of embodiments 1-6, comprising culturing a cell comprising a nucleic acid encoding the monoclonal antibody or antigen-binding fragment thereof under conditions to produce the monoclonal antibody or antigen-binding fragment thereof, and recovering the antibody or antigen-binding fragment thereof.

Embodiment 17 is a method of producing a pharmaceutical composition comprising the monoclonal antibody or antigen-binding fragment thereof of any one of embodiments 1-6, the method comprising combining the monoclonal antibody or antigen-binding fragment thereof with a pharmaceutically acceptable carrier to obtain the pharmaceutical composition.

EXAMPLES

The invention can be further understood in view of the following non-limiting examples.

Example 1: Generation of Monoclonal Antibodies and Humanization Process

Three Balb/c mice (Janvier Labs) were primed with H2N-pEFRHDSGC-COOH (Eurogentec) (SEQ ID NO:47) in complete Freund's adjuvant (Sigma; St. Louis, MO). The peptides were prepared by coupling the peptides via a COOH-terminal cysteine residue to Maleimide Activated Bovine Serum Albumin (Life Technologies; Carlsbad, CA) using commercially available kits such as the Imject Maleimide Activated BSA kit (Pierce; Rockford, IL), according to the manufacturer's instructions. The mice were boosted every two weeks with 100 μg or 200 μg BSA-coupled peptide, first in complete and subsequently in incomplete Freund's adjuvant (Sigma).

Hybridoma and Antibody Production: The mouse showing the highest serum titer was selected for fusion while the spleens of the other mice were isolated and frozen in liquid nitrogen. On day 4, before fusion or spleen extraction, all mice were boosted intraperitoneally with 100 μg of H2N-pEFRHDSGC-COOH (SEQ ID NO:47) coupled to BSA (Merck; Kenilworth, NJ) in saline. Mouse spleen cells were fused with SP2/0 cells (ATCC; Manassas, VA) by a modified procedure of Kohler and Milstein (*Euro. J. Immunol.,* 1976; 292-295). The hybridomas were seeded in 30×96-well plates and screened after 10 days in a direct ELISA on 0.5m/well non-coupled Aβ 3pE-40 peptide (AnaSpec; Fremont, CA). Positive cells were tested for (lack of) cross-reactivity on 0.5 μg/ml coated Aβ1-40 peptide (AnaSpec) and were immediately subcloned.

After fusion, 17 clones reacted as positive in a directly coated ELISA screen with human Aβ3pE-40 synthetic peptide (SEQ ID NO:40) and were frozen in liquid nitrogen.

All hybridomas were grown in Dulbecco's modified Eagle's medium supplemented with 10% fetal calf serum (Hyclone, Europe), Hybridoma Fusion Cloning Supplement (2%) (Roche; Brussels, Belgium), 2% HT (Sigma), 1 mM sodium pyruvate, 2 mM L-glutamine and penicillin (100 U/ml) and streptomycin (50 mg/ml). All products were commercially available and purchased from Life Technologies. Cells were incubated in a humidified 8% CO2 air incubator.

Direct ELISA for Antibody selection: The screening ELISA used for the detection of Aβ 3pE-40 antibodies above was a direct ELISA with 0.5 μg/ml free human Aβ 3pE-40 peptide (SEQ ID NO:40) coated overnight at 4° C. in NUNC Maxisorp (Life Technologies) flat-bottom high-binding 96-well microtiter plates in 50 μl/well coating buffer (10 mM Tris, 10 mM NaCl, and 10 mM $NaN_3$, pH 8.5).

The next day, the plates were blocked with 75 μl/well of 0.1% casein (Merck) in PBS for 60 minutes at room temperature to reduce non-specific binding. Next, 50 μl hybridoma supernatant was added and incubated for 1 hour at 37° C. After washing, the bound monoclonal antibodies were detected with 50 μl/well of sheep-anti-mouse IgG conjugated with horseradish peroxidase (Amersham-Pharmacia Biotech; Little Chalfont, United Kingdom) for 1 hour at 37° C. Both reagents were diluted in 0.1% casein/PBS. The plates were washed and 50 μl of a solution of 0.42 mM 3,5,3',5'-tetramethyl-benzidine (Biorad), 0.003% (vol/vol) $H_2O_2$ (Biorad) in 100 mM citric acid (Biorad; Hercules, CA); 100 mM disodium hydrogen phosphate (pH 4.3) (Biorad) was added as the substrate. The reaction was allowed to proceed for a maximum of 15 minutes on a plate shaker at room temperature, after which the color development was stopped with 2 N H2504 (Merck) 50 μl/well and the plates were read on a microtiter plate reader at 450 nm (Thermomax, Molecular Devices). The cross-reactivity of the selected monoclonal antibodies with full-size human free Aβ 1-40 was tested in a direct ELISA, identical to the screening assay.

From the 17 Aβ3pE-40-reactive clones, BAMB31_1 was selected for further characterization based on affinity and selectivity (cf. Example 2 & 3). This antibody was determined to have a murine IgG1 isotype heavy chain and a murine kappa light chain. Although the murine IgG1 Fc has only 70% sequence identity and 76% sequence similarity to the murine IgG2a Fc, these isotypes have different activities and protein profiles. Compared to murine IgG2a, murine IgG1 has less murine Fc effector and complement function because of weaker binding to murine FcγRI, FcγRIII, and FcγRIV receptors and murine C1q. Considered to be the isotype that is closest to human IgG1 activity, murine IgG2a binds to murine FcγRI, FcγRIII, and FcγRIV receptors and murine C1q thereby having complement, antibody-dependent cellular cytotoxicity (ADCC), and antibody-dependent cellular phagocytosis (ADCP) activity that can contribute to the clearance of Aβ plaques.

The sequence of BAMB31 heavy chain was altered from murine IgG1 to murine IgG2a to create BAMB31_2a. Preservation of reactivity after V-region cloning was confirmed with SPR methods, described below.

Humanization process: The parental antibody BAMB31_2a (mIgG2a) was humanized using a procedure that is similar to Singh, et. al. (MAbs 2015; 7(4):778-91) with the exception of CDR-H2, which was delineated according to the AbM definition (Martin, A. C., PNAS 86: 9268-9277, 1989) for this work. Briefly, complementarity determining regions (CDRs) were identified in the mouse parental sequences. These sequences were compared with human germlines and four human germline heavy chains and two human germline light chain frameworks were selected into which the murine CDRs were grafted. Human J segments for VL and VH of each parental antibody were chosen by comparing the murine and human J segment sequences to maximize sequence identity. A molecular model of the Fv region of the parental mAb was generated in MOE (CCG; Montreal, Canada) using default parameters. The resulting model was graphically examined to identify framework positions that are potentially important for binding and/or antibody stability. Antibody libraries were created in which these positions have human/mouse binary combinations in addition to grafted CDRs. In the libraries, each chain with grafted murine CDRs was paired with the opposite murine parent chain. In this manner, only one chain was adapted to the human framework and back mutations were decided based upon antigen binding. The humanized VH and VL were then combined to arrive at the final candidate antibodies.

The library clones were expressed as Fabs in *E. coli* and tested for binding to the peptide though ELISA and the signals compared against the fully murine parent molecule. Molecule signals exhibiting binding greater than 80% of the murine parent were selected for sequencing. Sequences were analyzed & human adapted heavy chains & human adapted light chains were selected to be combined and expressed as monoclonal human IgG1 antibodies. All VH/VL humanized pairs of each antibody were expressed, purified, and assessed for antigen binding, Epivax in silico immunogenicity risk, number of residues reverted to mouse sequence, and biophysical properties.

Results: Some residues were required to be reverted to mouse sequence to retain binding of the parent. Retention of binding, Epivax in silico immunogenicity risk, and biophysical properties were not dependent on the number of reversions to mouse sequences but on which positions were reverted to mouse sequence. Representative HFA mAb characterization results from this analysis are shown in Tables 2 and 3.

TABLE 2

Examples of BAMB31 HFA Characterization Results

| Sample | Total #Residues Reverted to Mouse Sequence | Epivax V-Region Combined Score | SEC (% Monomer) | KD (M) | Tonset(° C.) | Tm1(° C.) | Tagg(° C.) |
|---|---|---|---|---|---|---|---|
| Range: | **0-7** | **−53.46 to −13.62** | **84-99** | **1.17E−11 to 1.52E−09** | **53.9-62.5** | **60.7-69.1** | **61.7-70.6** |
| BAMB246 | NA | 5.25 | 96 | 1.39E−11 | 60.7 | 67.4 | 69.4 |
| BAMB611 | 0 | −53.46 | 97 | 1.52E−09 | 62.5 | 69.1 | 70.6 |
| BAMB612 | 4 | −20.77 | 98 | 1.17E−11 | 62.1 | 66.7 | 67.6 |
| BAMB613 | 4 | −39.59 | 97 | 1.82E−11 | 59.3 | 65.4 | 66.4 |
| BAMB614 | 3 | −39.77 | 98 | 1.60E−11 | 61.8 | 66.6 | 67.6 |
| BAMB630 | 7 | −13.88 | 98 | 3.83E−11 | 58.4 | 64.6 | 64.7 |
| BAMB631 | 4 | −14.31 | 97 | 1.80E−11 | 58.8 | 64.4 | 65.0 |
| BAMB623 | 5 | −31.47 | 84 | 1.83E−11 | 54.8 | 62.0 | 62.7 |

BAMB246 parent human IgG1 chimera

Values outside of desired range are outlined in bold: Total residues reverted to mouse sequence ≥5; Hc and Lc Epivax risk scores >−10; V region combined Epivax risk scores >−20; SEC % Monomer values <95% kd (1/s) values >1.00E−04; KD (M) values >2.50E−11; Tonset (° C.) <60; Tm1 (° C.) <65; Tagg (° C.) <65

Mitigation of Post Translational Modification Risk: The parent antibody and human framework adapted variants contained an NG post-translational deamidation modification motif in HCDR2. To address this potential issue, individual libraries were created for both the N and G residues using degenerate oligos. These created new sequences introducing all 20 amino acids for each position at random. Each library was screened for retained binding. Variant antibodies exhibiting similar binding to that of the murine parent were selected for sequencing.

Results: After sequencing, both the N to S and N to G mutants had comparable binding to the parent. Lead HFA variants were cloned and expressed as wild type IgG1 (BAMAB674) and an IgG1 with M37Y, S39T, and T41E point mutations in the Fc region (numbering based on Hc constant region Fc IgG1 heavy chain constant region sequence GenBank accession number AEV43323), was designated as the +YTE IgG1 (BAMB675). These mutations are known to increase affinity to FcRn and increase circulating half-life (Properties of Human IgG1s Engineered for Enhanced Binding to the Neonatal Fc Receptor (FcRn), Dall'Acqua W F., JBC, 2006). Characterization of BAMB674 and BAMB675 are shown in Table 3.

TABLE 3

Characterization of BAMB674 and BAMB675

| Properties | BAMB674 | BAMB675 |
|---|---|---|
| Isotype | wt IgG1 | +YTE IgG1 |
| Hc FW | IGHV1-46*03 | IGHV1-46*03 |
| Hc FW positions requiring murine residues | M48I, M70L | M48I, M70L |
| Hc CDR2 NG motif mitigation | N55S | N55S |
| Lc FW | IGKV2-30*01 | IGKV2-30*01 |
| Lc FW position requiring murine residue | V109L | V109L |
| Lc CDR1 NG motif mitigation | NG→RA | NG→RA |
| KD (pM) | 25.4 | 25.7 |
| Tm onset | 62.9° C. | 57.7° C. |
| Tm1 | 67.3° C. | 64.1° C. |
| Tagg | 68.4° C. | 67.7° C. |
| SEC % monomer | 97 | 98 |
| High concentration stable >2 weeks | >100 mg/ml | >100 mg/ml |

TABLE 3a

Thermostability

| Sample | T-onset avg (° C.) | Tm1 avg (° C.) | Tagg avg (° C.) | T-onset ST DEV | Tm1 ST DEV | Tagg ST DEV |
|---|---|---|---|---|---|---|
| Control mAb | 63.8 | 69.8 | 80.6 | 0.092 | 0.016 | 0.001 |
| BAMB700 | 61.4 | 67.4 | 70.5 | 0.228 | 0.178 | 0.168 |
| BAMB701 | 59.1 | 65.2 | 69.5 | 0.263 | 0.155 | 0.559 |
| BAMB674* | 62.9 | 67.3 | 68.4 | — | — | — |

*N = 1

Example 2: Thermal Stability Testing

For BAMB31 human framework adapted variants, their thermal stability was assessed using nano differential scanning fluorimetry (NanoDSF) to measure onset of melting temperature (Tonset), the temperature of first melting transition (Tm1), and the temperature of initial aggregation detection (Tagg). Data for some of the variants is shown in Table 2 (columns 6-8) and Table 3 (rows 10-12) and Table 3a.

Materials and Methods: Thermal stability of a sample is determined using an automated Prometheus instrument. Measurements are made by loading sample into 24 well capillary from a 384 well sample plate. Duplicate runs are performed for each sample. Prometheus NanoDSF user interface (Melting Scan tab) is used to set up the experimental parameters for the run. The thermal scans for a typical IgG sample span from 20° C. to 95° C. at a rate of 1.0° C./minute. The typical concentration of samples range between 0.3 to 1 mg/mL. The intrinsic fluorescence of the molecule at 330 and 350 nm is used to monitor unfolding during temperature ramp and recorded as changes in fluorescence intensity over time. This is called as thermal scan results (Tm). In parallel, using back-reflection technology, the instrument calculates the on-set of aggregation (Tagg) during thermal ramp. Thus, the NanoDSF method enables simultaneous measure of conformational and colloidal stability of lead candidates that are often monitored as indicators for long-term sample stability under varying conditions.

Example 3: Epivax in Silico Immunogenicity Risk Assessment

The EpiMatrix software (EpiVax Inc.) for predicting MHC class II binding was used to perform an in-silico analysis of anti-Aβ 3pE mabs V regions. The software examines consecutive amino acid 9-mers to identify potential HLA class II binding sequences. The database includes the most common HLA types covering approximately 95% of the human population. If the HLA receptor of an antigen presenting cell binds a peptide agretope, then the other face of that peptide (the epitope) can bind T effector or T regulatory cells, which in turn can lead to stimulation or suppression of an immune response against the protein bearing that epitope. The software generates an agretope binding score that can be adjusted for predicted T regulatory cell binding. Scores are normalized relative to the size of the protein and the number of binding events leading to an output indicating the predicted immunogenicity of the protein.

Example 4: Analytical Characterization of Purified Mabs

The protein concentration for each purified mAb was determined by measuring the absorbance at 280 nm on a NanoDrop1000 spectrophotometer or Trinean DropSense96 multichannel spectrophotometer and calculated using the extinction coefficient based on the amino acid sequence.

SE HPLC of the purified antibodies was performed by running samples on a TOSOH TSKgel BioAssist G3 SWxl column, in 0.2 M Na Phosphate pH 6.8 at 1 mL/min on a Waters Alliance HPLC for 20 min. The column effluent was monitored by absorbance at 280 nm. Results are shown in Tables 2 and 3.

Example 5: Binding Kinetics and Affinity Measurements

Surface Plasmon Resonance (SPR) is a label-free detection method used to investigate biomolecular interactions.

Monitoring small changes in mass on a sensor surface, this direct real-time binding assay provides qualitative and quantitative data about the interaction between biomolecules; i.e. determination of equilibrium binding constant (affinity, $K_D$) and kinetic rate constants ($k_a/k_d$; rate of complex association $k_a$, and rate of complex dissociation $k_d$). This method is useful in studies of protein-protein and protein-nucleic acid interactions, as well as interactions between proteins and small molecules. Here, interactions between 3pE-specific antibodies and human Aβ3pE-40 (SEQ ID NO:40) or Aβ3pE-28 (SEQ ID NO:42), human Aβ1-40 (SEQ ID NO:41) or Aβ1-28 (SEQ ID NO:43), and rodent Aβ3pE-28 peptides (SEQ ID Nos:45 and 46) were investigated.

Materials and Methods

SPR: A mouse antibody capture kit from GE Healthcare was used for the affinity study of BAMB31_2a (mIgG2a) against the Aβ-3pE-40 peptide (SEQ ID NO:40). J&JPRD/Aβ/pE3/1 mIgG2a (described in US Patent Publication No. 2018/0142011) and mE8c mIgG2a (described in U.S. Pat. Nos. 9,944,696 and 8,679,498) were included as control antibodies. Immobilization of the anti-mouse antibody was performed via amine coupling on a CM5 sensor chip following the manufacturer's protocol. Subsequently, the antibody of interest (1 μg/ml) was captured by the anti-mouse antibody to a level of 300 RU, followed by injection of human Aβ 3pE-40 peptide (SEQ ID NO:40) at various concentrations (3.125 nM, 6.25 nM, 12.5 nM, 25 nM and 50 nM) diluted in running buffer (20 mM phosphate buffer with 2.7 mM KCl, 137 mM NaCl and 0.05% surfactant P20 (Tween™ 20)). The surface was regenerated with 10 mM glycine HCl at pH 1.7 for at least 180 sec and additional 60 sec. Human Aβ (1-40) peptide (SEQ ID NO:41) was used as a negative control.

Affinity measurements were performed using an optical biosensor T200 (Biacore®). Kinetic analysis was performed according to 1:1 binding fitting model with Biacore T200 Evaluation Software (version 2.0).

In some instances, binding affinities and specificity of anti-Aβ 3pE mAbs were measured by SPR performed using different instruments (Biacore T200, Biacore 8K or MASS-2 (Biacore, Inc.)) and anti-human or anti-mouse immunoglobulin biosensor surfaces. Anti-human or anti-mouse immunoglobulin antibodies were covalently coupled to the surface of CM4 or CM5 sensor chips (GE Healthcare) using manufacturer instructions for amine-coupling chemistry. Antibodies of interest were captured on the anti-human or mouse immunoglobulin sensor chip to a level of 300-400 RU, followed by injection of Aβ peptides or proteins (examples: human Aβ 3pE-40 (SEQ ID NO:40), Aβ 3pE-28 (SEQ ID NO:42), scrambled Aβ 3pE-28 (SEQ ID NO:44), Aβ 1-28 (SEQ ID NO:43), mouse Aβ 3pE-28 (SEQ ID NO:46), or Fibronectin) at various concentrations in HEPES Buffered Saline containing 0.005% surfactant P20 (Tween™ 20). The surface was regenerated with 2 pulses injections of 30 μL of 10 mM Gly pH1.5 at 100 μL/min. Data reported is the difference in SPR signal between the flow cell containing the captured antibody and a reference cell without captured antibody. Additional instrumental contributions to the signal were removed by subtraction of the data from the blank injection from the reference-subtracted signal. When applicable data were analyzed by fitting association and dissociation phases at all concentrations (global fit) with a 1:1 binding model using the Biaevaluation software (Biacore, Inc.). Otherwise the data was evaluated qualitatively for YES/NO binding.

Immunohistochemistry on formalin fixed paraffin embedded brain: For immunohistochemistry analysis, following deparaffinization and rehydration of the sections, antigen retrieval was performed by incubating transgenic mouse brain slides during 10 minutes in formic acid (70% in distilled water) and endogenous peroxidase activity was blocked with 3% hydrogen peroxide (DAKO; Glostrup, Denmark, S2023). Sections were incubated 1 hour with BAMB674, BAMB675, hE8L, R17L, R17, CI-C7, B12L, antibody I or antibody II (the latter seven antibodies were previously described in U.S. Pat. No. 9,944,696B2 and U.S. Pat. No. 8,679,498B2) at different concentrations (working concentration: 2, 0.1-0.05-0.025 μg/ml) in antibody diluent with background reducing components (DAKO, S3022)). After extensive washing, HRP-labelled anti-human secondary antibody (PI-3000, Vector labs; Burlingame, CA —1/500 in antibody diluent (DAKO, S0809)) was applied to the slides for 1 hour, followed by chromogenic labelling with 3,3-diaminobenzidine (DAB) (DAKO, K3468). Slides were counterstained with hematoxylin, dehydrated and permanently mounted with Vectamount (H-5000, Vector Labs).

Figure 1:
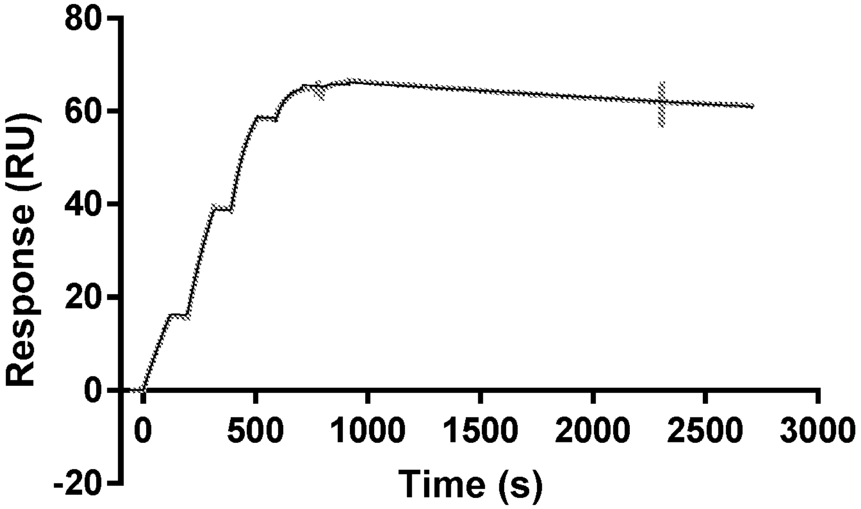
FIG. 1 is a sensogram (single cycle kinetics) from surface plasmon resonance label-free detection of the affinity binding interaction of BAMB31_2a (mIgG2a) to human Aβ(3pE-40) peptide. Grey traces represent the double-reference subtracted data, while the black traces represent the fitted values.
Figure 2:
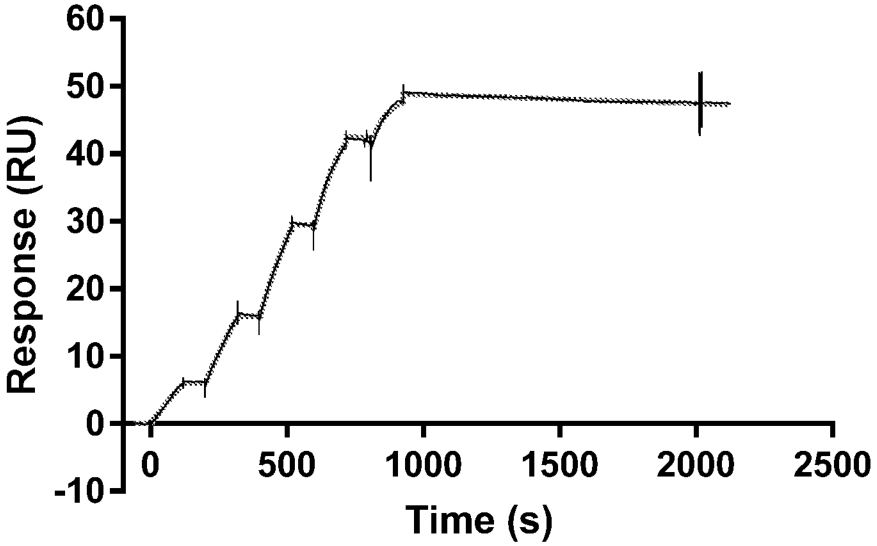
FIG. 2 is a sensorgram (single cycle kinetics) from surface plasmon resonance label-free detection of the affinity binding interaction of mE8c mIgG2a to human Aβ(3pE-40)
Figure 3A:
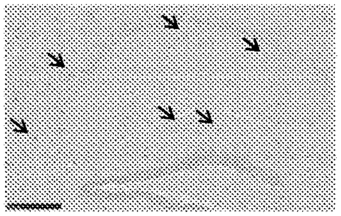
Figure 3B:
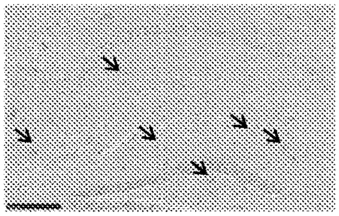
Figure 3C:
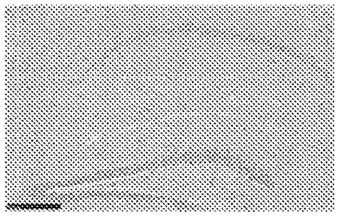
Figure 3D:
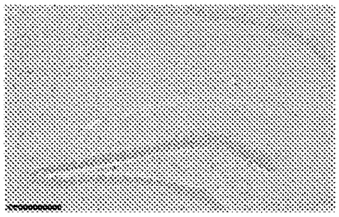
Figure 3E:
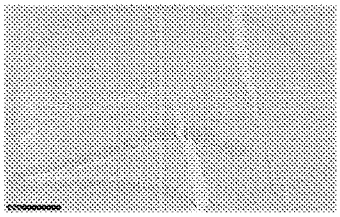
Figure 3F:
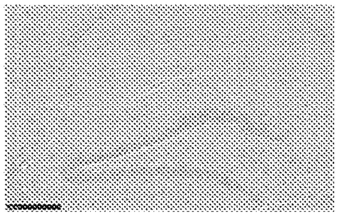
Figure 3G:
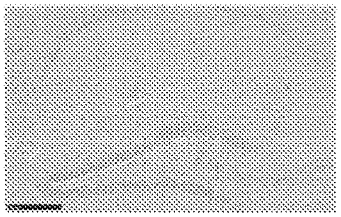
Figure 3H:
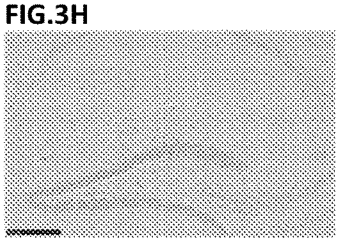
Figure 3I:
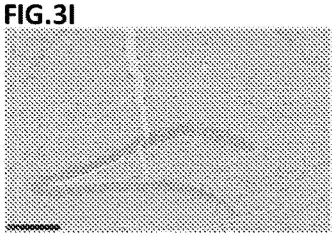

Results: Kinetic analysis of monoclonal antibody BAMB31_2a (mIgG2a) confirmed affinity binding to Aβ3pE-40 peptide (SEQ ID NO:40). No binding was detected when applying human Aβ1-40 peptide (SEQ ID NO:41) at concentrations up to 50 nM. Sensorgram (single cycle kinetics) demonstrating binding interactions of BAMB31_2a (mIgG2a) to human Aβ3pE-40 peptide (SEQ ID NO:40) is illustrated in FIG. 1. As comparator molecules, J&JPRD/Aβ/pE3/1 mIgG2a and mE8c mIgG2a (FIG. 2) were evaluated in the same assay and higher affinity of BAMB31 compared to mE8c and J&JPRD/Aβ/pE3/1 was demonstrated. Equilibrium binding constant (affinity, $K_D$) and kinetic rate constants ($k_a/k_d$) are shown in Table 4.

TABLE 4

Kinetics of J&JPRD/Aβ/pE3/1, BAMB31 and mE8c mIgGa

| Sample | | ka (1/Ms) | kd (1/s) | $K_D$ (pM) |
|---|---|---|---|---|
| J&JPRD/Aβ/pE3/1 | Mean | 1.12E+05 | 9.37E−05 | 853 |
| (mIgG2a) | SD | 1.48E+04 | 1.53E−05 | 201 |
| BAMB31 (mIgG2a) | Mean | 9.30E+05 | 4.94E−05 | 53 |
| | SD | 6.01E+03 | 3.97E−06 | 5 |
| mE8c | Mean | 3.36E+05 | 3.20E−05 | 96 |
| (mIgG2a) | SD | 1.05E+04 | 7.27E−06 | 25 |

Kinetic analysis of BAMB31 HFA mAbs (BAMB674 and BAMB675), with the Hc CDR2 NG deamidation risk mitigated, showed retained binding affinity to Aβ3pE-28 peptide (SEQ ID NO:42) relative to the BAMB31_2a (mIgG2a) parent and the BAMB246 (human IgG1 chimera) parent. Equilibrium binding constant (affinity, $K_D$) and kinetic rate constants ($k_a/k_d$) are shown in Table 5.

Compared to earlier described humanized 3pE-specific antibodies hE8L, R17L, R17, CI-C7, B12L, antibody I and antibody II (previously described in U.S. Pat. No. 9,944,696B2 and U.S. Pat. No. 8,679,498B2), affinities of the current BAMB31 HFA molecules are higher, as shown in Table 5.

TABLE 5

3pE Aβ Binding Kinetics of BAMB31 HFA and mE8c HFA molecules

| Sample | N | ka (1/Ms) | M (1/s) | $K_D$ (pM) |
|---|---|---|---|---|
| BAMB675 | 9 | 3.24E+06 | 8.24E−05 | 25.7 |
| BAMB674 | 9 | 3.27E+06 | 8.32E−05 | 25.4 |
| BAMB246 (human chimeric parent) | 9 | 3.53E+06 | 4.42E−05 | 12.6 |
| BAMB31_2a (mIgG2a parent) | 1 | 2.89E+06 | 7.97E−05 | 27.5 |

TABLE 5-continued

3pE Aβ Binding Kinetics of BAMB31 HFA and mE8c HFA molecules

| Sample | N | ka (1/Ms) | M (1/s) | $K_D$ (pM) |
|---|---|---|---|---|
| Antibody I | 5 | 9.86E+05 | 1.84E−04 | 228.0 |
| Antibody II | 5 | 1.43E+06 | 1.02E−04 | 82.0 |
| B12L | 1 | 2.81E+05 | 1.25E−04 | 445.0 |
| C1-C7 | 2 | 1.46E+05 | 2.63E−04 | 1810 |
| hE8L | 2 | 5.07E+05 | 6.36E−05 | 127.0 |
| R17L | 2 | 3.21E+05 | 3.31E−04 | 1030 |
| R17 | 2 | 1.28E+05 | 7.43E−04 | 5800 |
| Human chimeric mE8c | 4 | 7.02E+05 | ≤6.44e−5 | ≤78.0 |
| mE8c mIgG2a parent | 4 | 7.25E+05 | ≤6.46e−5 | ≤89.0 |

Human chimeric antibodies have the mouse variable regions on a human IgG1 constant region.

TABLE 5a

Comparison of Binding Affinity

| Sample | ka (1/Ms) | kd (1/s) | $K_D$ (M) |
|---|---|---|---|
| BAMB700 | 2.88E+06 | 9.86E−06 | 3.42E−11 |
| BAMB701 | 3.01E+06 | 9.47E−05 | 3.14E−11 |
| BAMB674 | 3.39E+06 | 1.36E−04 | 4.01E−11 |
| BAMB675 | 3.74E+06 | 1.66E−04 | 4.43E−11 |
| Control mAb | 4.11E+06 | 1.56E−04 | 3.79E−11 |

4U-3pE-beta-Amyloid Conc range 0.6 to 4.5 nM

Higher affinity as measured by SPR also translated to improved plaque binding. A dilution series of primary antibodies by immunohistochemistry on brain sections of transgenic mouse brain was performed. All the antibodies give visible plaque labelling at 2 μg/mL, although to different extents. At a concentration of 0.1 μg/mL, antibodies CI-C7 and R17L did not yield visible plaque labelling, in accordance with low affinity as measured by SPR. At a concentration of 0.05 μg/mL, BAMB674 and BAMB675 demonstrate plaque labelling, while plaque labelling is visually absent at this concentration for the comparator molecules (FIG. 3). At a concentration of 0.025 μg/mL, visible plaque labelling is (almost completely) absent for all molecules tested.

In conclusion, immunohistochemistry data confirm SPR data demonstrating higher affinity of BAMB674 and BAMB675 versus comparator molecules.

The BAMB246 (human IgG1 chimera) and current BAMB31 HFA mAbs (BAMB674 and BAMB675) had >3 logs of selectivity over highly homologous mouse Aβ 3pE-28 peptide (SEQ ID NO:46), and >5 logs of selectivity over fibronectin, Aβ 1-28 peptide (SEQ ID NO:43), and Aβ 3pE-28 peptide with amino acids 3-9 scrambled (scrambled 3pE-28) (SEQ ID NO:44). Selectivity results and equilibrium binding constant (affinity, $K_D$) and kinetic rate constants ($k_a$ and $k_d$) for related peptides and protein are shown in Table 6.

TABLE 6

Selective Binding Kinetics of BAMB246 (human IgG1chimera) and HFA mAbs to Related Targets

| Sample | Peptide/Protein | ka (1/Ms) | kA (1/s) | $K_D$ (M) | Fold Selectivity |
|---|---|---|---|---|---|
| BAMB246 | mouse Aβ 3pE-28 | 1.02E+04 | 4.04E−04 | 3.96E−08 | 3143 |
| | fibronectin | no binding up to | 1.2 uM | >1.20E−06 | >95000 |
| | human Aβ 1-28 | no binding up to | 1.2 uM | >1.20E−06 | >95000 |
| | Scrambled 3pE-28 | no binding up to | 1.2 uM | >1.20E−06 | >95000 |
| BAMB674 | mouse Aβ 3pE-28 | 7.40E+03 | 3.38E−04 | 4.55E−08 | 1791 |
| | fibronectin | no binding up to | 1.2 uM | >1.20E−06 | >47000 |
| | human Aβ 1-28 | no binding up to | 1.2 uM | >1.20E−06 | >47000 |
| | Scrambled 3pE-28 | no binding up to | 1.2 uM | >1.20E−06 | >47000 |
| BAMB675 | mouse Aβ 3pE-28 | 4.68E+03 | 3.33E−04 | 7.75E−08 | 3014 |
| | fibronectin | no binding up to | 1.2 uM | >1.20E−06 | >46000 |
| | human Aβ 1-28 | no binding up to | 1.2 uM | >1.20E−06 | >46000 |
| | Scrambled 3pE-28 | no binding up to | 1.2 uM | >1.20E−06 | >46000 |

Scrambled 3pE-28 is the human Aβ 3pE-28 peptide with amino acids 3-9 scrambled.

Fold selectivity was determined by dividing the KD in Table 4 by the KD in Table 3.

≥1.20E−06 $K_D$ (M) had no binding of antigen detected up to the maximum 1.2 μM concentration tested.

FcRn Binding affinities for a BAMB31 HFA antibody on a wild type IgG1 (BAMB674) and a +YTE IgG1 isotype (BAMB675) are shown in Table 7. The +YTE mAb (BAMB675) is ~3-fold higher in affinity for human and cynomolgus FcRn compared with wt IgG1 (BAMB674), which translated into a longer circulating half-life of the +YTE antibody in a cynomolgus monkey pharmacokinetic study (FIG. 11.)

TABLE 7

FcRn Binding Affinities Comparing HFA mAb as a Wild Type and +YTE IgG1

| Sample | FcRn | $K_d$(M) |
|---|---|---|
| IgG1 control | human | 4.43E−07 |
| IgG1 control | cyno | 4.30E−07 |
| BAMB674 | human | 3.49E−07 |
| BAMB674 | cyno | 2.68E−07 |
| BAMB675 | human | 1.11E−07 |
| BAMB675 | cyno | 8.64E−08 |

KD (M) values were averaged from 5-6 independant replicates.

Example 6: Sandwich ELISA for Cross-Reactivity Testing

For the selected Aβ3pE monoclonal antibody BAMB31, the cross-reactivity with rodent Aβ3pE-40 (SEQ ID NO:45) and human Aβ1-40 (SEQ ID NO:41), Aβ1-42 (SEQ ID NO:48), Aβ11pE-40 (SEQ ID NO:49) and Aβ11pE-42 (SEQ ID NO:50) was evaluated using synthetic peptides. The combination BAMB31+JRF/cAβ40/28-HRPO was used to investigate the cross-reactivity with Aβ1-40 (SEQ ID NO:41), Aβ11pE-40 (SEQ ID NO:49) and rodent Aβ3pE-40 (SEQ ID NO:45), and the combination BAMB31+JRF/cAβ42/26-HRPO was used to investigate the cross-reactivity with Aβ1-42 (SEQ ID NO:48) and Aβ11pE-42 (SEQ ID NO:50). Concentrations up to 10,000 pg/mL were tested.

Materials and Methods: Standards were dissolved in dimethylsulphoxide (DMSO) (Sigma) at 0.1 mg/mL and stored at −80° C. For use in ELISA, peptides were further diluted in 0.1% casein in PBS down to 1 pg/mL. Ninety-six-well-plates (Maxisorb ELISA plates; NUNC) were coated overnight at 4° C. with monoclonal antibodies from BAMB31_1 at a concentration of 1.5 μg/mL in coating buffer. The next day, plates were washed and blocked with 0.1% casein in PBS for 1-4 hours at room temperature. Standards were incubated overnight at 4° C. together with HRPO-labeled secondary antibody (JRF/cAβ40/28-HRPO or JRF/cAβ42/26-HRPO). After overnight incubation, the plates were washed, and the assay was developed with TMB peroxide EIA substrate kit (Biorad) according to the manufacturer's recommendations.

Results: BAMB31 was shown to have selective binding to Aβ3pE-40 (SEQ ID NO:40) and Aβ3pE-42 (SEQ ID NO:51), and no detectable crossreactivity to human Aβ1-40 (SEQ ID NO:41), human Aβ1-42 (SEQ ID NO:48) and rodent Aβ3pE-40 (SEQ ID NO:45) and human AβpE11-40 (SEQ ID NO:49) and AβpE11-42 (SEQ ID NO:50) at concentrations up to 10 ng/mL (FIG. 4).

Example 7: Immunohistochemistry for Testing Antibody Reactivity to Plaques in Transgenic Mouse and Human AD Brain Tissue Reactivity of antibodies to plaques was investigated both in formalin-fixed, paraffin-embedded (FFPE), as well as cryopreserved brain tissue.

Materials and Methods

Formalin fixed paraffin embedded brain: For immunohistochemistry analysis, following deparaffinization and rehydration of the sections, antigen retrieval was performed by incubating transgenic mouse brain slides during 10 minutes in formic acid (70% in distilled water) and endogenous peroxidase activity was blocked with 3% hydrogen peroxide (DAKO, Glostrup, Denmark, S2023). Sections were incubated 1 hour with BAMB246 (huIgG1 chimera), BAMB674 or BAMB675 (working concentration: 4 μg/ml in antibody diluent with background reducing components (DAKO, S3022)). After extensive washing, HRP-labelled anti-human secondary antibody (PI-3000, Vector labs—1/500 in antibody diluent (DAKO, S0809)) was applied to the slides for 1 hour, followed by chromogenic labelling with 3,3-diaminobenzidine (DAB) (DAKO, K3468). Slides were counterstained with hematoxylin, dehydrated, and permanently mounted with Vectamount (H-5000, Vector Labs).

Cryopreserved brain: Human brain samples were snap-frozen, sliced with a cryostat (20 μm thickness) and stored at −80° C. before use. Sections were dried at room temperature, followed by formalin fixation, blocking of endogenous peroxidase with 3% hydrogen peroxide (DAKO, Glostrup, Denmark, 52023) and 1 hour blocking in PBS1×+0.3% Triton X-100 and 10% normal goat serum (DAKO, X0907). Primary antibody pE3/16 (2 μg/ml in antibody diluent with background reducing components (DAKO, S3022)) was applied to the sections for 1 hour. After extensive washing, slides were incubated with HRP-conjugated anti-mouse secondary antibody (Envision, DAKO, K4000), followed by chromogenic DAB labelling (DAKO, K3468). Slides were counterstained with hematoxylin, dehydrated and mounted with organic mounting medium (Vectamount, Vector labs). Imaging was performed with a Hamamatsu Nanozoomer (Hamamatsu Photonics; Shizuoka, Japan).

Results: Reactivity of BAMB264 (human IgG1 chimera) as well as BAMB674 and BAMB675 was demonstrated on FFPE tissue of transgenic mice (FIGS. 5A-5F). Moreover, BAMB31_2a (mIgG2a) demonstrated substantial plaque labelling in cryopreserved AD brain tissue (FIG. 6). A substantial fraction of plaques detected by antibody 4G8 are also labelled with BAMB31 in cryosections of human brain (FIGS. 5A-5F). ++

Example 8: Serum Antibody Levels after Dosing in Transgenic Mice

Serum antibody levels after treatment with BAMB31 and comparator molecule mE8c were investigated.

Material and methods: Aged transgenic mice expressing elevated levels of human Aβ42 and Aβ40 peptides (22-23 months old) received a single intraperitoneal (i.p.) injection of 20 mg/kg mE8c mIgG2a, BAMB31_2a (mIgG2a) or isotype control antibody mIgG2a (n=5 per treatment group). Following antibody dosing, whole blood was collected at intermediate timepoints (24 and 48 hours post-injection) via the Vena saphena magna and via orbital puncture at sacrifice (day 4 post-injection) in MICROVETTE® collection tubes (100Z and 300Z respectively; Sarstedt; Numbrecht, Germany). Collected whole blood was incubated at room temperature for 1-2 hours and subsequently centrifuged at 10,000 rpm for 10 minutes at 4° C. to isolate the serum from the blood clot. Serum antibody levels were determined using an allotype-specific enzyme-linked immunosorbent assay (ELISA). For this, Nunc MaxiSorp™ flat-bottom plates (Thermo Scientific; Waltham, MA) were coated overnight with 1.5 μg/ml mouse monoclonal anti-IgG2a(a) (BD Biosciences; San Jose, CA) at room temperature. Antibody standards of mE8c mIgG2a, BAMB31_2a (mIgG2a), and isotype control mIgG2a were prepared individually at 1 μg/ml in block buffer (1% BSA in PBS buffer+0.05% Tween-20) and further diluted down to 0.1 ng/ml in block buffer. After washing (PBS buffer+0.05% Tween-20), samples were blocked with block buffer for 1 hour at room temperature. Next, standards and prediluted serum samples were incubated in coated MAXISORP™ plates for 1 hour at room temperature. Following sample incubation, plates were washed and incubated with a Peroxidase-AffiniPure goat anti-mouse IgG (Fcy Subclass 2a specific) antibody for 1 hour at room temperature. Plates were washed and developed by adding TMB Peroxidase EIA substrate kit (1-step, Pierce) to the wells. Color development was stopped after 2 minutes by adding 2N H2504 to the wells and plates were read at 450 nm using an EnVision multimode plate reader (Perkin Elmer).

Results: Serum antibody levels were measured 24 hours, 48 hours and 4 days after intraperitoneal injection of 20 mg/kg of antibody. Mean antibody concentrations in serum were comparable after 24 hours for all antibodies investigated. For BAMB31_2a and the isotype control antibody, a decrease in antibody concentrations occurred gradually over time (up to approximately 30% decrease on day 4), while a clearly higher decrease over time could be observed for mE8c with a decrease of approximately 97% on day 4 (FIG. 7).

In conclusion, a difference in pharmacokinetic profiles after i.p. injection with BAMB31_2a and mE8c in a plaque-depositing mouse model was shown, indicating a slower clearance after treatment with BAMB31_2a antibody compared to mE8c.

Example 9: Chronic Efficacy Studies in Transgenic Mouse Models

Efficacy for reducing amyloid burden as well as the effect on microhemorrhages after chronic treatment with BAMB31_2a mIgG2a was investigated in a transgenic mouse model.

Material and methods: PDAPP (V717F) transgenic mice (mean age 18.3 months at study start) were treated with weekly i.p. doses of 30 mg/kg of BAMB31_2a antibodies (mIgG2a) for 12 weeks. A control group receiving mIgG2a isotype control antibody injection was included in the experiment. Animals were euthanized on day 7 after the final i.p. injection (mean age 21.1 months old at study end). Mice received perfusion with PBS prior to issue collection. The left hemisphere (fraction 1: hippocampus, fraction 2: rest brain without hippocampus/cerebellum/brain stem) was cryopreserved for further biochemistry analysis, while the right hemisphere was fixed overnight in a formalin-based fixative, followed by paraffin embedding and slicing (5 μm) with a microtome.

To evaluate effect on amyloid burden after chronic treatment, both biochemical and immunohistochemical analysis was performed. For biochemical analysis, brains were homogenized in ice-cold 5 M guanidin-HCl and 50 mM Tris/HCl extraction buffer (100 mg tissue/ml extraction buffer) utilizing Tallprep D lysing matrix tubes (MP Bio). After homogenization, samples were placed in an end-over-end rotation wheel for 3 hours at room temperature. The resulting homogenates were stored at −80° C. prior to analysis with MSD sandwich immunoassays.

Synthetic Aβ peptide standards were dissolved in dimethylsulphoxide (DMSO) (Sigma) at 0.1 mg/mL and stored at −80° C. For use in MSD immunoassays, peptides were further diluted in 0.5 M GuHCl+5 mM Tris-HCl—pH 8.0 (10-fold dilution of extraction buffer in 0.1% casein in PBS). GuHCl extracts were thawed and diluted 1:10 in ice-cold 0.1% casein in PBS and centrifuged at 20,000 g for 20 minutes at 4° C. Supernatant was recovered for use in sandwich MSD assays, with further sample dilutions in 0.5 M GuHCl+5 mM Tris-HCl—pH 8.0 (10-fold dilution of extraction buffer in 0.1% casein in PBS).

96-well sector plates standard (Meso Scale Discovery; Rockville, MD) were coated overnight at 4° C. with monoclonal antibodies at a concentration of 1.5 μg/mL in PBS. The next day, plates were washed and blocked with 0.1% casein in PBS for 2 hours at room temperature. Standards and samples were incubated overnight at 4° C. with biotin-labeled secondary antibody. After overnight incubation, plates were washed and incubated with secondary detection reagent (Streptavidin—SULFO-TAG™ labelled) for 2 hours at room temperature. Plates were washed and 2× Read Buffer T was added after which the plates were read according to the manufacturer's recommendations. Aβ concentrations were determined using a standard curve with a four-parameter logistic model with $1/Y^2$ weighting function.

The combination JRF/AβN/25+4G8-biotin antibodies were used to investigate Aβ1-x concentrations in brain homogenates.

For immunohistochemistry analysis, following deparaffinization and rehydration of the sections, antigen retrieval was performed by incubating slides during 10 minutes in formic acid (70% in distilled water) and endogenous peroxidase activity was blocked with 3% hydrogen peroxide (DAKO, Glostrup, Denmark, S2023). Sections were incubated overnight with biotinylated 4G8 antibody (Biolegend; San Diego, CA), diluted 1/2000 in antibody diluent with background reducing components (DAKO, S3022). After extensive washing, streptavidin-HRP (PK6100 Elite, Vector labs) was applied to the slides for 30 minutes, followed by chromogenic labelling with 3,3-diaminobenzidine (DAB) (DAKO, K3468). Slides were counterstained with hematoxylin, dehydrated and permanently mounted with Vectamount (H-5000, Vector Labs). Images (20×) were generated with a NanoZoomer slide scanner (Hamamatsu Photonics) and analyzed with Matlab/Phaedra. Regions-of-interest (ROIs) were manually delineated in accordance with the Franklin and Paxinos atlas (Franklin K B, Paxinos G. Mouse brain in stereotaxic coordinates. Waltham: Academic Press; 1997) and for each ROI the percentage of DAB-labelled area per total area was calculated.

To evaluate effect on microhemorrhages, Perls' staining was performed. Briefly, paraffin embedded tissue sections were treated with acidic ferrocyanide solution according to the protocol described below. Ferric ion ($Fe^{3+}$) present in micro-bleedings will combine with ferrocyanide resulting in the formation of a blue pigment called Prussian blue. After deparaffinization and rehydration, sections were incubated 30 minutes in a 1/1 mixture of 2% potassium ferrocyanide (Sigma-Aldrich) and 2% glacial hydrochloric acid (Sigma-Aldrich). After rinsing the slides three times in distilled water, counterstaining was performed with nuclear fast red (Sigma-Aldrich), followed by rinsing in distilled water, dehydration, and mounting (Vectamount, Vector Labs). Imaging was done with a NanoZoomer slide scanner (Hamamatsu Photonics). Number of Perl's positive cells near the meninges was counted manually.

Results: Overall, there was a low number of microhemorrhages observed in baseline, isotype control and BAMB31 treatment groups (FIG. 8). Biochemistry analysis demonstrated a 34% ($p<0.0001$) reduction for BAMB31_2a versus isotype control antibody for Aβ1-x concentrations in hippocampus (FIG. 9). Additionally, immunohistochemistry with antibody 4G8 showed 23% ($p<0.0001$) and 37% ($p<0.001$) reduction versus isotype control antibody for hippocampus and cortex, respectively.

In conclusion, efficacy for reduction of amyloid burden was demonstrated without causing an increase in the occurrence of microhemorrhages after chronic i.p. injection with BAMB31 in a plaque-depositing mouse model, indicating a favorable ratio of efficacy versus toxicity after treatment with BAMB31 antibody.

Example 10: Pharmacokinetics of a BAMB31 HFA mAb

The pharmacokinetics of a BAMB31 HFA mAb as a wild type IgG1 (BAMB674) and +YTE IgG1 (BAMB675) isotype was assessed in cynomolgus monkeys for direct comparison of properties in the peripheral circulation and brain.

Materials and Methods: Three animals per group were adminstered 25 mg/kg intravenous (i.v.) bolus injection of each mAb and serum samples were collected over a 5 week period. Three additional monkeys were administered a 25 mg/kg i.v. bolus injection of each mAb at week 6 and brain tissue was collected from each group on Day 7 and Day 42 post administration. In total, brain samples were collected from three cynomolgus monkeys at days 7 and 42 for each molecule.

Drug exposure analyses for BAMB674 and BAMB675 from in vivo cynomolgus monkey serum and brain tissue samples were performed by using individual fit-for-purpose electrochemiluminescent immunoassay (ECLIA) methods with endpoint determinations on the Meso Scale Discovery (MSD) Sector Imager 5600. One assay format was applied for each of the compounds and matrices, resulting in four independent methods to measure exposure. The format is described as follows: mAb compounds were captured and detected with an anti-human Fc specific (CH2 Domain) mouse mAb. For the brain tissue preparation, a homogenate was made by cryo-pulverizing snap frozen tissue and diluting in buffer. The protein concentration of the tissue was verified and nominalized using a BCA assay to yield the final protein concentration used in the method. Raw data regression was performed in Watson LIMS software using a 5-parameter logistic (auto-estimate) fit with 1/Y2 standard curve weighting.

A two-compartment (central ($V_C$) and tissue ($V_T$) compartments) pharmacokinetic (PK) model with intravenous (i.v.) administration (Admin) into the central compartment, intercompartmental clearance (Q) and linear clearance (CL) was used to characterize the PK of BAMB674 and BAMB675 in cynomolgus monkeys. FIG. 10 shows the model schematic.

Results: The terminal half-lives for each antibody were calculated and are shown in FIG. 11, along with cynomolgus monkeys data and 2-compartment model fit. The +YTE IgG1 isotype (BAMB675) had an ~1.6 fold increased half-life compared to the wild type IgG1 isotype (BAMB674). This correlates with the ~3-fold increased FcRn affinity of the +YTE isotype (BAMB675) over the wild type IgG1 mAb (BAMB674) shown in Table 5.

Brain lysate levels across regions and between mAbs are similar on Day 7, but only the YTE mAb is consistently detected across brain regions and animals on Day 42. The results of which are shown in FIG. 12. This is consistent with the increased exposure of the +YTE mAb at later time points.

In describing the present invention and its various embodiments, specific terminology is employed for the sake of clarity. However, the invention is not intended to be limited to the specific terminology so selected. A person skilled in the relevant art will recognize that other equivalent components can be employed, and other methods developed without departing from the broad concepts of the current invention. All references cited anywhere in this specification are incorporated by reference as if each had been individually incorporated.

We claim:

1. A method of inducing removal of amyloid plaques in a subject in need thereof, the method comprising administering to the subject in need thereof an isolated monoclonal antibody or antigen binding fragment thereof that specifically binds amyloid-β peptide having pyroglutamate at the third residue (3pE Aβ), wherein the isolated monoclonal antibody or antigen-binding fragment thereof comprises a heavy complementarity determining region 1 (HCDR1), HCDR2, HCDR3, and a light chain complementarity determining region 1 (LCDR1), LCDR2, and LCDR3, having the polypeptide sequences of:

a. SEQ ID NOs: 1, 2, 3, 4, 5, and 6, respectively;
b. SEQ ID NOs: 1, 7, 3, 4, 5, and 6, respectively;
c. SEQ ID NOs: 1, 7, 3, 8, 5, and 6, respectively;
d. SEQ ID NOs: 1, 2, 3, 8, 5, and 6, respectively;
e. SEQ ID NOs: 56, 57, 3, 8, 5, and 6, respectively;
f SEQ ID NOs: 56, 57, 3, 4, 5, and 6, respectively;
g. SEQ ID NOs: 56, 58, 3, 4, 5, and 6, respectively;
h. SEQ ID NOs: 56, 7, 3, 8, 5, and 6, respectively;
i. SEQ ID NOs: 1, 57, 3, 8, 5, and 6, respectively;
j. SEQ ID NOs: 56, 7, 3, 4, 5, and 6, respectively;
k. SEQ ID NOs: 1, 57, 3, 4, 5, and 6, respectively;
l. SEQ ID NOs: 1, 58, 3, 4, 5, and 6, respectively; or
m. SEQ ID NOs: 56, 2, 3, 4, 5, and 6, respectively.

2. The method of claim 1, wherein the isolated monoclonal antibody or antigen-binding fragment thereof comprises a heavy chain variable region having a polypeptide sequence at least 95% identical to SEQ ID NO: 9, 11, 13, 15, 16, 17, 19, 20, or 21, or a light chain variable region having a polypeptide sequence at least 95% identical to SEQ ID NO: 10, 12, 14, 18, 22, 53, or 55.

3. The method of claim 1, wherein the isolated monoclonal antibody or antigen-binding fragment thereof comprises:

a. a heavy chain variable region having the polypeptide sequence of SEQ ID NO:21, and a light chain variable region having the polypeptide sequence of SEQ ID NO:22;
b. a heavy chain variable region having the polypeptide sequence of SEQ ID NO:9, and a light chain variable region having the polypeptide sequence of SEQ ID NO:10;
c. a heavy chain variable region having the polypeptide sequence of SEQ ID NO:11, and a light chain variable region having the polypeptide sequence of SEQ ID NO:12;
d. a heavy chain variable region having the polypeptide sequence of SEQ ID NO:13, and a light chain variable region having the polypeptide sequence of SEQ ID NO:14;
e. a heavy chain variable region having the polypeptide sequence of SEQ ID NO:15, and a light chain variable region having the polypeptide sequence of SEQ ID NO:14;
f. a heavy chain variable region having the polypeptide sequence of SEQ ID NO:16, and a light chain variable region having the polypeptide sequence of SEQ ID NO:14;
g. a heavy chain variable region having the polypeptide sequence of SEQ ID NO:20, and a light chain variable region having the polypeptide sequence of SEQ ID NO:14;
h. a heavy chain variable region having the polypeptide sequence of SEQ ID NO:17, and a light chain variable region having the polypeptide sequence of SEQ ID NO:18;
i. a heavy chain variable region having the polypeptide sequence of SEQ ID NO:19, and a light chain variable region having the polypeptide sequence of SEQ ID NO:18;
j. a heavy chain variable region having the polypeptide sequence of SEQ ID NO:21, and a light chain variable region having the polypeptide sequence of SEQ ID NO:53; or
k. a heavy chain variable region having the polypeptide sequence of SEQ ID NO:21, and a light chain variable region having the polypeptide sequence of SEQ ID NO:55.

4. The method of claim 1, wherein the antibody or antigen-binding fragment thereof is chimeric.

5. The method of claim 1, wherein the isolated monoclonal antibody or antigen-binding fragment thereof is humanized.

6. The method of claim 1, wherein the isolated monoclonal antibody comprises:

a. a heavy chain amino acid sequence comprising SEQ ID NO:37 and a light chain amino acid sequence comprising SEQ ID NO:38;
b. a heavy chain amino acid sequence comprising SEQ ID NO:39 and a light chain amino acid sequence comprising SEQ ID NO:38;
c. a heavy chain amino acid sequence comprising SEQ ID NO:37 and a light chain amino acid sequence comprising SEQ ID NO:52;
d. a heavy chain amino acid sequence comprising SEQ ID NO:39 and a light chain amino acid sequence comprising SEQ ID NO: 52;
e. a heavy chain amino acid sequence comprising SEQ ID NO:37 and a light chain amino acid sequence comprising SEQ ID NO:54; or
f. a heavy chain amino acid sequence comprising SEQ ID NO:39 and a light chain amino acid sequence comprising SEQ ID NO:54.

7. The method of claim 1, wherein the monoclonal antibody or antigen binding fragment thereof is in a pharmaceutical composition, wherein the pharmaceutical composition further comprises a pharmaceutically acceptable carrier.

8. The method of claim 1, wherein the subject has a condition associated with the formation of plaques containing beta-amyloid protein.

9. The method of claim 8, wherein the condition is Alzheimer's disease.

10. The method of claim 8, wherein the condition is selected from the group consisting of dementia associated with Trisomy 21 (Down's Syndrome), diffuse Lewy body disease, inclusion body myositis, cerebral amyloid angiopathy, and hereditary cerebral hemorrhage with amyloidosis of the Dutch-type (HCHWA-D).

* * * * *

SEQUENCE LISTING

```
<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: HCDR1

<400> SEQUENCE: 1

Ser Tyr Asp Met Tyr
1               5


<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Tyr Ile Asp Ser Asp Ser Gly Asp Thr Ser Tyr Asn Gln Lys Phe Lys
1               5                   10                  15

Gly


<210> SEQ ID NO 3
<211> LENGTH: 7
<212> TYPE: PRT
<213> ORGANISM: Artificial Sequence
<220> FEATURE:
<223> OTHER INFORMATION: HCDR3

<400> SEQUENCE: 3

Tyr Arg Tyr Ala Met Asp Tyr
1               5


<210> SEQ ID NO 4
<211> LENGTH: 16
<212> TYPE: PRT
<213> ORGANISM: Artificial Sequence
<220> FEATURE:
<223> OTHER INFORMATION: LCDR1

<400> SEQUENCE: 4

Lys Ser Ser Gln Ser Leu Leu Asp Ser Arg Ala Lys Thr Tyr Leu Thr
```

-continued

```
1               5                   10                  15


<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Leu Val Ser Lys Leu Asp Ser
1               5


<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Trp Gln Gly Thr His Phe Pro Tyr Thr
1               5


<210> SEQ ID NO 7
<211> LENGTH: 17
<212> TYPE: PRT
<213> ORGANISM: Artificial Sequence
<220> FEATURE:
<223> OTHER INFORMATION: HCDR2

<400> SEQUENCE: 7

Tyr Ile Asp Ser Asp Asn Gly Asp Thr Ser Tyr Asn Gln Lys Phe Lys
1               5                   10                  15

Gly


<210> SEQ ID NO 8
<211> LENGTH: 16
<212> TYPE: PRT
<213> ORGANISM: Artificial Sequence
<220> FEATURE:
<223> OTHER INFORMATION: LCDR1

<400> SEQUENCE: 8

Lys Ser Ser Gln Ser Leu Leu Asp Ser Asn Gly Lys Thr Tyr Leu Thr
1               5                   10                  15


<210> SEQ ID NO 9
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 9

Glu Ile Gln Leu Gln Gln Ser Gly Pro Glu Leu Val Lys Pro Gly Thr
1               5                   10                  15

Ser Val Lys Val Ser Cys Lys Ala Ser Gly His Val Phe Thr Ser Tyr
            20                  25                  30

Asp Met Tyr Trp Val Lys Gln Ser His Gly Lys Ser Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
```

```
65                  70                  75                  80

Met His Leu Asn Ser Leu Thr Ser Glu Asp Ser Ala Val Tyr Tyr Cys
                85                  90                  95

Ala Tyr Tyr Arg Tyr Ala Met Asp Tyr Trp Gly Gln Gly Thr Ser Val
            100                 105                 110

Thr Val Ser Ser
        115


<210> SEQ ID NO 10
<211> LENGTH: 112
<212> TYPE: PRT
<213> ORGANISM: Artificial Sequence
<220> FEATURE:
<223> OTHER INFORMATION: Light chain variable region

<400> SEQUENCE: 10

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ala Gly Thr Asp Phe Thr Leu Lys Ile
65                  70                  75                  80

Ile Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110


<210> SEQ ID NO 11
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Gly Leu Glu Trp Met
        35                  40                  45

Gly Tyr Ile Asp Ser Asp Asn Gly Asp Thr Ser Tyr Asn Gln Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115


<210> SEQ ID NO 12
<211> LENGTH: 112
```

<212> TYPE: PRT
<213> ORGANISM: Artificial Sequence
<220> FEATURE:
<223> OTHER INFORMATION: Light chain variable region

<400> SEQUENCE: 12

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Thr Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110
```

<210> SEQ ID NO 13
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ser Pro Gly Gln Gly Leu Glu Trp Ile
        35                  40                  45

Gly Tyr Ile Asp Ser Asp Asn Gly Asp Thr Ser Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115
```

<210> SEQ ID NO 14
<211> LENGTH: 112
<212> TYPE: PRT
<213> ORGANISM: Artificial Sequence
<220> FEATURE:
<223> OTHER INFORMATION: Light chain variable region

<400> SEQUENCE: 14

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Gln Gln Arg Pro Gly Gln Ser
```

```
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110


<210> SEQ ID NO 15
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Gly Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115


<210> SEQ ID NO 16
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Gly Leu Glu Trp Ile
        35                  40                  45

Gly Tyr Ile Asp Ser Asp Asn Gly Asp Thr Ser Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110
```

```
Thr Val Ser Ser
        115


<210> SEQ ID NO 17
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Lys Gln Ala Pro Gly Gln Ser Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115


<210> SEQ ID NO 18
<211> LENGTH: 112
<212> TYPE: PRT
<213> ORGANISM: Artificial Sequence
<220> FEATURE:
<223> OTHER INFORMATION: Light chain variable region

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110


<210> SEQ ID NO 19
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 19

Gln Val Gln Leu Val Gln Ser Gly Ala Glu Val Lys Lys Pro Gly Ala
```

```
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Ser Leu Glu Trp Met
        35                  40                  45

Gly Tyr Ile Asp Ser Asp Asn Gly Asp Thr Ser Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115


<210> SEQ ID NO 20
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Ser Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115


<210> SEQ ID NO 21
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Gly Leu Glu Trp Ile
        35                  40                  45

Gly Tyr Ile Asp Ser Asp Ser Gly Asp Thr Ser Tyr Asn Gln Lys Phe
    50                  55                  60
```

```
Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser
        115


<210> SEQ ID NO 22
<211> LENGTH: 112
<212> TYPE: PRT
<213> ORGANISM: Artificial Sequence
<220> FEATURE:
<223> OTHER INFORMATION: Light chain variable region

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110


<210> SEQ ID NO 23
<211> LENGTH: 446
<212> TYPE: PRT
<213> ORGANISM: Artificial Sequence
<220> FEATURE:
<223> OTHER INFORMATION: Heavy chain

<400> SEQUENCE: 23

Glu Ile Gln Leu Gln Gln Ser Gly Pro Glu Leu Val Lys Pro Gly Thr
1               5                   10                  15

Ser Val Lys Val Ser Cys Lys Ala Ser Gly His Val Phe Thr Ser Tyr
            20                  25                  30

Asp Met Tyr Trp Val Lys Gln Ser His Gly Lys Ser Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Tyr Tyr Arg Tyr Ala Met Asp Tyr Trp Gly Gln Gly Thr Ser Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140
```

Val Lys Gly Tyr Phe Pro Glu Pro Val Thr Leu Thr Trp Asn Ser Gly
145 150 155 160

Ser Leu Ser Ser Gly Val His Thr Phe Pro Ala Val Leu Gln Ser Asp
165 170 175

Leu Tyr Thr Leu Ser Ser Ser Val Thr Val Thr Ser Ser Thr Trp Pro
180 185 190

Ser Gln Ser Ile Thr Cys Asn Val Ala His Pro Ala Ser Ser Thr Lys
195 200 205

Val Asp Lys Lys Ile Glu Pro Arg Gly Pro Thr Ile Lys Pro Cys Pro
210 215 220

Pro Cys Lys Cys Pro Ala Pro Asn Leu Leu Gly Gly Pro Ser Val Phe
225 230 235 240

Ile Phe Pro Pro Lys Ile Lys Asp Val Leu Met Ile Ser Leu Ser Pro
245 250 255

Ile Val Thr Cys Val Val Val Asp Val Ser Glu Asp Asp Pro Asp Val
260 265 270

Gln Ile Ser Trp Phe Val Asn Asn Val Glu Val His Thr Ala Gln Thr
275 280 285

Gln Thr His Arg Glu Asp Tyr Asn Ser Thr Leu Arg Val Val Ser Ala
290 295 300

Leu Pro Ile Gln His Gln Asp Trp Met Ser Gly Lys Glu Phe Lys Cys
305 310 315 320

Lys Val Asn Asn Lys Asp Leu Pro Ala Pro Ile Glu Arg Thr Ile Ser
325 330 335

Lys Pro Lys Gly Ser Val Arg Ala Pro Gln Val Tyr Val Leu Pro Pro
340 345 350

Pro Glu Glu Glu Met Thr Lys Lys Gln Val Thr Leu Thr Cys Met Val
355 360 365

Thr Asp Phe Met Pro Glu Asp Ile Tyr Val Glu Trp Thr Asn Asn Gly
370 375 380

Lys Thr Glu Leu Asn Tyr Lys Asn Thr Glu Pro Val Leu Asp Ser Asp
385 390 395 400

Gly Ser Tyr Phe Met Tyr Ser Lys Leu Arg Val Glu Lys Lys Asn Trp
405 410 415

Val Glu Arg Asn Ser Tyr Ser Cys Ser Val Val His Glu Gly Leu His
420 425 430

Asn His His Thr Thr Lys Ser Phe Ser Arg Thr Pro Gly Lys
435 440 445

<210> SEQ ID NO 24
<211> LENGTH: 219
<212> TYPE: PRT
<213> ORGANISM: Artificial Sequence
<220> FEATURE:
<223> OTHER INFORMATION: Light chain

<400> SEQUENCE: 24

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Ser
20 25 30

Asn Gly Lys Thr Tyr Leu Thr Trp Leu Leu Gln Arg Pro Gly Gln Ser
35 40 45

Pro Lys Arg Leu Ile Tyr Leu Val Ser Lys Leu Asp Ser Gly Val Pro
50 55 60

```
Asp Arg Phe Thr Gly Ser Gly Ala Gly Thr Asp Phe Thr Leu Lys Ile
65                  70                  75                  80

Ile Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 25
<211> LENGTH: 446
<212> TYPE: PRT
<213> ORGANISM: Artificial Sequence
<220> FEATURE:
<223> OTHER INFORMATION: Heavy chain

<400> SEQUENCE: 25

Glu Ile Gln Leu Gln Gln Ser Gly Pro Glu Leu Val Lys Pro Gly Thr
1               5                   10                  15

Ser Val Lys Val Ser Cys Lys Ala Ser Gly His Val Phe Thr Ser Tyr
            20                  25                  30

Asp Met Tyr Trp Val Lys Gln Ser His Gly Lys Ser Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Tyr Tyr Arg Tyr Ala Met Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 26
<211> LENGTH: 219
<212> TYPE: PRT
<213> ORGANISM: Artificial Sequence
<220> FEATURE:
<223> OTHER INFORMATION: Light chain

<400> SEQUENCE: 26

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Thr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ala Gly Thr Asp Phe Thr Leu Lys Ile
65                  70                  75                  80

Ile Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125
```

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 27
<211> LENGTH: 446
<212> TYPE: PRT
<213> ORGANISM: Artificial Sequence
<220> FEATURE:
<223> OTHER INFORMATION: Heavy chain

<400> SEQUENCE: 27

Gln Val Gln Leu Val Gln Ser Gly Ala Glu Val Lys Lys Pro Gly Ala
1 5 10 15

Ser Val Lys Val Ser Cys Lys Ala Ser Gly His Val Phe Thr Ser Tyr
20 25 30

Asp Met Tyr Trp Val Arg Gln Ala Pro Gly Gln Gly Leu Glu Trp Met
35 40 45

Gly Tyr Ile Asp Ser Asp Asn Gly Asp Thr Ser Tyr Asn Gln Lys Phe
50 55 60

Lys Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Tyr Tyr Arg Tyr Ala Met Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

```
Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 28
<211> LENGTH: 219
<212> TYPE: PRT
<213> ORGANISM: Artificial Sequence
<220> FEATURE:
<223> OTHER INFORMATION: Light chain

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Thr Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 29
<211> LENGTH: 446
<212> TYPE: PRT
<213> ORGANISM: Artificial Sequence
<220> FEATURE:
<223> OTHER INFORMATION: Heavy chain

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ser Pro Gly Gln Gly Leu Glu Trp Ile
        35                  40                  45

Gly Tyr Ile Asp Ser Asp Asn Gly Asp Thr Ser Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 30
<211> LENGTH: 219
<212> TYPE: PRT
<213> ORGANISM: Artificial Sequence
<220> FEATURE:
<223> OTHER INFORMATION: Light chain

<400> SEQUENCE: 30

Asp Val Val Met Thr Gln Ser Pro Leu Ser Leu Pro Val Thr Leu Gly
1 5 10 15

Gln Pro Ala Ser Ile Ser Cys Lys Ser Ser Gln Ser Leu Leu Asp Ser
20 25 30

Arg Ala Lys Thr Tyr Leu Thr Trp Leu Gln Gln Arg Pro Gly Gln Ser
35 40 45

Pro Arg Arg Leu Ile Tyr Leu Val Ser Lys Leu Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Trp Gln Gly
85 90 95

Thr His Phe Pro Tyr Thr Phe Gly Gly Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 31
<211> LENGTH: 446
<212> TYPE: PRT
<213> ORGANISM: Artificial Sequence
<220> FEATURE:
<223> OTHER INFORMATION: Heavy chain

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Gly Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 32
<211> LENGTH: 446
<212> TYPE: PRT
<213> ORGANISM: Artificial Sequence
<220> FEATURE:
<223> OTHER INFORMATION: Heavy chain

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Arg Gln Ala Pro Gly Gln Gly Leu Glu Trp Ile
        35                  40                  45

Gly Tyr Ile Asp Ser Asp Asn Gly Asp Thr Ser Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 33
<211> LENGTH: 446
<212> TYPE: PRT
<213> ORGANISM: Artificial Sequence
<220> FEATURE:
<223> OTHER INFORMATION: Heavy chain

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly His Val Phe Thr Ser Tyr
            20                  25                  30

Asp Met Tyr Trp Val Lys Gln Ala Pro Gly Gln Ser Leu Glu Trp Ile
        35                  40                  45

Gly Tyr Ile Asp Ser Asp Asn Gly Asp Thr Ser Tyr Asn Gln Lys Phe
    50                  55                  60

Lys Gly Lys Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Arg Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 34
<211> LENGTH: 219
<212> TYPE: PRT
<213> ORGANISM: Artificial Sequence
<220> FEATURE:
<223> OTHER INFORMATION: Light chain

<400> SEQUENCE: 34

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 35
<211> LENGTH: 446
<212> TYPE: PRT
<213> ORGANISM: Artificial Sequence
<220> FEATURE:
<223> OTHER INFORMATION: Heavy chain

<400> SEQUENCE: 35

Gln Val Gln Leu Val Gln Ser Gly Ala Glu Val Lys Lys Pro Gly Ala
1 5 10 15

Ser Val Lys Val Ser Cys Lys Ala Ser Gly His Val Phe Thr Ser Tyr
20 25 30

Asp Met Tyr Trp Val Arg Gln Ala Pro Gly Gln Ser Leu Glu Trp Met
35 40 45

Gly Tyr Ile Asp Ser Asp Asn Gly Asp Thr Ser Tyr Asn Gln Lys Phe
50 55 60

Lys Gly Arg Val Thr Leu Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Tyr Tyr Arg Tyr Ala Met Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 36
<211> LENGTH: 446
<212> TYPE: PRT
<213> ORGANISM: Artificial Sequence
<220> FEATURE:
<223> OTHER INFORMATION: Heavy chain

<400> SEQUENCE: 36

Gln Val Gln Leu Val Gln Ser Gly Ala Glu Val Lys Lys Pro Gly Ala
1 5 10 15

Ser Val Lys Val Ser Cys Lys Ala Ser Gly His Val Phe Thr Ser Tyr
20 25 30

Asp Met Tyr Trp Val Arg Gln Ala Pro Gly Gln Ser Leu Glu Trp Ile
35 40 45

Gly Tyr Ile Asp Ser Asp Asn Gly Asp Thr Ser Tyr Asn Gln Lys Phe
50 55 60

Lys Gly Lys Ala Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Tyr Tyr Arg Tyr Ala Met Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 37
<211> LENGTH: 446
<212> TYPE: PRT
<213> ORGANISM: Artificial Sequence
<220> FEATURE:
<223> OTHER INFORMATION: Heavy chain

<400> SEQUENCE: 37

Gln Val Gln Leu Val Gln Ser Gly Ala Glu Val Lys Lys Pro Gly Ala
1 5 10 15

Ser Val Lys Val Ser Cys Lys Ala Ser Gly His Val Phe Thr Ser Tyr
20 25 30

Asp Met Tyr Trp Val Arg Gln Ala Pro Gly Gln Gly Leu Glu Trp Ile
35 40 45

Gly Tyr Ile Asp Ser Asp Ser Gly Asp Thr Ser Tyr Asn Gln Lys Phe
50 55 60

Lys Gly Arg Val Thr Leu Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Tyr Tyr Arg Tyr Ala Met Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 38
<211> LENGTH: 219
<212> TYPE: PRT
<213> ORGANISM: Artificial Sequence
<220> FEATURE:
<223> OTHER INFORMATION: Light chain

<400> SEQUENCE: 38

Asp Val Val Met Thr Gln Ser Pro Leu Ser Leu Pro Val Thr Leu Gly
1 5 10 15

Gln Pro Ala Ser Ile Ser Cys Lys Ser Ser Gln Ser Leu Leu Asp Ser
20 25 30

Arg Ala Lys Thr Tyr Leu Thr Trp Leu Gln Gln Arg Pro Gly Gln Ser
35 40 45

Pro Arg Arg Leu Ile Tyr Leu Val Ser Lys Leu Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Trp Gln Gly
85 90 95

Thr His Phe Pro Tyr Thr Phe Gly Gly Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 39
<211> LENGTH: 446
<212> TYPE: PRT
<213> ORGANISM: Artificial Sequence
<220> FEATURE:
<223> OTHER INFORMATION: Heavy chain

<400> SEQUENCE: 39

Gln Val Gln Leu Val Gln Ser Gly Ala Glu Val Lys Lys Pro Gly Ala
1 5 10 15

Ser Val Lys Val Ser Cys Lys Ala Ser Gly His Val Phe Thr Ser Tyr
20 25 30

Asp Met Tyr Trp Val Arg Gln Ala Pro Gly Gln Gly Leu Glu Trp Ile
35 40 45

Gly Tyr Ile Asp Ser Asp Ser Gly Asp Thr Ser Tyr Asn Gln Lys Phe
50 55 60

Lys Gly Arg Val Thr Leu Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Tyr Tyr Arg Tyr Ala Met Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Tyr Ile Thr Arg Glu Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 40
<211> LENGTH: 38
<212> TYPE: PRT
<213> ORGANISM: Artificial Sequence
<220> FEATURE:
<223> OTHER INFORMATION: human A(beta)3pE-40
<220> FEATURE:
<221> NAME/KEY: MISC_FEATURE
<222> LOCATION: (1)..(1)
<223> OTHER INFORMATION: Pyroglutamate residue

<400> SEQUENCE: 40

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 41
<211> LENGTH: 40
<212> TYPE: PRT
<213> ORGANISM: Artificial Sequence
<220> FEATURE:
<223> OTHER INFORMATION: human A(beta)1-40

<400> SEQUENCE: 41

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val Val
35 40

<210> SEQ ID NO 42
<211> LENGTH: 26
<212> TYPE: PRT
<213> ORGANISM: Artificial Sequence
<220> FEATURE:
<223> OTHER INFORMATION: human A(beta)3pE-28
<220> FEATURE:
<221> NAME/KEY: MISC_FEATURE
<222> LOCATION: (1)..(1)
<223> OTHER INFORMATION: Pyroglutamate residue

<400> SEQUENCE: 42

Glu Phe Arg His Asp Ser Gly Tyr Glu Val His His Gln Lys Leu Val
1 5 10 15

Phe Phe Ala Glu Asp Val Gly Ser Asn Lys
20 25

<210> SEQ ID NO 43
<211> LENGTH: 28
<212> TYPE: PRT
<213> ORGANISM: Artificial Sequence
<220> FEATURE:
<223> OTHER INFORMATION: human A(beta)1-28

<400> SEQUENCE: 43

Asp Ala Glu Phe Arg His Asp Ser Gly Tyr Glu Val His His Gln Lys
1 5 10 15

Leu Val Phe Phe Ala Glu Asp Val Gly Ser Asn Lys
20 25

<210> SEQ ID NO 44
<211> LENGTH: 26
<212> TYPE: PRT
<213> ORGANISM: Artificial Sequence
<220> FEATURE:
<223> OTHER INFORMATION: human A(beta)3pE-28 scrambled
<220> FEATURE:
<221> NAME/KEY: MISC_FEATURE
<222> LOCATION: (1)..(1)
<223> OTHER INFORMATION: Pyroglutamate residue

<400> SEQUENCE: 44

Glu Gly Phe Asp Ser Arg His Tyr Glu Val His His Gln Lys Leu Val
1 5 10 15

Phe Phe Ala Glu Asp Val Gly Ser Asn Lys
20 25

<210> SEQ ID NO 45
<211> LENGTH: 38
<212> TYPE: PRT
<213> ORGANISM: Artificial Sequence
<220> FEATURE:
<223> OTHER INFORMATION: mouse A(beta)3pE-40
<220> FEATURE:
<221> NAME/KEY: MISC_FEATURE
<222> LOCATION: (1)..(1)
<223> OTHER INFORMATION: Pyroglutamate residue

<400> SEQUENCE: 45

-continued

```
Glu Phe Gly His Asp Ser Gly Phe Glu Val Arg His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35


<210> SEQ ID NO 46
<211> LENGTH: 26
<212> TYPE: PRT
<213> ORGANISM: Artificial Sequence
<220> FEATURE:
<223> OTHER INFORMATION: mouse A(beta)3pE-28
<220> FEATURE:
<221> NAME/KEY: MISC_FEATURE
<222> LOCATION: (1)..(1)
<223> OTHER INFORMATION: Pyroglutamate residue

<400> SEQUENCE: 46

Glu Phe Gly His Asp Ser Gly Phe Glu Val Arg His Gln Lys Leu Val
1               5                   10                  15

Phe Phe Ala Glu Asp Val Gly Ser Asn Lys
            20                  25


<210> SEQ ID NO 47
<211> LENGTH: 8
<212> TYPE: PRT
<213> ORGANISM: Artificial Sequence
<220> FEATURE:
<223> OTHER INFORMATION: Peptide boost
<220> FEATURE:
<221> NAME/KEY: MISC_FEATURE
<222> LOCATION: (1)..(1)
<223> OTHER INFORMATION: Pyroglutamate residue

<400> SEQUENCE: 47

Glu Phe Arg His Asp Ser Gly Cys
1               5


<210> SEQ ID NO 48
<211> LENGTH: 42
<212> TYPE: PRT
<213> ORGANISM: Artificial Sequence
<220> FEATURE:
<223> OTHER INFORMATION: A(beta)1-42

<400> SEQUENCE: 48

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40


<210> SEQ ID NO 49
<211> LENGTH: 30
<212> TYPE: PRT
<213> ORGANISM: Artificial Sequence
<220> FEATURE:
<223> OTHER INFORMATION: A(beta)11pE-40
<220> FEATURE:
<221> NAME/KEY: MISC_FEATURE
<222> LOCATION: (1)..(1)
<223> OTHER INFORMATION: Pyroglutamate residue

<400> SEQUENCE: 49
```

```
Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30


<210> SEQ ID NO 50
<211> LENGTH: 32
<212> TYPE: PRT
<213> ORGANISM: Artificial Sequence
<220> FEATURE:
<223> OTHER INFORMATION: A(beta)11pE-42
<220> FEATURE:
<221> NAME/KEY: MISC_FEATURE
<222> LOCATION: (1)..(1)
<223> OTHER INFORMATION: Pyroglutamate residue

<400> SEQUENCE: 50

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30


<210> SEQ ID NO 51
<211> LENGTH: 40
<212> TYPE: PRT
<213> ORGANISM: Artificial Sequence
<220> FEATURE:
<223> OTHER INFORMATION: A(beta)3pE-42
<220> FEATURE:
<221> NAME/KEY: MISC_FEATURE
<222> LOCATION: (1)..(1)
<223> OTHER INFORMATION: Pyroglutamate residue

<400> SEQUENCE: 51

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40


<210> SEQ ID NO 52
<211> LENGTH: 219
<212> TYPE: PRT
<213> ORGANISM: Artificial Sequence
<220> FEATURE:
<223> OTHER INFORMATION: Light chain

<400> SEQUENCE: 52

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 53
<211> LENGTH: 112
<212> TYPE: PRT
<213> ORGANISM: Artificial Sequence
<220> FEATURE:
<223> OTHER INFORMATION: Light chain variable region

<400> SEQUENCE: 53

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110


<210> SEQ ID NO 54
<211> LENGTH: 219
<212> TYPE: PRT
<213> ORGANISM: Artificial Sequence
<220> FEATURE:
<223> OTHER INFORMATION: Light chain

<400> SEQUENCE: 54

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
```

```
                85                  90                  95

Thr His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 55
<211> LENGTH: 112
<212> TYPE: PRT
<213> ORGANISM: Artificial Sequence
<220> FEATURE:
<223> OTHER INFORMATION: Light chain variable region

<400> SEQUENCE: 55

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Arg Ala Lys Thr Tyr Leu Thr Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110


<210> SEQ ID NO 56
<211> LENGTH: 10
<212> TYPE: PRT
<213> ORGANISM: Artificial Sequence
<220> FEATURE:
<223> OTHER INFORMATION: HCDR1

<400> SEQUENCE: 56

Gly His Val Phe Thr Ser Tyr Asp Met Tyr
1               5                   10


<210> SEQ ID NO 57
<211> LENGTH: 8
<212> TYPE: PRT
<213> ORGANISM: Artificial Sequence
<220> FEATURE:
<223> OTHER INFORMATION: HCDR2

<400> SEQUENCE: 57
```

-continued

```
Asp Ser Asp Asn Gly Asp Thr Ser
1               5


<210> SEQ ID NO 58
<211> LENGTH: 10
<212> TYPE: PRT
<213> ORGANISM: Artificial Sequence
<220> FEATURE:
<223> OTHER INFORMATION: HCDR2

<400> SEQUENCE: 58

Tyr Ile Asp Ser Asp Ser Gly Asp Thr Ser
1               5                   10
```